(12) United States Patent
Forsell

(10) Patent No.: US 10,549,107 B2
(45) Date of Patent: Feb. 4, 2020

(54) ENERGY TRANSFER CONTROL ADAPTED TO A MEDICAL DEVICE SYSTEM

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 15/803,989

(22) Filed: Nov. 6, 2017

(65) Prior Publication Data

US 2018/0133488 A1    May 17, 2018

Related U.S. Application Data

(63) Continuation of application No. 14/091,995, filed on Nov. 27, 2013, now Pat. No. 9,808,634, which is a continuation of application No. 12/682,336, filed as application No. PCT/SE2008/000665 on Nov. 27, 2008, now Pat. No. 8,600,517.

(60) Provisional application No. 60/996,601, filed on Nov. 27, 2007.

(51) Int. Cl.
| | | |
|---|---|---|
| *A61N 1/378* | (2006.01) | |
| *H02J 50/00* | (2016.01) | |
| *H02J 50/80* | (2016.01) | |
| *A61N 1/36* | (2006.01) | |
| *A61N 1/372* | (2006.01) | |
| *H02J 5/00* | (2016.01) | |
| *H02J 7/02* | (2016.01) | |
| *H02J 17/00* | (2006.01) | |

(52) U.S. Cl.
CPC ....... *A61N 1/3787* (2013.01); *A61N 1/36125* (2013.01); *A61N 1/37211* (2013.01); *H02J 50/00* (2016.02); *H02J 50/80* (2016.02); *H02J 17/00* (2013.01)

(58) Field of Classification Search
CPC .............. A61N 1/3787; A61N 1/36125; A61N 1/37211; H02J 50/80; H02J 50/00; H02J 5/005; H02J 7/025; H02J 17/00
See application file for complete search history.

(56) References Cited

U.S. PATENT DOCUMENTS

| | | | |
|---|---|---|---|
| 5,702,431 A | * | 12/1997 | Wang ............... A61N 1/3787 607/33 |
| 6,442,434 B1 | | 8/2002 | Zarinetchi |
| 6,772,011 B2 | | 8/2004 | Dolgin |
| 2007/0156204 A1 | | 7/2007 | Denker |

FOREIGN PATENT DOCUMENTS

WO    WO 9837926 A1 *  9/1998  ........... A61B 5/0031

\* cited by examiner

*Primary Examiner* — Lindsey G Wehrheim

(57) ABSTRACT

A method of transmitting wireless energy from an external energy transmitting device placed externally to a human body to an internal energy receiver placed internally in the human body. The method comprises applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses. The method further comprises transmitting wireless energy, the transmitted energy generated from the electrical pulses having a varied power, the varying of the power depending on the lengths of the first and/or second time intervals.

25 Claims, 49 Drawing Sheets

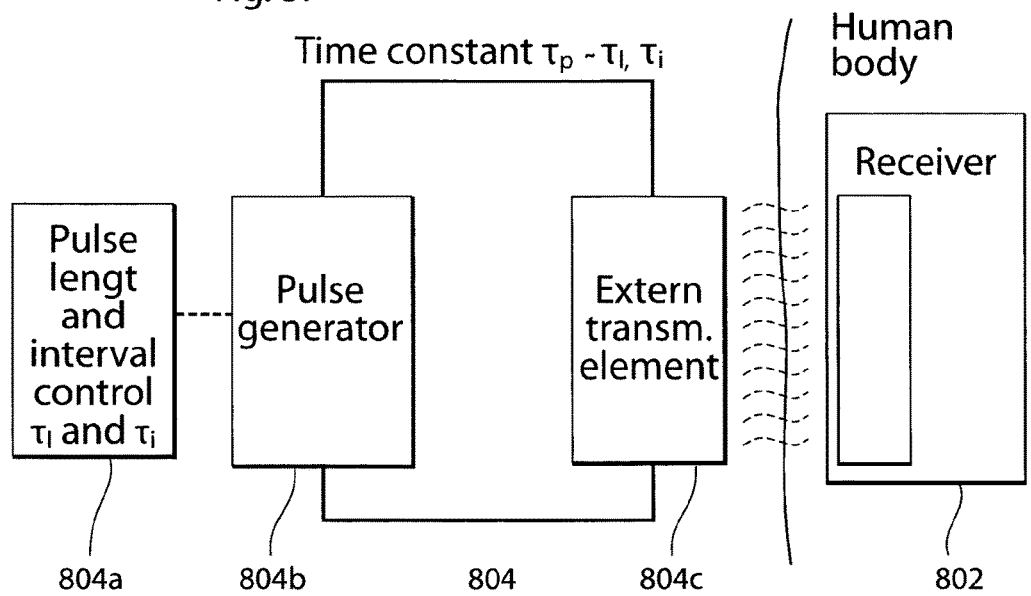
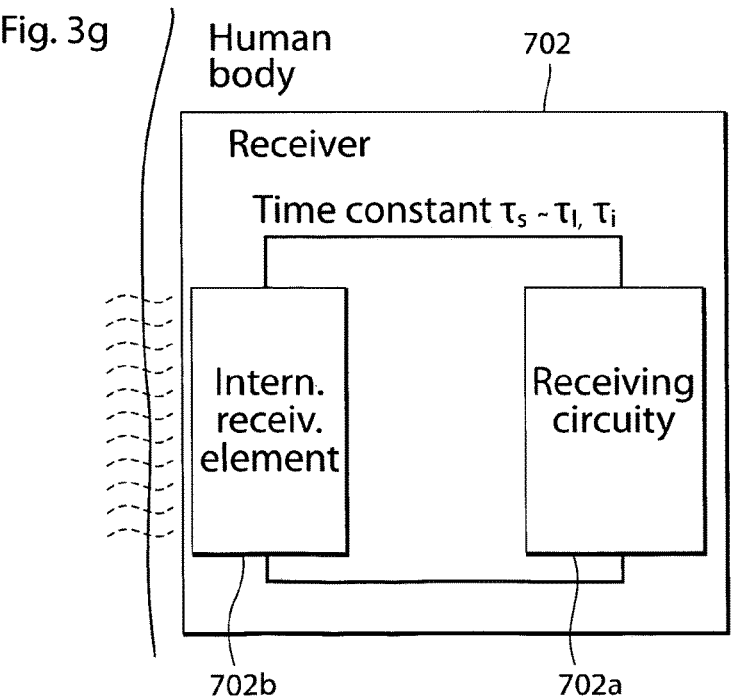

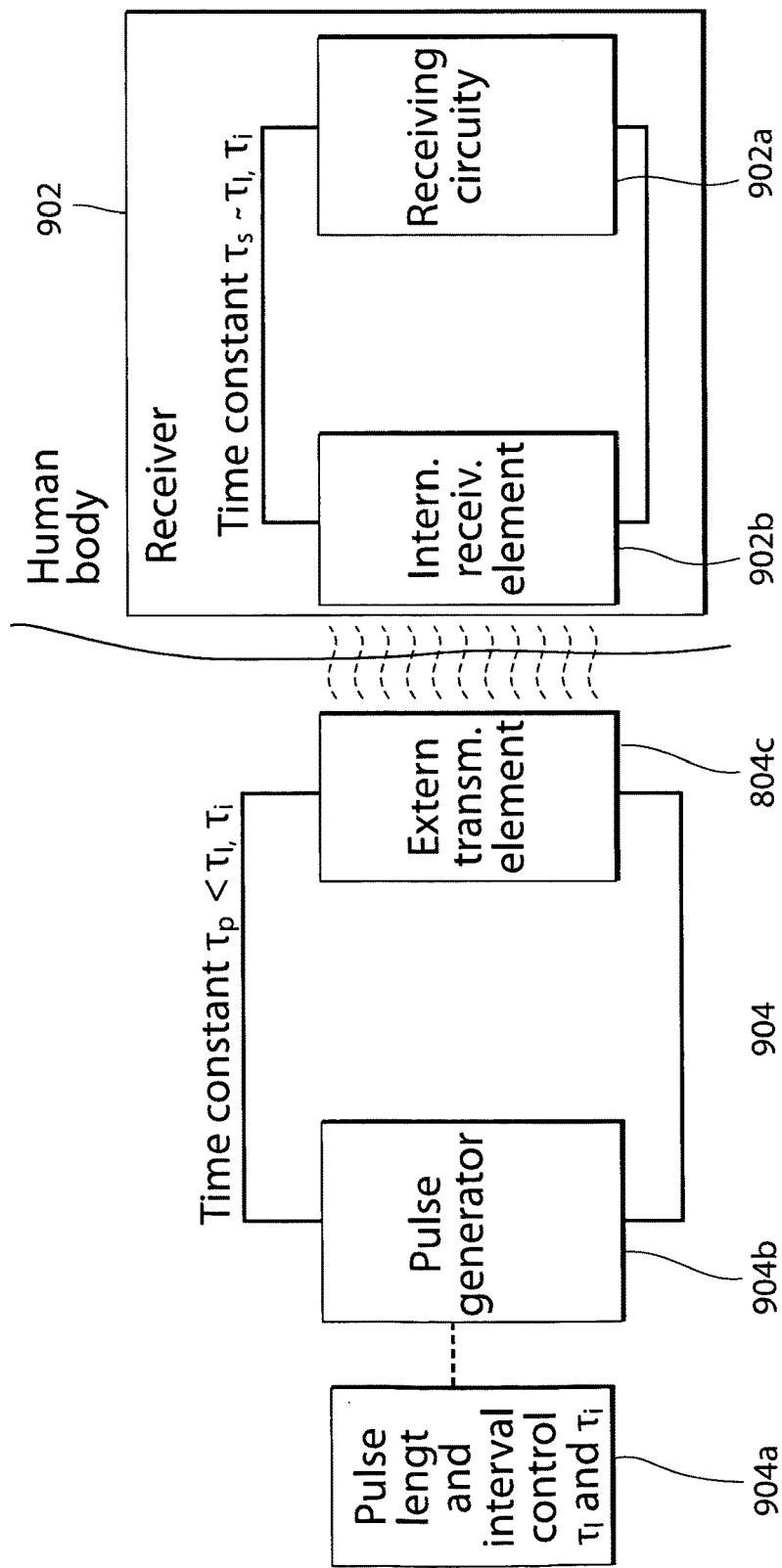

Applied pulses

Applied pulses

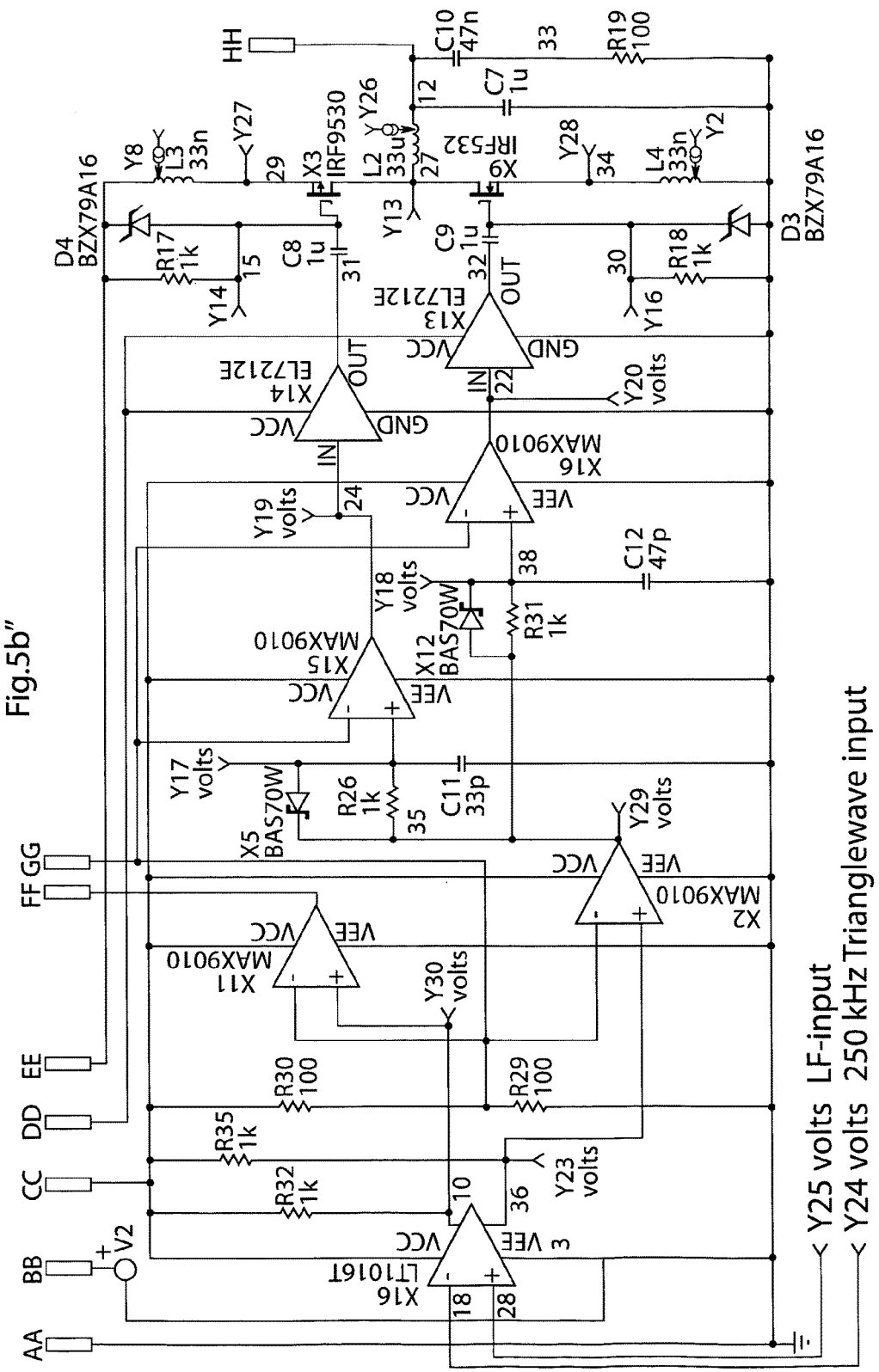
Fig.5b"

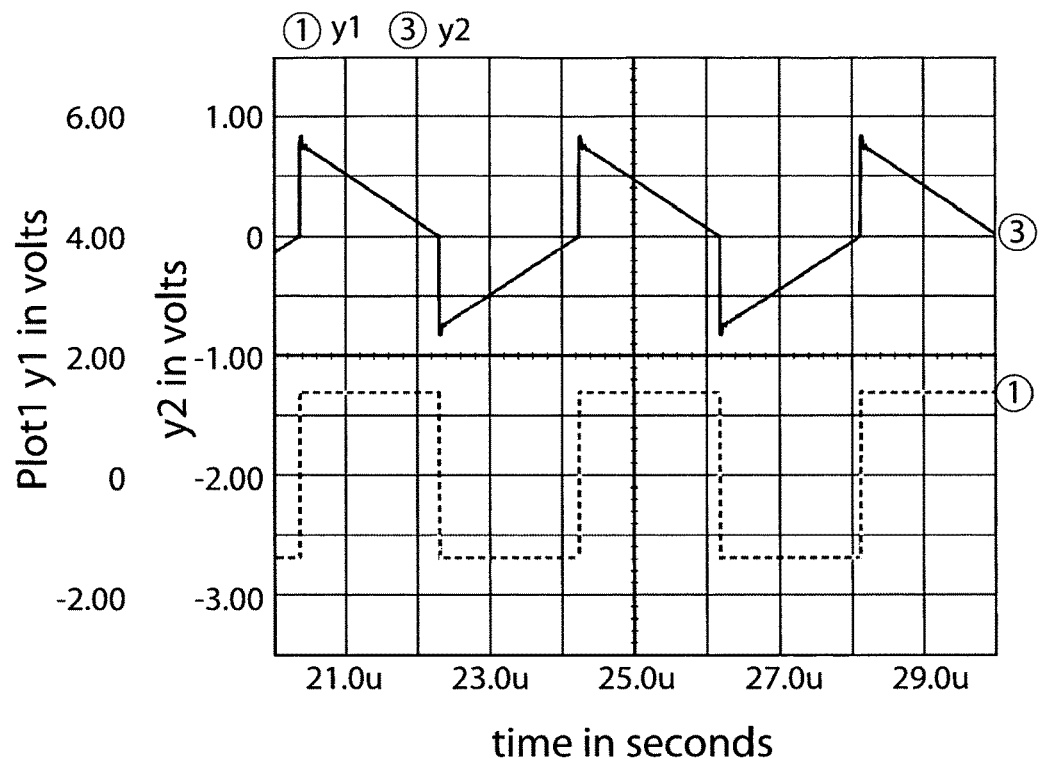
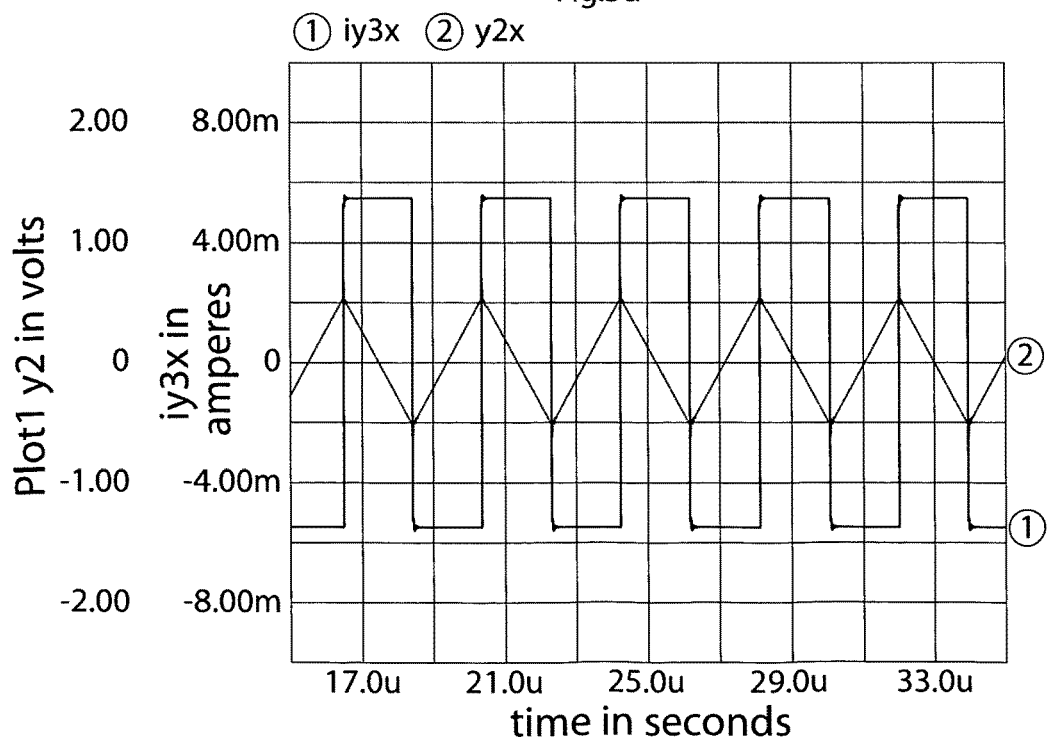

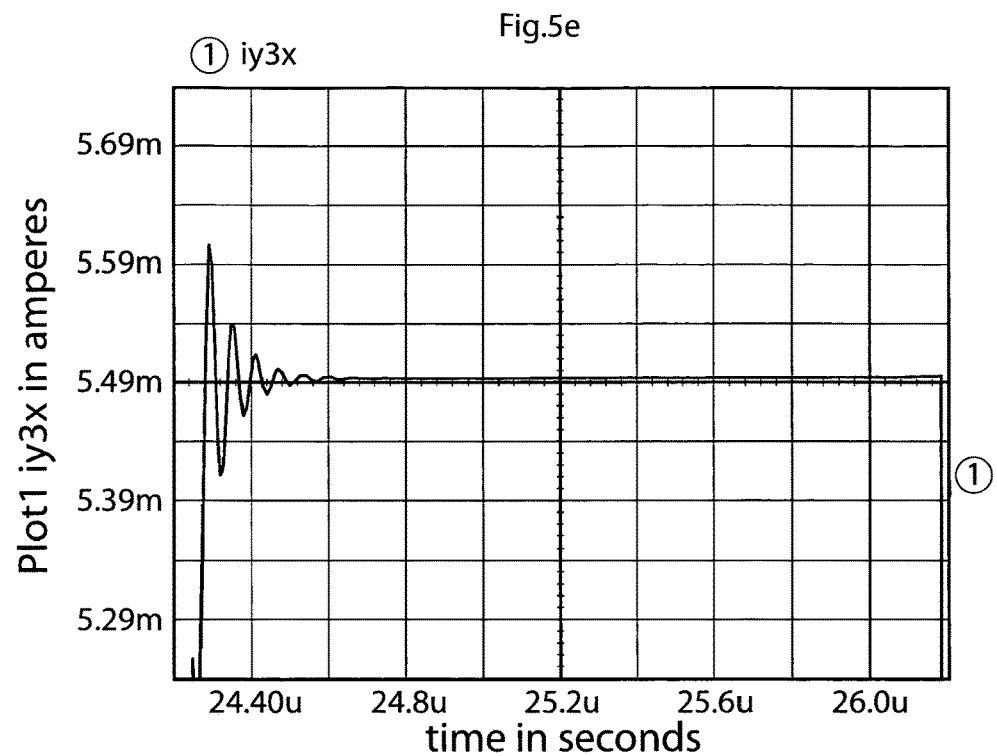
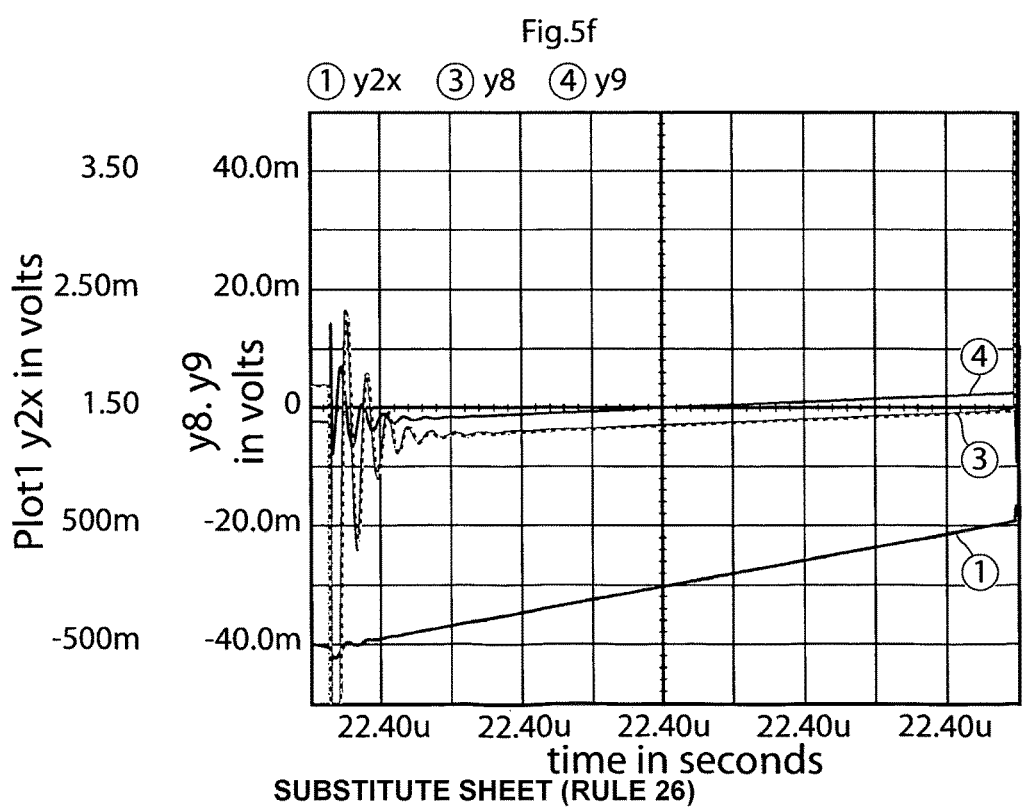

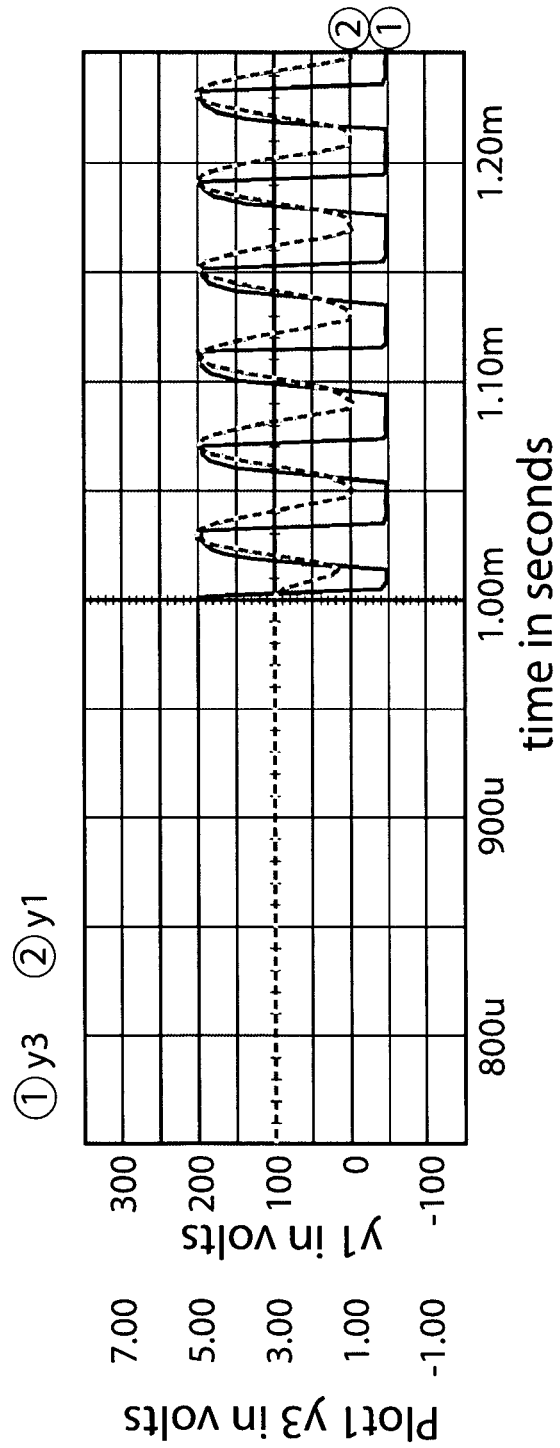

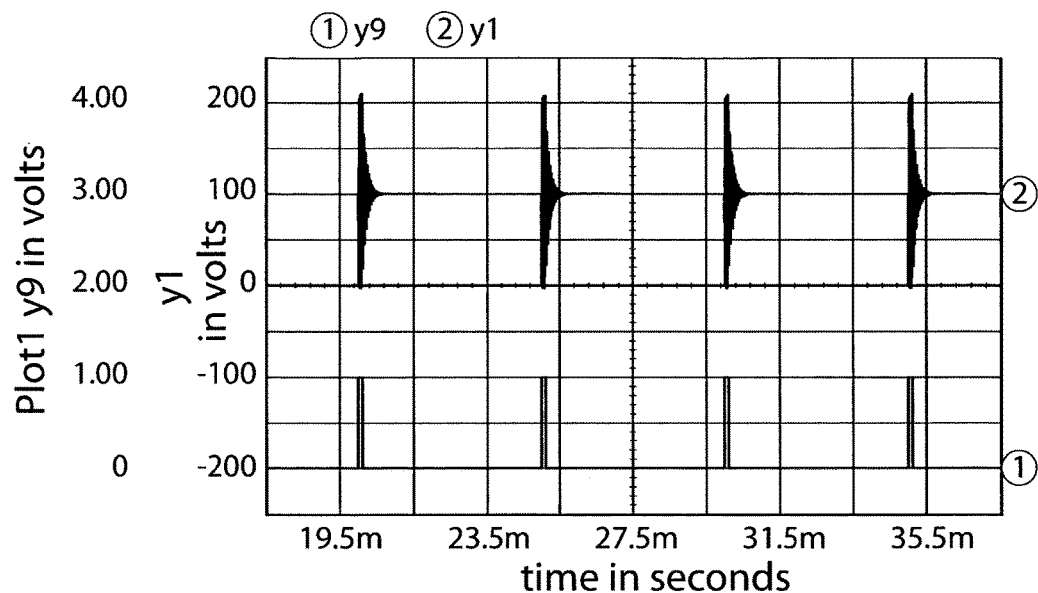
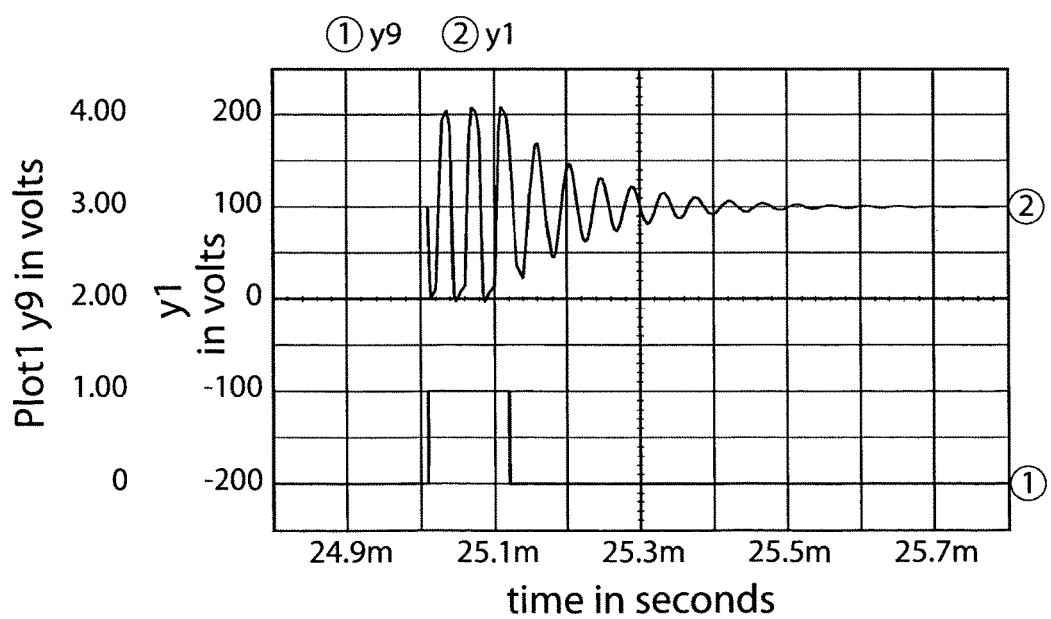

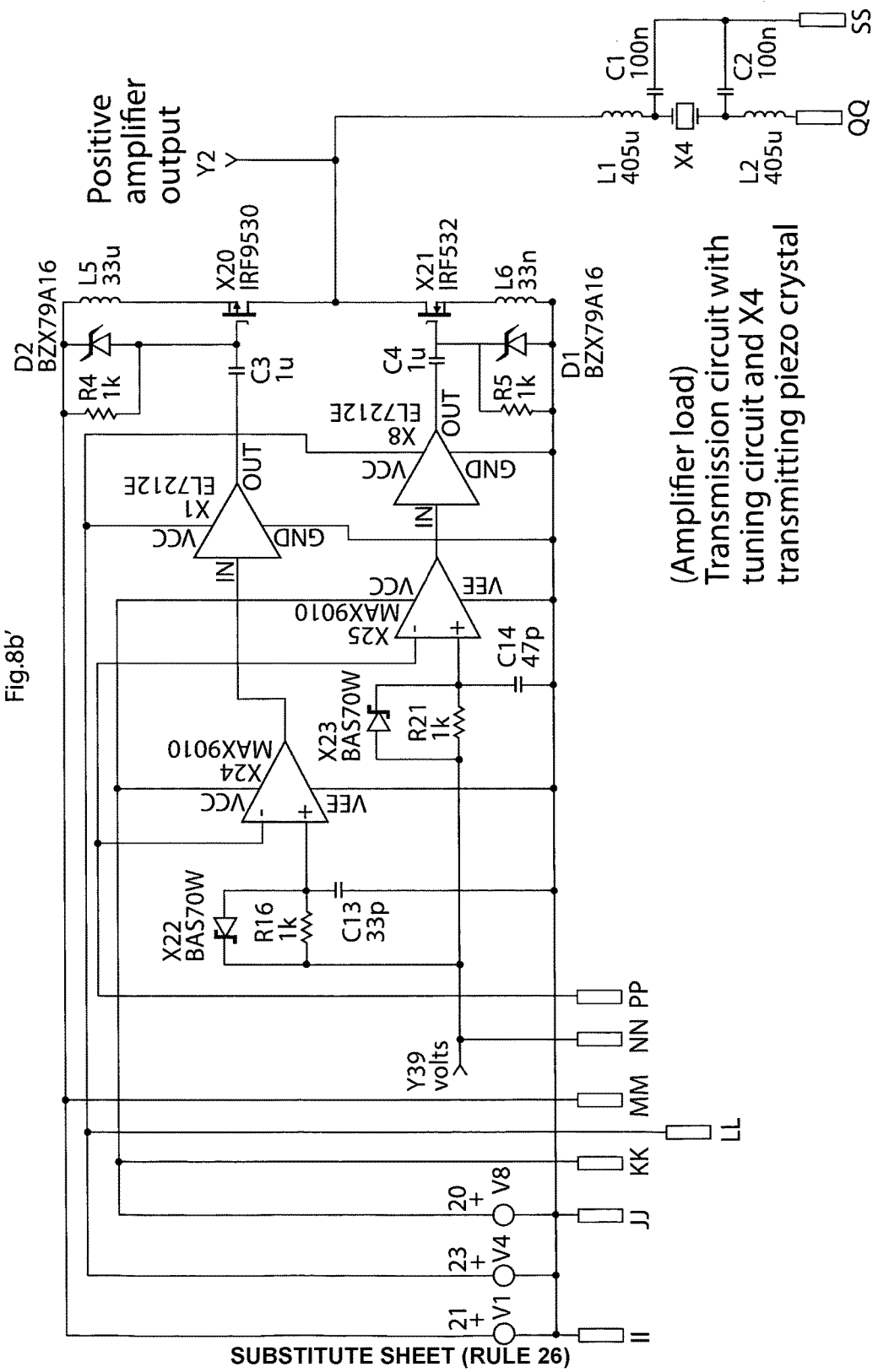

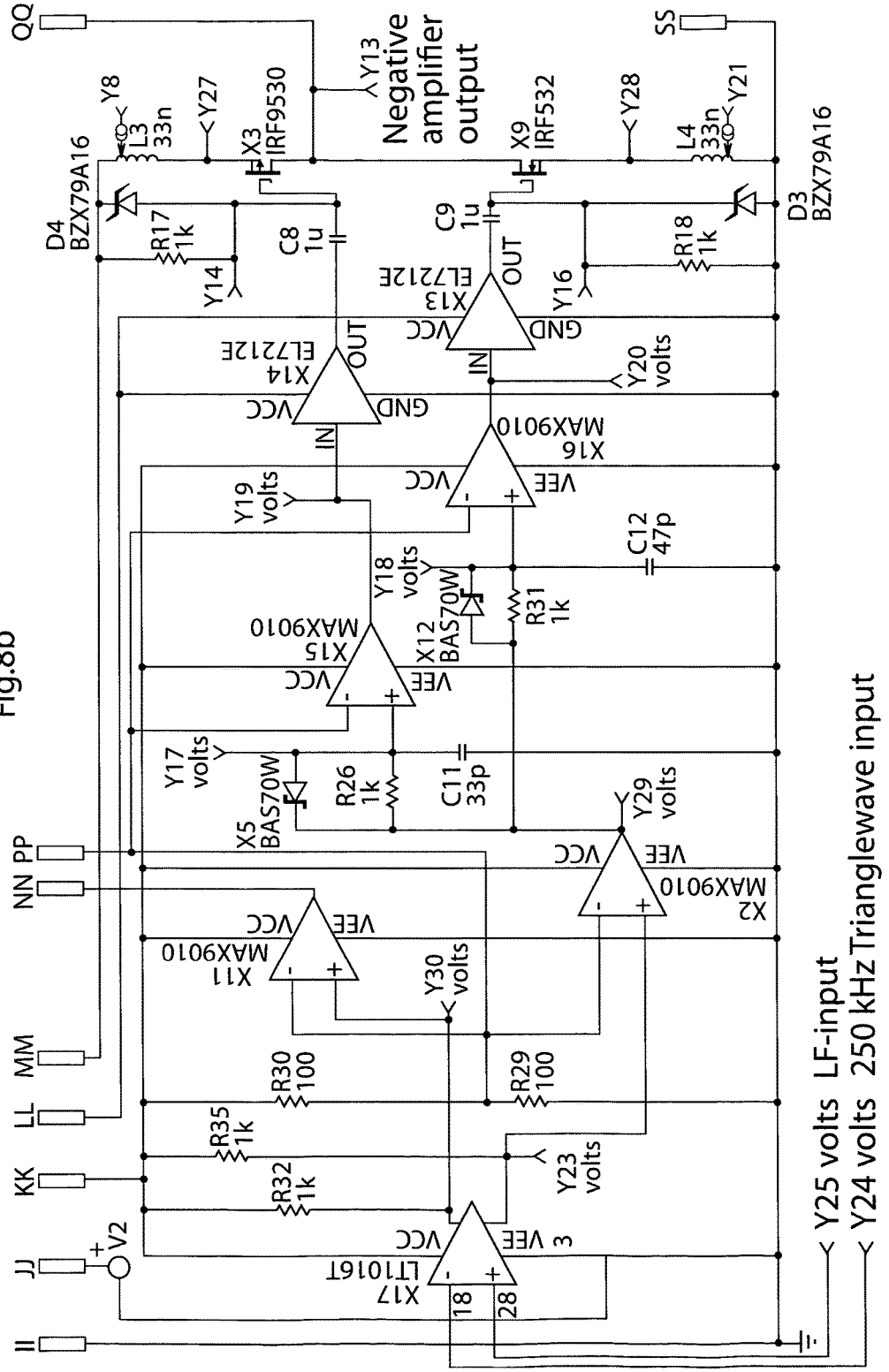
Fig. 8b"

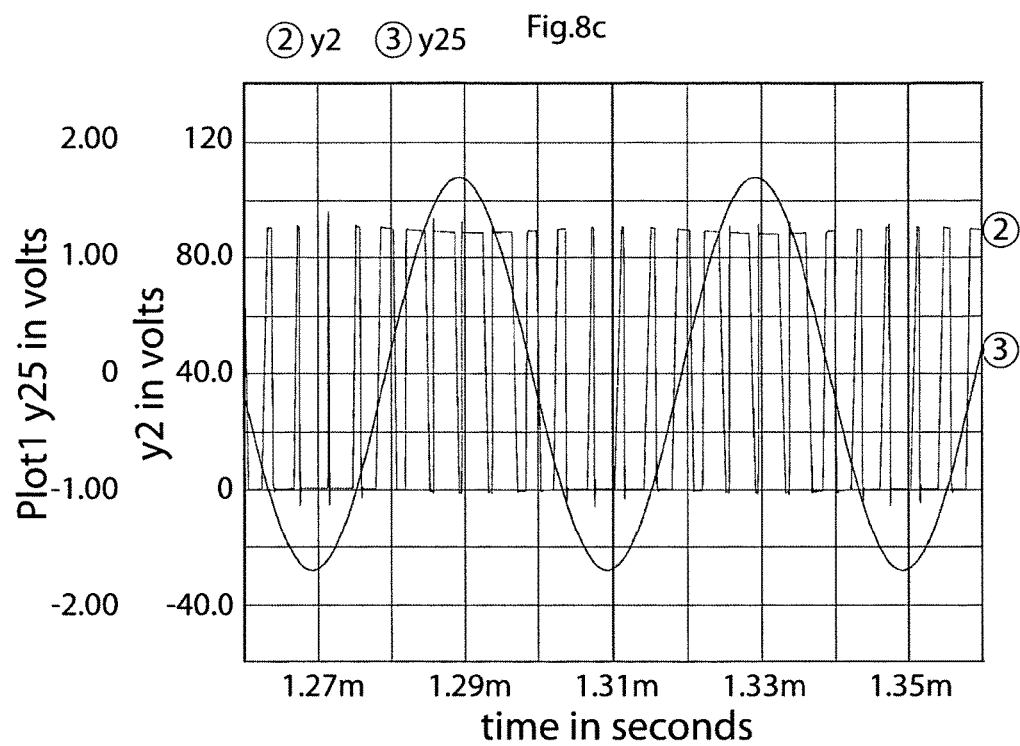
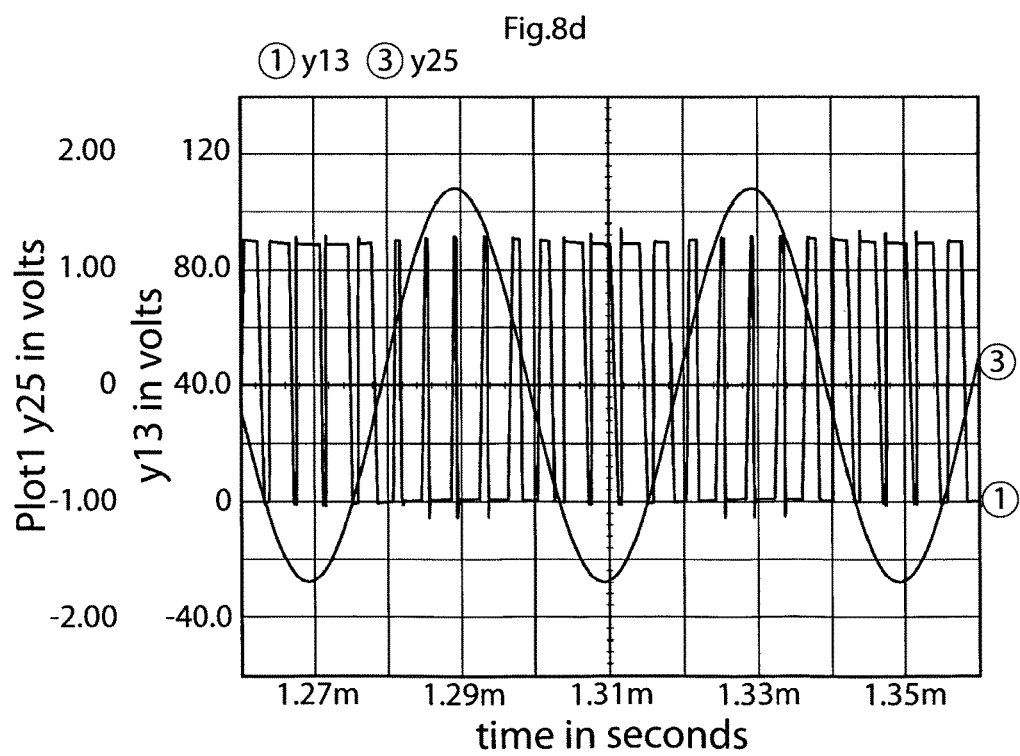

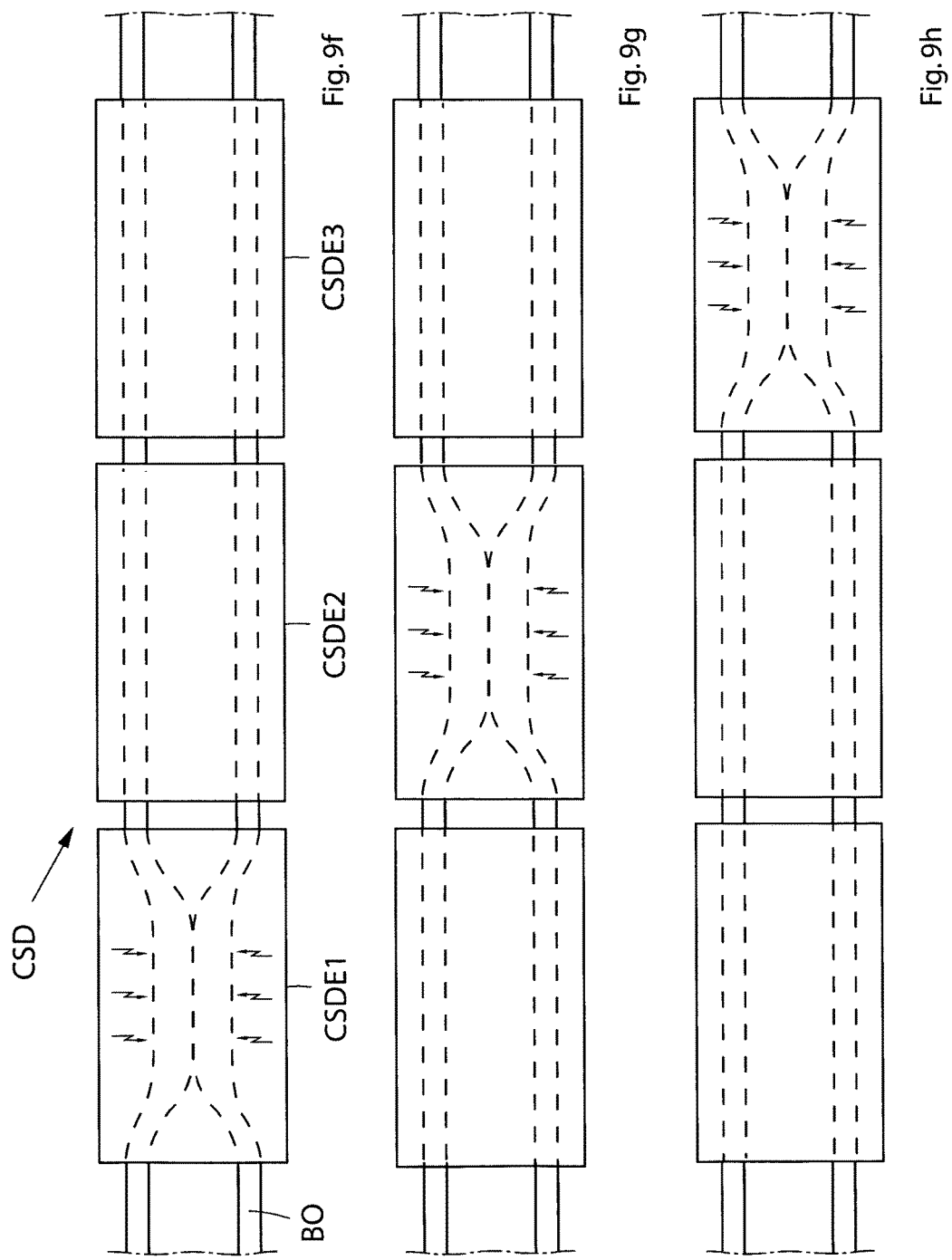

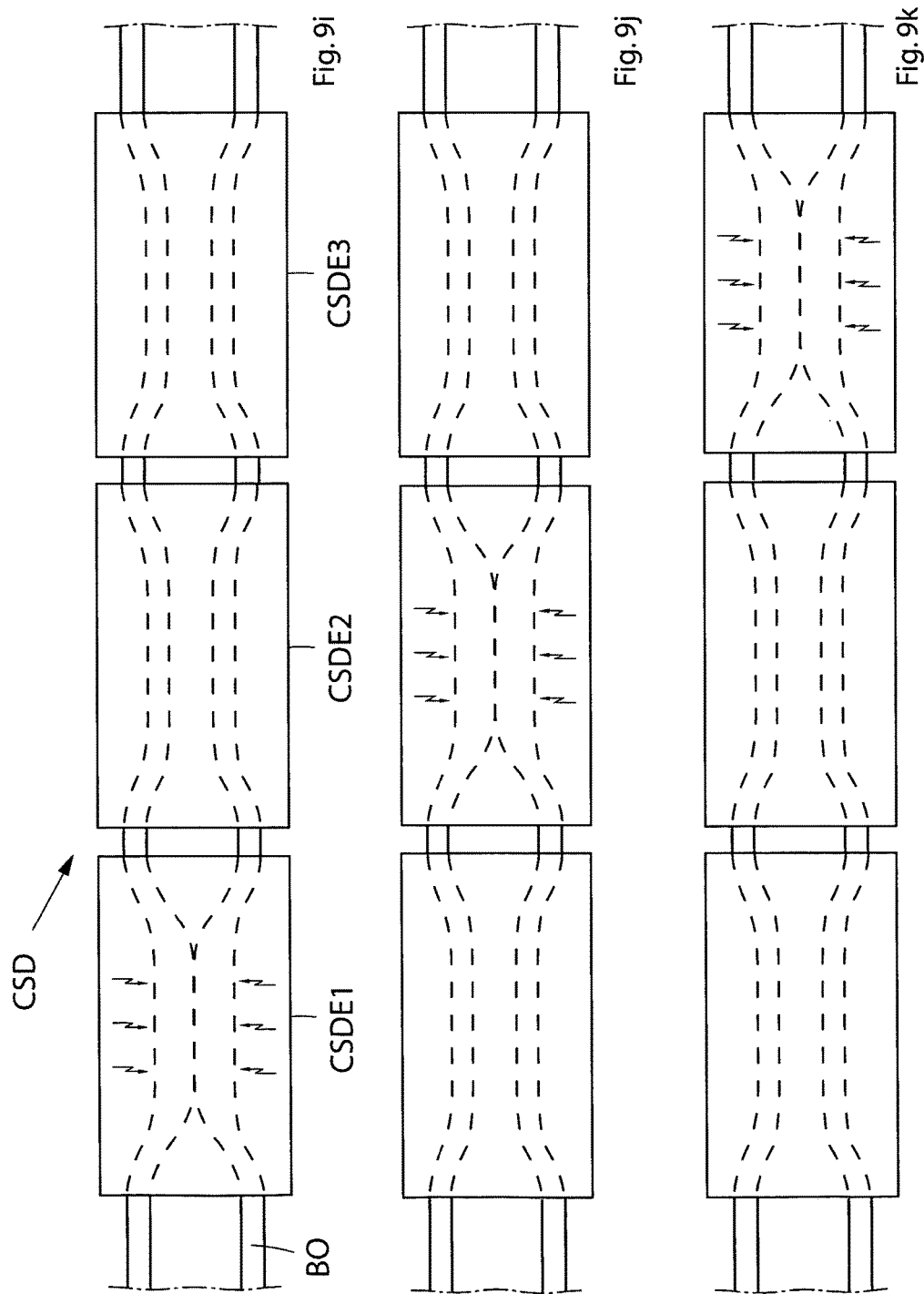

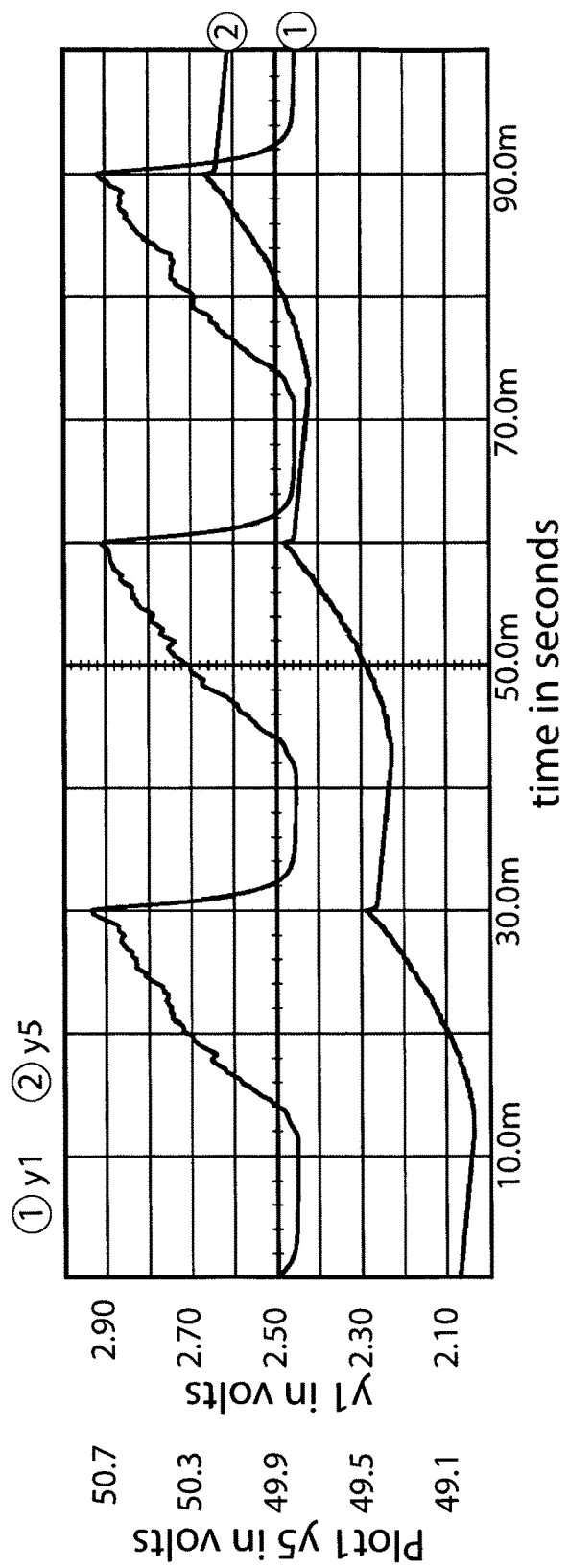

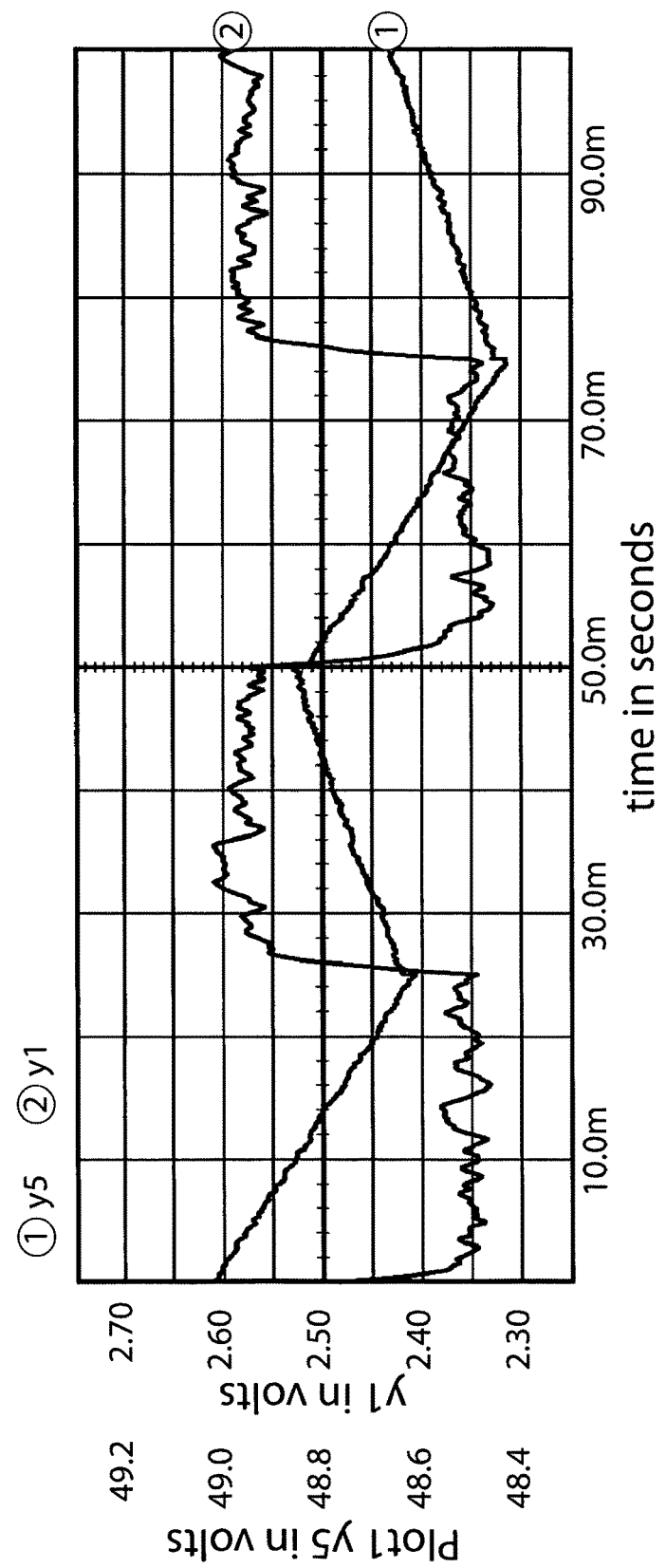

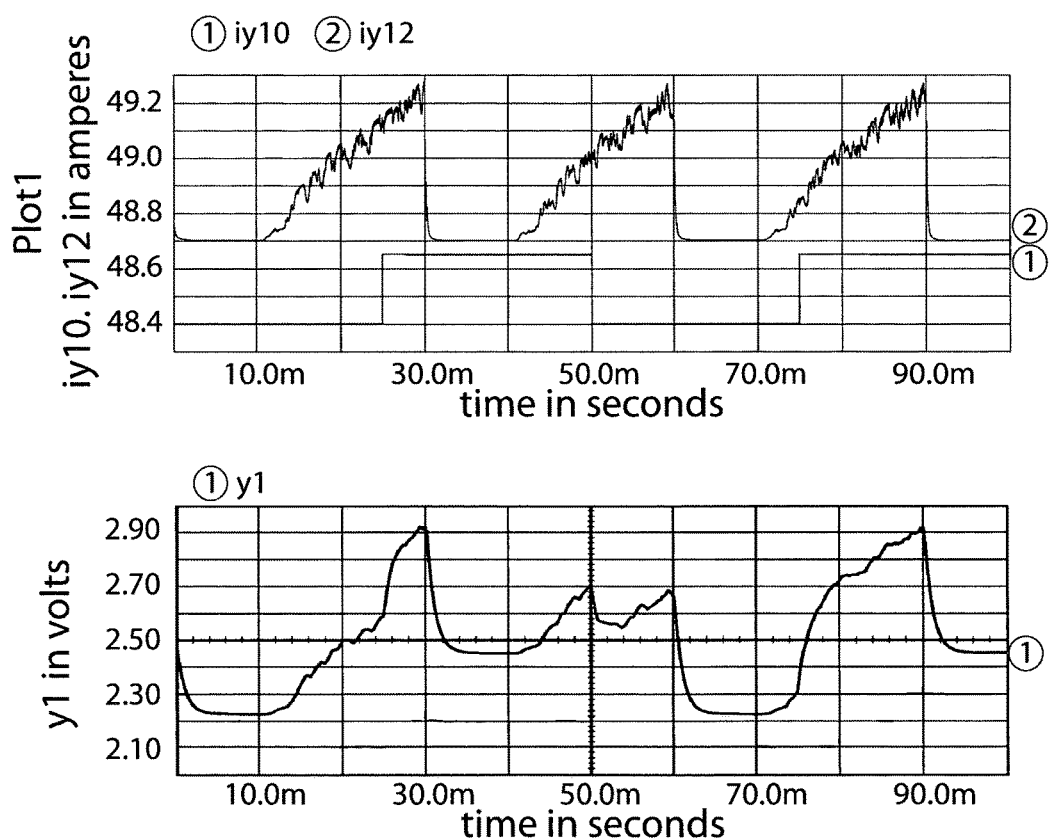

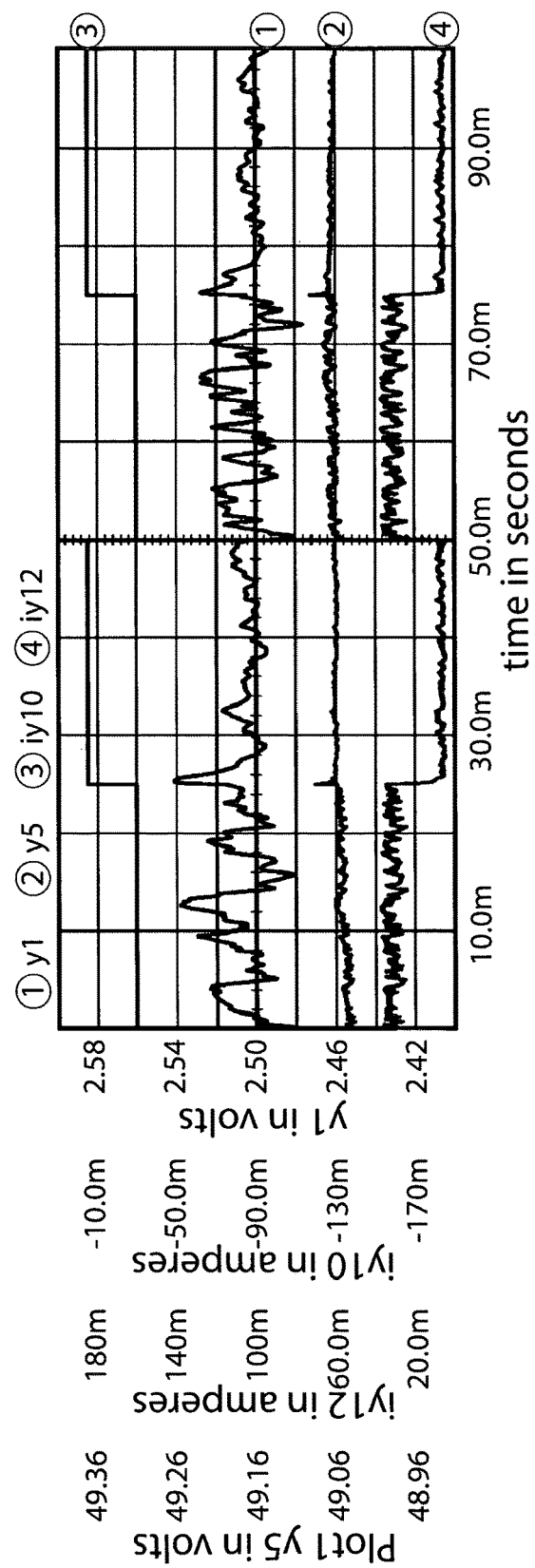

ENERGY TRANSFER CONTROL ADAPTED TO A MEDICAL DEVICE SYSTEM

This application is a continuation of U.S. application Ser. No. 14/091,995, filed Nov. 27, 2013, which is a continuation of U.S. application Ser. No. 12/682,336, filed on Apr. 9, 2010, issued as U.S. Pat. No. 8,600,517 on Dec. 3, 2013, which is the U.S. national phase of International Application No. PCT/SE2008/000665, filed on Nov. 27, 2008, which designated the U.S. and claims the benefit of U.S. Provisional Application No. 60/996,601, filed Nov. 27, 2007, the entire contents of each of which are hereby incorporated by reference in this application.

TECHNICAL FIELD

The present invention relates generally to a method and system for supplying wireless energy to a medical device implanted in a patient. In particular, the invention is concerned with controlling the amount of energy transferred from an energy transmitting device placed outside the patient to an energy receiver inside the patient.

BACKGROUND

Medical devices designed to be implanted in a patient's body are typically operated by means of electrical power. Such medical devices include electrical and mechanical stimulators, motors, pumps, etc, which are designed to support or stimulate various body functions. Electrical power can be supplied to such an implanted medical device from a likewise implanted battery or from an external energy transmitter that can supply any needed amount of electrical power intermittently or continuously without requiring repeated surgical operations.

An external energy transmitter can transfer wireless energy to an implanted internal energy receiver located inside the patient and connected to the medical device for supplying received energy thereto. So-called TET (Transcutaneous Energy Transfer) devices are known that can transfer wireless energy in this manner. Thereby, no leads or the like penetrating the skin need to be used for connecting the medical device to an external energy source, such as a battery.

A TET device typically comprises an external energy source, in this application part of an external energy transmitter, including a primary coil adapted to inductively transfer any amount of wireless energy, by inducing voltage in a secondary coil of an internal energy receiver which is implanted preferably just beneath the skin of a patient. The highest transfer efficiency is obtained when the primary coil is positioned close to the skin adjacent to and in alignment with the secondary coil, i.e. when a symmetry axis of the primary coil is parallel to that of the secondary coil.

Typically, the amount of energy required to operate an implanted medical device may vary over time depending on the operational characteristics of the device. For example, the device may be designed to switch on and off at certain intervals, or otherwise change its behavior, in order to provide a suitable electrical or mechanical stimulation, or the like. Such operational variations will naturally result in corresponding variations with respect to the amount of required energy.

Furthermore, the position of the external energy source relative to the implanted internal energy receiver is a factor that affects the efficiency of the energy transfer, which highly depends on the distance and relative angle between the source and the receiver. For example, when primary and secondary coils are used, changes in coil spacing result in a corresponding variation of the induced voltage. During operation of the medical device, the patient's movements will typically change the relative spacing of the external source and the internal receiver arbitrarily such that the transfer efficiency greatly varies.

If the transfer efficiency becomes low, the amount of energy supplied to the medical device may be insufficient for operating the device properly, so that its action must be momentarily stopped, naturally disturbing the intended medical effect of the device.

On the other hand, the energy supplied to the medical device may also increase drastically, if the relative positions of the external source and the internal receiver change in a way that unintentionally increases the transfer efficiency. This situation can cause severe problems since the implant cannot "consume" the suddenly very high amount of supplied energy. Unused excessive energy must be absorbed in some way, resulting in the generation of heat, which is highly undesirable. Hence, if excessive energy is transferred from the external energy source to the internal energy receiver, the temperature of the implant will increase, which may damage the surrounding tissue or otherwise have a negative effect on the body functions. It is generally considered that the temperature in the body should not increase more than three degrees to avoid such problems. Therefore a very efficient transfer system is needed.

It is thus highly desirable to always supply the right amount of energy to an implanted medical device, in order to ensure proper operation and/or to avoid increased temperature. Various methods are known for controlling the amount of transferred energy in response to different conditions in the receiving implant. However, the presently available solutions for controlling the wireless transfer of energy to implanted medical devices are lacking in precision in this respect.

For example, U.S. Pat. No. 5,995,874 discloses a TET system in which the amount of transmitted energy from a primary coil is controlled in response to an indication of measured characteristics of a secondary coil, such as load current and voltage. The transmitted energy can be controlled by varying the current and voltage in the primary coil, transmission frequency or coil dimensions. In particular, a change is effected in the saturation point of the magnetic field between the coils, in order to adjust the power transfer efficiency. However, it is not likely that this solution will work well in practice, since a saturation point in the human tissue would not occur, given the magnetic field levels that are possible to use. Moreover, if the energy transmission must be increased considerably, e.g. to compensate for losses due to variations in alignment and/or spacing between the coils, the relatively high radiation generated may be damaging or unhealthy or unpleasant to the patient, as is well known.

An effective solution is thus needed for accurately controlling the amount of transferred energy to an implanted medical device to ensure proper operation thereof. Moreover, excessive energy transfer resulting in raised temperature at the medical device, and/or power surges should be avoided, in order to avoid tissue damages and other unhealthy or unpleasant consequences for the patient.

SUMMARY OF THE INVENTION

The disclosed invention instead varies the width of the energy pulses with constant frequency and constant amplitude. The pulse width is achieved with a modulation technique, (hereafter PWMT) (in the preferred embodiment many times per second), to control the amount of energy transferred from the external energy transmitting coil in the system to the implanted receiver. The PWMT is used to digitally vary the amount of power from the power amplifier that drives the transmitting coil. Compared to previous analog systems a PWM system is a great deal more efficient and can easily be controlled from a digital domain system such as a microprocessor.

There are several different ways to achieve the PWMT to control the amount of output energy from the power amplifier to the transmitting coil. Generally modulation of the pulse width may be created with a system that controls the power using a continuous square wave pulse signal with a constant frequency where the duty cycle of the pulses are varied or a system that controls power using a continuous square wave pulse train signal with both constant frequency and a constant pulse width and thereby adjusting the duty cycle width of the train of pulses. These two basic techniques as well as most modifications of them can be used to control the output power of the transmitting coil.

The transmission of wireless energy from the external energy transmitting device may be controlled by applying to the external energy transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Thus is provided a method of transmitting wireless energy from an external energy transmitting device placed externally to a human body to an internal energy receiver placed internally in the human body, the method comprising: applying to the external transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Also is provided an apparatus adapted to transmit wireless energy from an external energy transmitting device placed externally to a human body to an internal energy receiver placed internally in the human body, the apparatus comprising, a first electric circuit to supply electrical pulses to the external transmitting device, said electrical pulses having leading and trailing edges, said transmitting device adapted to supply wireless energy, wherein the electrical circuit being adapted to vary the lengths of first time intervals between successive leading and trailing edges of the electrical pulses and/or the lengths of second time intervals between successive trailing and leading edges of the electrical pulses, and wherein the transmitted wireless energy, generated from the electrical pulses having a varied power, the power depending on the lengths of the first and/or second time intervals.

The method and apparatus may be implemented according to different embodiments and features as follows.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. Further, the electrical pulses may also have a substantially constant frequency. The electrical pulses within a pulse train may likewise have a substantially constant frequency.

When applying electrical pulses to the external energy transmitting device, the electrical pulses may generate an electromagnetic field over the external energy source, the electromagnetic field being varied by varying the first and second time intervals, and the electromagnetic field may induce electrical pulses in the internal energy receiver, the induced pulses carrying energy transmitted to the internal energy receiver. The wireless energy is then transmitted in a substantially purely inductive way from the external energy transmitting device to the internal energy receiver.

The electrical pulses may be released from the first electrical circuit with such a frequency and/or time period between leading edges of the consecutive pulses, so that when the lengths of the first and/or second time intervals are varied, the resulting transmitted energy are varied. When applying the electrical pulses, the electrical pulses may have a substantially constant frequency.

The circuit formed by the first electric circuit and the external energy transmitting device may have a first characteristic time period or first time constant, and when effectively varying the transmitted energy, such frequency time period may be in the range of the first characteristic time period or time constant or shorter.

It should be understood that all the embodiments described above mainly as a method could be used both as an apparatus adapted to perform everything described above and also as a method performing the different tasks described above.

Energy Feed Back System to be Used With the Invention

In a preferred embodiment, the wireless energy is transmitted from an external energy transmitting device located outside the patient and is received by an internal energy receiver located inside the patient, the internal energy receiver being connected to the medical device for directly or indirectly supplying received energy thereto. An energy balance is determined between the energy received by the internal energy receiver and the energy used for the medical device, the transmission of wireless energy from the external energy source is then controlled based on the determined energy balance.

An apparatus adapted to control or a method for controlling is also provided for controlling transmission of wireless energy supplied to an electrically operable medical device implanted in a patient. The apparatus is adapted to transmit the wireless energy from an external energy transmitting device located outside the patient which is received by an internal energy receiver located inside the patient, the internal energy receiver being connected to the medical device for directly or indirectly supplying received energy thereto. The apparatus is further adapted to determine an energy balance between the energy received by the internal energy receiver and, the energy used for the medical device, and control the transmission of wireless energy from the external energy source, based on the determined energy balance. The method comprising the steps of transmitting the wireless energy from an external energy transmitting device located outside the patient which is received by an internal energy receiver located inside the patient, the internal energy receiver being connected to the medical device for directly or indirectly supplying received energy thereto. The method is determining an energy balance between the energy received by the internal energy receiver and the energy used for the medical device, and control the transmission of wireless energy from the external energy source, based on the determined energy balance.

The method controlling and the apparatus adapted to control may be implemented according to different embodiments and features as follows:

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

In one alternative, substantially all energy used for the medical device is consumed (e.g. by the consuming part 200a of FIG. 2) to operate the medical device. In that case, the energy may be consumed after being stabilized in at least one energy stabilizing unit of the medical device.

In another alternative, substantially all energy used for the medical device is stored in the at least one energy storage device. In yet another alternative, the energy used for the medical device is partly consumed to operate the medical device and partly stored in the at least one energy storage device.

The energy received by the internal energy receiver may be stabilized by a capacitor, before the energy is supplied directly or indirectly to the medical device.

The difference between the total amount of energy received by the internal energy receiver and the total amount of consumed and/or stored energy may be directly or indirectly measured over time, and the energy balance can then be determined based on a detected change in the total amount difference.

The energy received by the internal energy receiver may further be accumulated and stabilized in an energy stabilizing unit, before the energy is supplied to the medical device. In that case, the energy balance may be determined based on a detected change followed over time in the amount of consumed and/or stored energy. Further, the change in the amount of consumed and/or stored energy may be detected by determining over time the derivative of a measured electrical parameter related to the amount of consumed and/or stored energy, where the derivative at a first given moment is corresponding to the rate of the change at the first given moment, wherein the rate of change includes the direction and speed of the change. The derivative may further be determined based on a detected rate of change of the electrical parameter.

The energy received by the internal energy receiver may be supplied to the medical device with at least one constant voltage, wherein the constant voltage is created by a constant voltage circuitry. In that case, the energy may be supplied with at least two different voltages, including the at least one constant voltage.

The energy received by the internal energy receiver may also be supplied to the medical device with at least one constant current, wherein the constant current is created by a constant current circuitry. In that case, the energy may be supplied with at least two different currents including the at least one constant current.

The energy balance may also be determined based on a detected difference between the total amount of energy received by the internal energy receiver and the total amount of consumed and/or stored energy, the detected difference being related to the integral over time of at least one measured electrical parameter related to the energy balance. In that case, values of the electrical parameter may be plotted over time as a graph in a parameter-time diagram, and the integral can be determined from the size of the area beneath the plotted graph. The integral of the electrical parameter may relate to the energy balance as an accumulated difference between the total amount of energy received by the internal energy receiver and the total amount of consumed and/or stored energy.

The energy storage device in the medical device may include at least one of: a rechargeable battery, an accumulator or a capacitor. The energy stabilizing unit may include at least one of: an accumulator, a capacitor or a semiconductor adapted to stabilize the received energy.

When the energy received by the internal energy receiver is accumulated and stabilized in an energy stabilizing unit before energy is supplied to the medical device and/or energy storage device, the energy may be supplied to the medical device and/or energy storage device with at least one constant voltage, as maintained by a constant voltage circuitry. In that case, the medical device and energy storage device may be supplied with two different voltages, wherein at least one voltage is constant, maintained by the constant voltage circuitry.

Alternatively, when the energy received by the internal energy receiver is accumulated and stabilized in an energy stabilizing unit before energy is supplied to the medical device and/or energy storage device, the energy may be supplied to the medical device and/or energy storage device with at least one constant current, as maintained by a constant current circuitry. In that case, the medical device and energy storage device may be supplied with two different currents wherein at least one current is constant, maintained by the constant current circuitry.

The wireless energy may be initially transmitted according to a predetermined energy consumption plus storage rate. In that case, the transmission of wireless energy may be turned off when a predetermined total amount of energy has been transmitted. The energy received by the internal energy receiver may then also be accumulated and stabilized in an energy stabilizing unit before being consumed to operate the medical device and/or stored in the energy storage device until a predetermined total amount of energy has been consumed and/or stored.

Further, the wireless energy may be first transmitted with the predetermined energy rate, and then transmitted based on the energy balance which can be determined by detecting the total amount of accumulated energy in the energy stabilizing unit. Alternatively, the energy balance can be determined by detecting a change in the current amount of accumulated energy in the energy stabilizing unit. In yet another alternative, the energy balance, can be determined by detecting the direction and rate of change in the current amount of accumulated energy in the energy stabilizing unit.

The transmission of wireless energy may be controlled such that an energy reception rate in the internal energy receiver corresponds to the energy consumption and/or storage rate. In that case, the transmission of wireless energy may be turned off when a predetermined total amount of energy has been consumed.

The energy received by the internal energy receiver may be first accumulated and stabilized in an energy stabilizing unit, and then consumed or stored by the medical device until a predetermined total amount of energy has been consumed. In that case, the energy balance may be determined based on a detected total amount of accumulated energy in the energy stabilizing unit. Alternatively, the energy balance may be determined by detecting a change in the current amount of accumulated energy in the energy stabilizing unit. In yet another alternative, the energy balance may be determined by detecting the direction and rate of change in the current amount of accumulated energy in the energy stabilizing unit.

One Embodiment of an Apparatus or Method to be Used with the Energy Control System An apparatus adapted to perform or a method for controlling the flow of fluids and/or other bodily matter in lumens formed by tissue walls of bodily organs are provided so as to at least substantially or even completely eliminate the injured tissue wall problems that have resulted from implanted prior art devices that constrict such bodily organs.

In accordance with one embodiment of the present invention, there is provided an apparatus or method wherein the apparatus comprises an implantable constriction device for gently constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

This embodiment provides an advantageous combination of constriction and stimulation devices, which results in a two-stage influence on the flow of fluids and/or other bodily matter in the lumen of a bodily organ. Thus, the constriction device may gently constrict the tissue wall by applying a relatively weak force against the wall portion, and the stimulation device may stimulate the constricted wall portion to achieve the desired final influence on the flow in the lumen. The phrase "gently constricting a portion of the tissue wall" is to be understood as constricting the wall portion without substantially hampering the blood circulation in the tissue wall.

Preferably, the stimulation device is adapted to stimulate different areas of the wall portion as the constriction device constricts the wall portion, and the control device controls the stimulation device to intermittently and individually stimulate the areas of the wall portion. This intermittent and individual stimulation of different areas of the wall portion of the organ allows tissue of the wall portion to maintain substantially normal blood circulation during the operation of the apparatus of the invention.

The combination of the constriction and stimulation devices enables application of the apparatus or method of the invention at any place on any kind of bodily organs, in particular, but not limited to, tubular bodily organs, which is a significant advance in the art, as compared with prior stimulation devices that are confined to electric stimulation of malfunctioning sphincters.

In some applications using the present invention, there will be daily adjustments of an implanted constriction device. Therefore, in a preferred embodiment of the invention, the constriction device is adjustable to enable adjustment of the constriction of the wall portion as desired, wherein the control device controls the constriction device to adjust the constriction of the wall portion. The control device may control the constriction and stimulation devices independently of each other, and simultaneously. Optionally, the control device may control the stimulation device to stimulate, or to not stimulate the wall portion while the control device controls the constriction device to change the constriction of the wall portion.

Initially, the constriction device may be calibrated by using the control device to control the stimulation device to stimulate the wall portion, while controlling the constriction device to adjust the constriction of the wall portion until the desired restriction of the flow in the lumen is obtained.

Flow Restriction

The apparatus or method of the above described embodiment is well suited for restricting the flow of fluids and/or other bodily matter in the lumen of a bodily organ. Thus, in a principal embodiment of the invention, the constriction device is adapted to constrict the wall portion to at least restrict the flow in the lumen, and the control device controls the stimulation device to cause contraction of the constricted wall portion, so that the flow in the lumen is at least further restricted. Specifically, the constriction device is adapted to constrict the wall portion to a constricted state in which the blood circulation in the constricted wall portion is substantially unrestricted and the flow in the lumen is at least restricted, and the control device controls the stimulation device to cause contraction of the wall portion, so that the flow in the lumen is at least further restricted when the wall portion is kept by the constriction device in the constricted state.

The constriction and stimulation devices may be controlled to constrict and stimulate, respectively, to an extent that depends on the flow restriction that is desired to be achieved in a specific application of the apparatus of the invention. Thus, in accordance with a first flow restriction option, the control device controls the constriction device to constrict the wall portion, such that flow in the lumen is restricted or stopped, and controls the stimulation device to stimulate the constricted wall portion to cause contraction thereof, such that flow in the lumen is further restricted or more safely stopped. More precisely, the control device may control the stimulation device in a first mode to stimulate the constricted wall portion to further restrict or stop the flow in the lumen and to: a) control the stimulation device in a second mode to cease the stimulation of the wall portion to increase the flow in the lumen; or b) control the stimulation and constriction devices in the second mode to cease the stimulation of the wall portion and release the wall portion to restore the flow in the lumen.

Movement of Fluid and/or Other Bodily Matter in Lumen

In one embodiment the constriction device is adapted to constrict the wall portion to restrict or vary the flow in the lumen, and the control device controls the stimulation device to progressively stimulate the constricted wall portion, in the downstream or upstream direction of the lumen, to cause progressive contraction of the wall portion to move the fluid and/or other bodily matter in the lumen.

Stimulation

The control device may control the stimulation device to stimulate one or more of the areas of the wall portion at a time, for example by sequentially stimulating the different areas. Furthermore, the control device may control the stimulation device to cyclically propagate the stimulation of the areas along the wall portion, preferably in accordance with a determined stimulation pattern. To achieve the desired reaction of the tissue wall during the stimulation thereof, the control device may control the stimulation device to, preferably cyclically, vary the intensity of the stimulation of the wall portion.

In a preferred embodiment of the invention, the control device controls the stimulation device to intermittently stimulate the areas of the wall portion with pulses that preferably form pulse trains. At least a first area and a second area of the areas of the wall portion may be repeatedly stimulated with a first pulse train and a second pulse train, respectively, such that the first and second pulse trains over time are shifted relative to each other. For example, the first area may be stimulated with the first pulse train, while the second area is not stimulated with said second pulse train, and vice versa. Alternatively, the first and second pulse trains may be shifted relative to each other, such that the first and second pulse trains at least partially overlap each other.

The pulse trains can be configured in many different ways. Thus, the control device may control the stimulation device to vary the amplitudes of the pulses of the pulse trains, the duty cycle of the individual pulses of each pulse train, the width of each pulse of the pulse trains, the length of each pulse train, the repetition frequency of the pulses of the pulse trains, the repetition frequency of the pulse trains, the number of pulses of each pulse train, and/or the off time periods between the pulse trains. Several pulse trains of different configurations may be employed to achieve the desired effect.

In case the control device controls the stimulation device to vary the off time periods between pulse trains that stimulate the respective area of the wall portion, it is also possible to control each off time period between pulse trains to last long enough to restore substantially normal blood circulation in the area when the latter is not stimulated during the off time periods.

An electric stimulation device suitably comprises at least one, preferably a plurality of electrical elements, such as electrodes, for engaging and stimulating the wall portion with electric pulses. Optionally, the electrical elements may be placed in a fixed orientation relative to one another. The control device controls the electric stimulation device to electrically energize the electrical elements, one at a time, or groups of electrical elements at a time. Preferably, the control device controls the electric stimulation device to cyclically energize each element with electric pulses. Optionally, the control device may control the stimulation device to energize the electrical elements, such that the electrical elements are energized one at a time in sequence, or such that a number or groups of the electrical elements are energized at the same time. Also, groups of electrical elements may be sequentially energized, either randomly or in accordance with a predetermined pattern.

The electrical elements may form any pattern of electrical elements. Preferably, the electrical elements form an elongate pattern of electrical elements, wherein the electrical elements are applicable on the patient's wall of the organ, such that the elongate pattern of electrical elements extends lengthwise along the wall of the organ, and the elements abut the respective areas of the wall portion. The elongate pattern of electrical elements may include one or more rows of electrical elements extending lengthwise along the wall of the organ. Each row of electrical elements may form a straight, helical or zig-zag path of electrical elements, or any form of path. The control device may control the stimulation device to successively energize the electrical elements longitudinally along the elongate pattern of electrical elements in a direction opposite to, or in the same direction as that of, the flow in the patient's lumen.

In accordance with a preferred embodiment of the invention, the electrical elements form a plurality of groups of elements, wherein the groups form a series of groups extending along the patient's organ in the flow direction in the patient's lumen. The electrical elements of each group of electrical elements may form a path of elements extending at least in part around the patient's organ. In a first alternative, the electrical elements of each group of electrical elements may form more than two paths of elements extending on different sides of the patient's organ, preferably substantially transverse to the flow direction in the patient's lumen. The control device may control the stimulation device to energize the groups of electrical elements in the series of groups in random, or in accordance with a predetermined pattern. Alternatively, the control device may control the stimulation device to successively energize the groups of electrical elements in the series of groups in a direction opposite to, or in the same direction as that of, the flow in the patient's lumen, or in both said directions starting from a position substantially at the center of the constricted wall portion. For example, groups of energized electrical elements may form advancing waves of energized electrical elements, as described above; that is, the control device may control the stimulation device to energize the groups of electrical elements, such that energized electrical elements form two waves of energized electrical elements that simultaneously advance from the center of the constricted wall portion in two opposite directions towards both ends of the elongate pattern of electrical elements.

Mechanical Operation

Where the operation device mechanically operates the constriction device of the constriction/stimulation unit, it may be non-inflatable. Furthermore, the operation device may comprise a servo system, which may include a gearbox. The term "servo system" encompasses the normal definition of a servo mechanism, i.e., an automatic device that controls large amounts of power by means of very small amounts of power, but may alternatively or additionally encompass the definition of a mechanism that transfers a weak force acting on a moving element having a long stroke into a strong force acting on another moving element having a short stroke. Preferably, the operation device operates the constriction device in a non-magnetic and/or non-manual manner. A motor may be operatively connected to the operation device. The operation device may be operable to perform at least one reversible function and the motor may be capable of reversing the function.

Hydraulic Operation

Where the operation device hydraulically operates the constriction device of the constriction/stimulation unit, it includes hydraulic means for adjusting the constriction device.

In an embodiment of the invention, the hydraulic means comprises a reservoir and an expandable/contractible cavity in the constriction device, wherein the operation device distributes hydraulic fluid from the reservoir to expand the cavity, and distributes hydraulic fluid from the cavity to the reservoir to contract the cavity. The cavity may be defined by a balloon of the constriction device that abuts the tissue wall portion of the patient's organ, so that the patient's wall portion is constricted upon expansion of the cavity and released upon contraction of the cavity.

Alternatively, the cavity may be defined by a bellows that displaces a relatively large contraction element of the constriction device, for example a large balloon that abuts the wall portion, so that the patient's wall portion is constricted upon contraction of the bellows and released upon expansion of the bellows. Thus, a relatively small addition of hydraulic fluid to the bellows causes a relatively large increase in the constriction of the wall portion. Such a bellows may also be replaced by a suitably designed piston/cylinder mechanism.

Where the hydraulic means comprises a cavity in the constriction device, the apparatus of the invention can be designed in accordance with the options listed below.

1) The reservoir comprises first and second wall portions, and the operation device displaces the first and second wall portions relative to each other to change the volume of the reservoir, such that fluid is distributed from the reservoir to the cavity, or from the cavity to the reservoir. 1a) The first and second wall portions of the reservoir are displaceable relative to each other by at least one of a magnetic device, a hydraulic device or an electric control device. 2) The apparatus comprises a fluid conduit between the reservoir and the cavity, wherein the reservoir forms part of the conduit. The conduit and reservoir and apparatus are devoid of any non-return valve. The reservoir forms a fluid chamber with a variable volume, and distributes fluid from the chamber to the cavity by a reduction in the volume of the chamber and withdraws fluid from the cavity by an expansion of the volume of the chamber. The apparatus further comprises a motor for driving the reservoir, comprising a movable wall of the reservoir for changing the volume of the chamber.

In a special embodiment of the invention, the operation device comprises a reverse servo operatively connected to the hydraulic means. The term "reverse servo" is to be understood as a mechanism that transfers a strong force acting on a moving element having a short stroke into a weak force acting on another moving element having a long stroke; i.e., the reverse function of a normal servo mechanism. Thus, minor changes in the amount of fluid in a smaller reservoir could be transferred by the reverse servo into major changes in the amount of fluid in a larger reservoir. The reverse servo is particularly suited for manual operation thereof.

Design of Control Device

The control device suitably controls the constriction/stimulation unit from outside the patient's body. Preferably, the control device is operable by the patient. For example, the control device may comprise a manually operable switch for switching on and off the constriction/stimulation unit, wherein the switch is adapted for subcutaneous implantation in the patient to be manually or magnetically operated from outside the patient's body. Alternatively, the control device may comprise a hand-held wireless remote control, which is conveniently operable by the patient to switch on and off the constriction/stimulation unit. The wireless remote control may also be designed for application on the patient's body like a wristwatch. Such a wristwatch type of remote control may emit a control signal that follows the patient's body to implanted signal responsive means of the apparatus.

BRIEF DESCRIPTION OF THE DRAWINGS

The present invention will now be described in more detail and with reference to the accompanying drawings, in which:

FIGS. 3b-3i are block diagrams of alternative arrangements for transmitting energy wirelessly to an implant in a human body.

FIGS. 5c-5l are graphs showing different waveforms of signals in the triangle wave generator and the PWMT amplifier.

FIGS. 6b-6f are graphs showing different waveforms of signals in the PWMT amplifier of the second embodiment.

FIGS. 7b-7j are graphs showing different waveforms of signals in the PWMT amplifier of the second embodiment.

FIGS. 8b' and 8b" is a circuit diagram showing further another embodiment of a PWMT amplifier.

FIGS. 8c-d are graphs showing different waveforms of signals in the PWMT amplifier of the ultrasonic embodiment.

FIGS. 9f-9h illustrate different states of operation of a modification of the general embodiment.

FIGS. 9i-9k illustrate an alternative mode of operation of the modification of the general embodiment.

FIGS. 14-22 are diagrams illustrating various measurements obtained when implementing the inventive method and apparatus according to the circuit diagram of FIG. 13.

DETAILED DESCRIPTION OF PREFERRED EMBODIMENTS

Briefly described, wireless energy is transmitted from an external energy transmitting device located outside a patient and is received by an internal energy receiver located inside the patient. The internal energy receiver is connected to an electrically operable medical device implanted in the patient, for directly or indirectly supplying received energy to the medical device. An energy balance is determined between the energy received by the internal energy receiver and the energy used for the medical device, and the transmission of wireless energy is then controlled based on the determined energy balance. The energy balance thus provides an accurate indication of the correct amount of energy needed, which is sufficient to operate the medical device properly, but without causing undue temperature rise.

Figure 1:
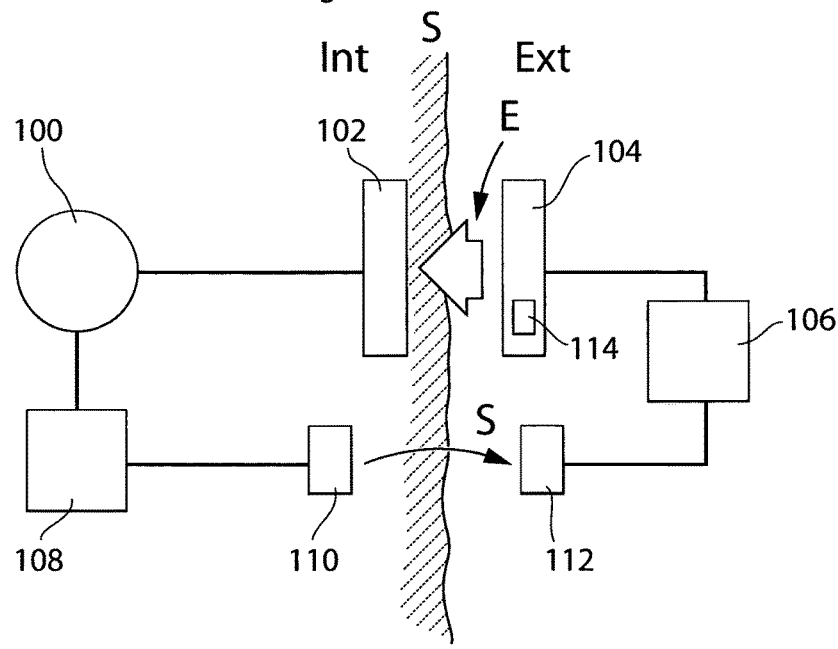
FIG. 1 is a schematic block diagram illustrating an arrangement for supplying an accurate amount of energy to an electrically operable medical device.

In FIG. 1, an arrangement is schematically illustrated for supplying an accurate amount of energy to an electrically operable medical device 100 implanted in a patient, whose skin is indicated by a vertical line S separating the interior "Int" of the patient from the exterior "Ext". The medical device 100 is connected to an internal energy receiver 102, likewise located inside the patient, preferably just beneath the skin S. Generally speaking, the energy receiver 102 may be placed in the abdomen, thorax, muscle fascia (e.g. in the abdominal wall), subcutaneously, or at any other suitable location. The energy receiver 102 is adapted to receive wireless energy E transmitted from an external energy source 104 located outside the skin S in the vicinity of the energy receiver 102.

As is well-known in the art, the wireless energy E may generally be transferred by means of any suitable TET device, such as a device including a primary coil arranged in the energy source 104 and an adjacent secondary coil arranged in the energy receiver 102. When an electric current is fed through the primary coil, energy in the form of a voltage is induced in the secondary coil which can be used to operate a medical device, e.g. after storing the incoming energy in an energy storing device or accumulator, such as a battery or a capacitor. However, the present invention is generally not limited to any particular energy transfer technique, TET devices or energy storing devices. Any kind of wireless energy may be used.

The amount of transferred energy can be regulated by means of an external control unit 106 controlling the energy source 104 based on the determined energy balance, as described above. In order to transfer the correct amount of energy, the energy balance can be determined by means of an internal control unit 108 connected to the medical device 100. The control unit 108 may thus be arranged to receive various measurements obtained by suitable sensors or the like, not shown, measuring certain characteristics of the medical device 100, somehow reflecting the required amount of energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by, e.g., body temperature, blood pressure, heartbeats and breathing.

Furthermore, an energy storing device or accumulator, not shown here, may also be connected to the energy receiver 102 for accumulating received energy for later use by the medical device 100. Alternatively or additionally, characteristics of such an energy storing device, also reflecting the required amount of energy, may be measured as well. The energy storing device may be a battery, and the measured characteristics may be related to the current state of the battery, such as voltage, temperature, etc. In order to provide sufficient voltage and current to the medical device 100, and also to avoid excessive heating, it is clearly understood that the battery should be charged optimally by receiving a correct amount of energy from the energy receiver 102, i.e. not too little or too much. The energy storing device may also be a capacitor with corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 108 is adapted to determine the energy balance or the currently required amount of energy, (either energy per time unit or accumulated energy) based on measurements made by the above-mentioned sensors or measuring devices on the medical device 100, or the patient, or an energy storing device if used, or any combination thereof. The internal control unit 108 is further connected to an internal signal transmitter 110, arranged to transmit a control signal reflecting the determined required amount of energy, to an external signal receiver 112 connected to the external control unit 106. The amount of energy transmitted from the energy source 104 may then be regulated in response to the received control signal.

Alternatively, sensor measurements can be transmitted directly to the external control unit 106 wherein the energy balance or the currently required amount of energy can be determined by the external control unit 106, thus integrating the above-described function of the internal control unit 108 in the external control unit 106. In that case, the internal control unit 108 can be omitted and the sensor measurements are supplied directly to the signal transmitter 110 which sends the measurements over to the receiver 112 and the external control unit 106. The energy balance and the currently required amount of energy can then be determined by the external control unit 106 based on those sensor measurements.

However, it is important to understand that this energy feed back system is so much more efficient than the old systems because it is not sending feed back related to any specific parameter instead it is the real use of energy that is compared to the received energy, either the amount of energy received and used, the energy difference, or the energy receiving rate compared to the energy rate used by the medical implant. The implant may use the energy either for consumption or for storing energy in any energy storage device. All the different parameters discussed above would only be used if relevant and needed and only as a tool for determining the real energy balance. However, such parameters may pay an important rule for other actions taken internally by the medical device.

The internal signal transmitter 110 and the external signal receiver 112 may be implemented as separate units using suitable signal transfer means, such as radio, IR (Infrared) or ultrasonic signals. Alternatively, the signal transmitter 110 and the signal receiver 112 may be integrated in the internal energy receiver 102 and the energy source 104, respectively, so as to convey control signals in a reverse direction relative to the energy transfer, basically using the same transmission technique. Such a signal may be frequency, phase or amplitude modulated.

To conclude, the energy supply arrangement illustrated in FIG. 1 may operate basically in the following manner. The energy balance is first determined by the internal control unit 108. A control signal S reflecting the required amount of energy is also created by the internal control unit 108, and the control signal S is transmitted from the signal transmitter 110 to the signal receiver 112. Alternatively, the energy balance can be determined by the external control unit 106 instead depending on the implementation, as mentioned above. In that case, the control signal S may carry measurement results from various sensors. The amount of energy emitted from the energy source 104 can then be regulated by the external control unit 106, based on the determined energy balance, e.g. in response to the received control signal S. This process may be repeated intermittently at certain intervals during ongoing energy transfer, or may be executed on a more or less continuous basis during the energy transfer.

The amount of transferred energy can generally be regulated by using a PWMT in the energy source 104, such as voltage, current, amplitude, wave frequency and pulse characteristics.

Figure 2:
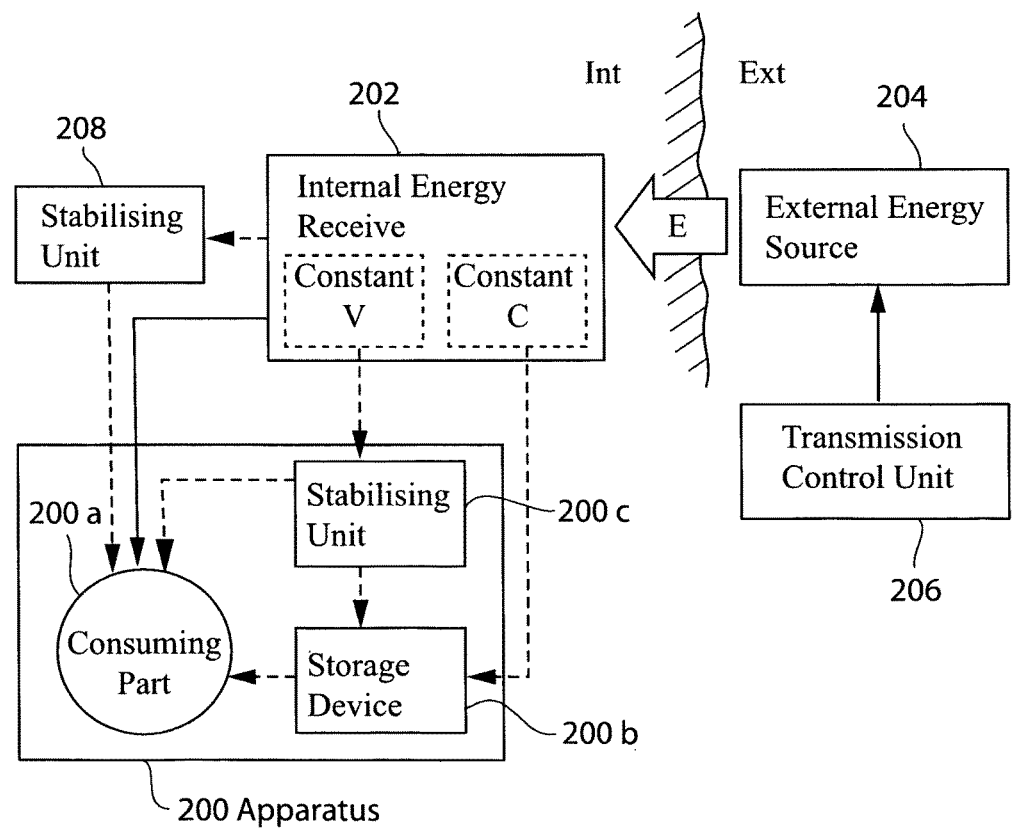
FIG. 2 is a more detailed block diagram of an apparatus for controlling transmission of wireless energy supplied to an electrically operable medical device implanted in a patient.

FIG. 2 illustrates different embodiments for how received energy can be supplied to and used by a medical device 200. Similar to the example of FIG. 1, an internal energy receiver 202 receives wireless energy E from an external energy source 204 which is controlled by a transmission control unit 206. The internal energy receiver 202 may comprise a constant voltage circuit, indicated as a dashed box "constant V" in the figure, for supplying energy at constant voltage to the medical device 200. The internal energy receiver 202 may further comprise a constant current circuit, indicated as a dashed box "constant C" in the figure, for supplying energy at constant current to the medical device 200.

The medical device 200 comprises an energy consuming part 200a which may be a motor, pump, restriction device, or any other medical appliance that requires energy for its electrical operation. The medical device 200 may further comprise an energy storage device 200b for storing energy supplied from the internal energy receiver 202. Thus, the supplied energy may be directly consumed by the energy consuming part 200a or stored by the energy storage device 200b, or the supplied energy may be partly consumed and partly stored. The medical device 200 may further comprise an energy stabilizing unit 200c for stabilizing the energy supplied from the internal energy receiver 202. Thus, the energy may be supplied in a fluctuating manner such that it may be necessary to stabilize the energy before consumed or stored.

The energy supplied from the internal energy receiver 202 may further be accumulated and/or stabilized by a separate energy stabilizing unit 208 located outside the medical device 200, before being consumed and/or stored by the medical device 200. Alternatively, the energy stabilizing unit 208 may be integrated in the internal energy receiver 202. In either case, the energy stabilizing unit 208 may comprise a constant voltage circuit and/or a constant current circuit.

The energy supplied from the internal energy receiver 202 may further be accumulated and/or stabilized by a separate energy stabilizing unit 208 located outside the medical device 200, before being consumed and/or stored by the medical device 200. Alternatively, the energy stabilizing unit 208 may be integrated in the internal energy receiver 202. In either case, the energy stabilizing unit 208 may comprise a constant voltage circuit and/or a constant current circuit.

Figure 3A:
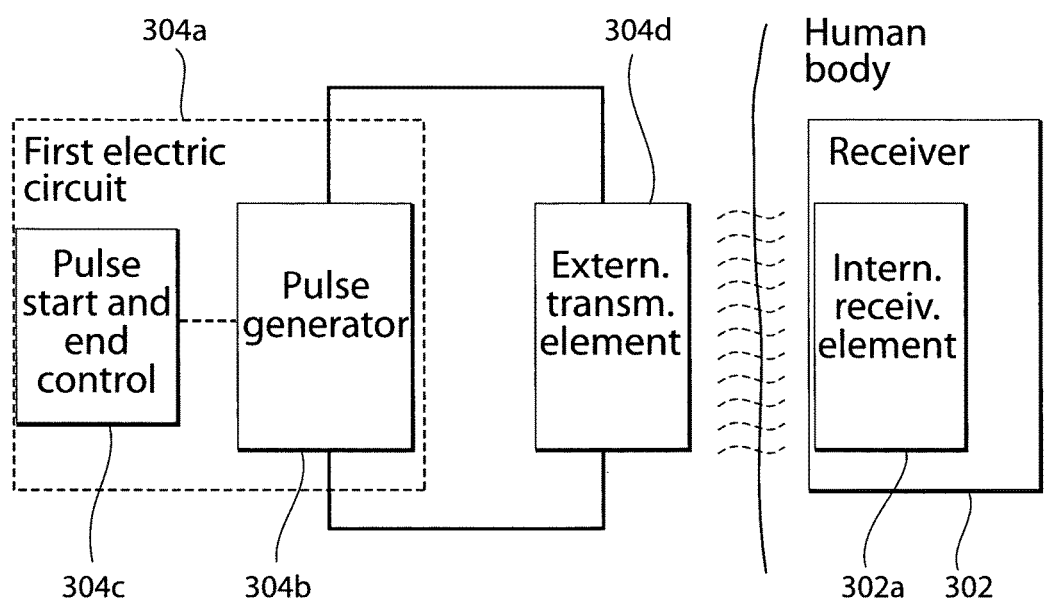
FIG. 3a is a block diagram of an arrangement for transmitting energy wirelessly to an implant in a human body.

FIG. 3a shows a first embodiment of an arrangement for transmitting energy wirelessly to an implant. The arrangement comprises an internal energy receiver 302 and an external energy source 304. Further, the internal energy receiver 302 comprises an internal receiving element 302a. The external energy source comprises a first electric circuit 304a; which comprises a pulse generator 304b and a pulse start and end control unit 304c; and an external transmitting element 304d.

Figure 3B:
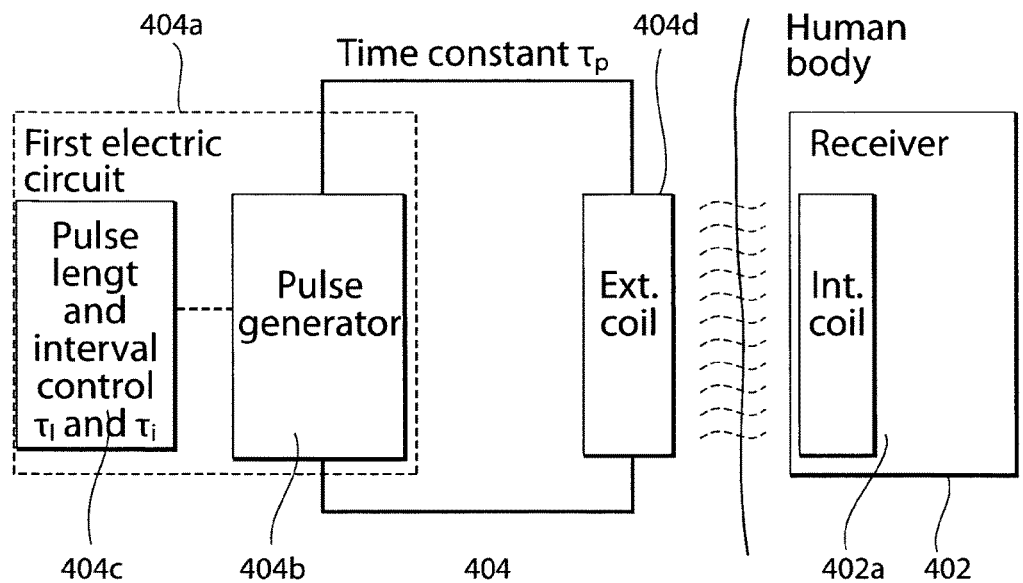

FIG. 3b shows a second embodiment of an arrangement for transmitting energy wirelessly to an implant. The arrangement comprises an internal energy receiver 402 and an external energy source 404. Further, the internal energy receiver 402 comprises an internal receiving coil 402a. The external energy source comprises a first electric circuit 404a; which comprises a pulse generator 404b and a pulse length and interval control unit 404c; and an external transmitting coil 404d.

Figure 3C:
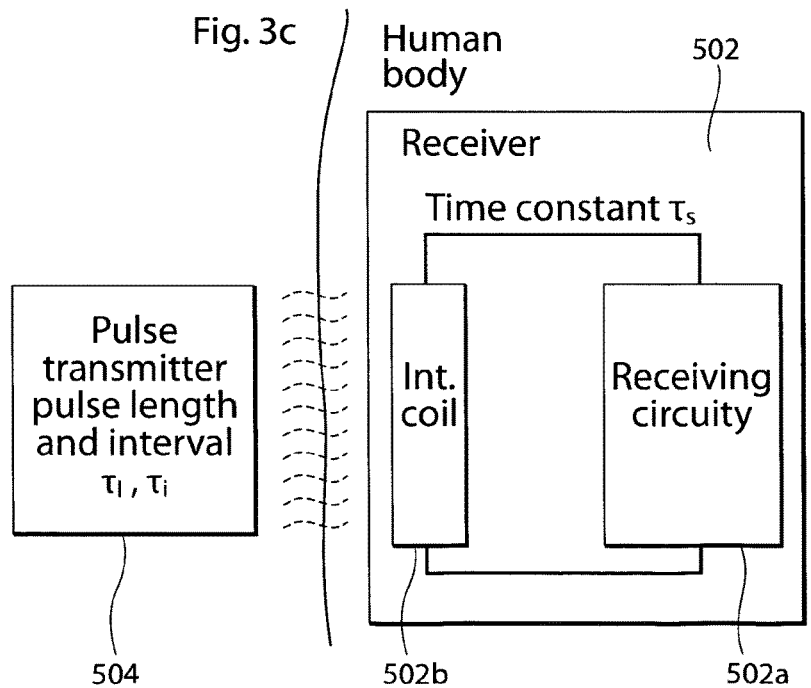

FIG. 3c shows a third embodiment of an arrangement for transmitting energy wirelessly to an implant. The arrangement comprises an internal energy receiver 502 and an external energy source 504. Further, the internal energy receiver 502 comprises a receiving circuitry 502a and an internal receiving coil 502b.

Figure 3D:
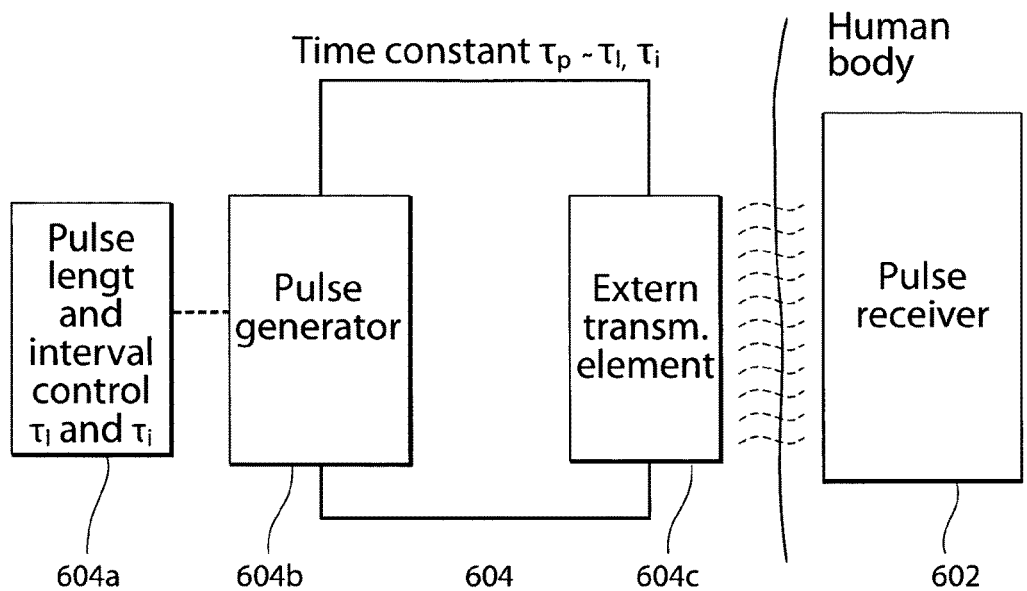

FIG. 3d shows a fourth embodiment of an arrangement for transmitting energy wirelessly to an implant. The arrangement comprises an internal energy receiver 602 and an external energy source 604. Further, the external energy source 604 comprises a pulse length and interval control unit 604a, a pulse generator 604b, and an external transmitting element 604c.

Figure 3E:
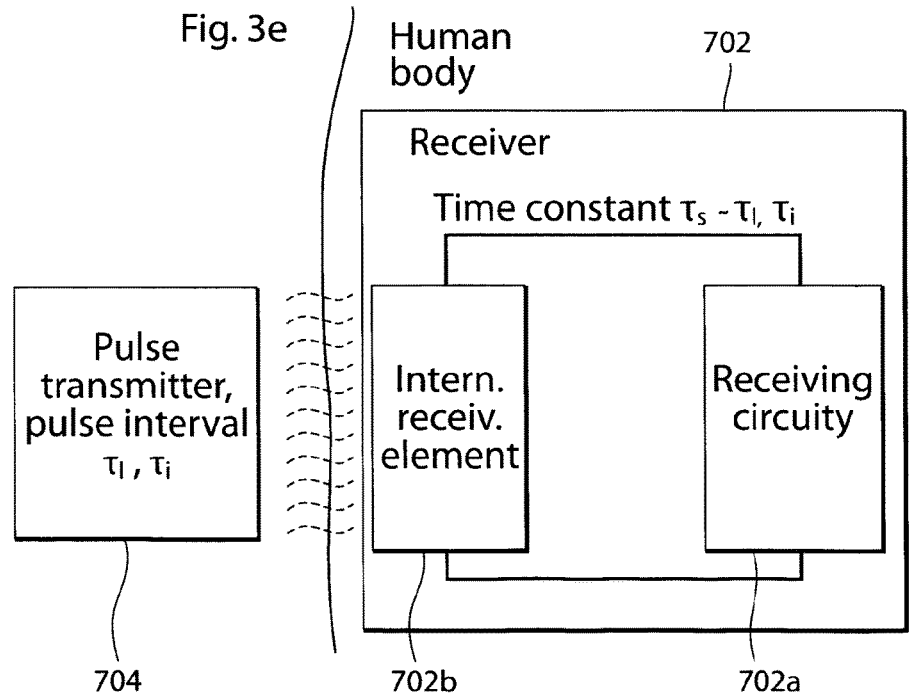

FIG. 3e shows a fifth embodiment of an arrangement for transmitting energy wirelessly to an implant. The arrangement comprises an internal energy receiver 702 and an external energy source 704. Further, the internal energy receiver 702 comprises a receiving circuitry 702a and an internal receiving element 702b.

FIG. 3f shows a sixth embodiment of an arrangement for transmitting energy wirelessly to an implant. The arrangement comprises an internal energy receiver 802 and an external energy source 804. Further, the external energy source 804 comprises a pulse length and interval control unit 804a, a pulse generator 804b, and an external transmitting element 804c.

FIG. 3g shows a seventh embodiment of an arrangement for transmitting energy wirelessly to an implant. The arrangement comprises an internal energy receiver 902 and an external energy source 904. Further, the external energy source 904 comprises a pulse length and interval control unit 904a, a pulse generator 904b, and an external transmitting element 904c. Furthermore, the internal energy receiver 902 comprises a receiving circuitry 902a and an internal receiving element 902b.

Figure 3H:
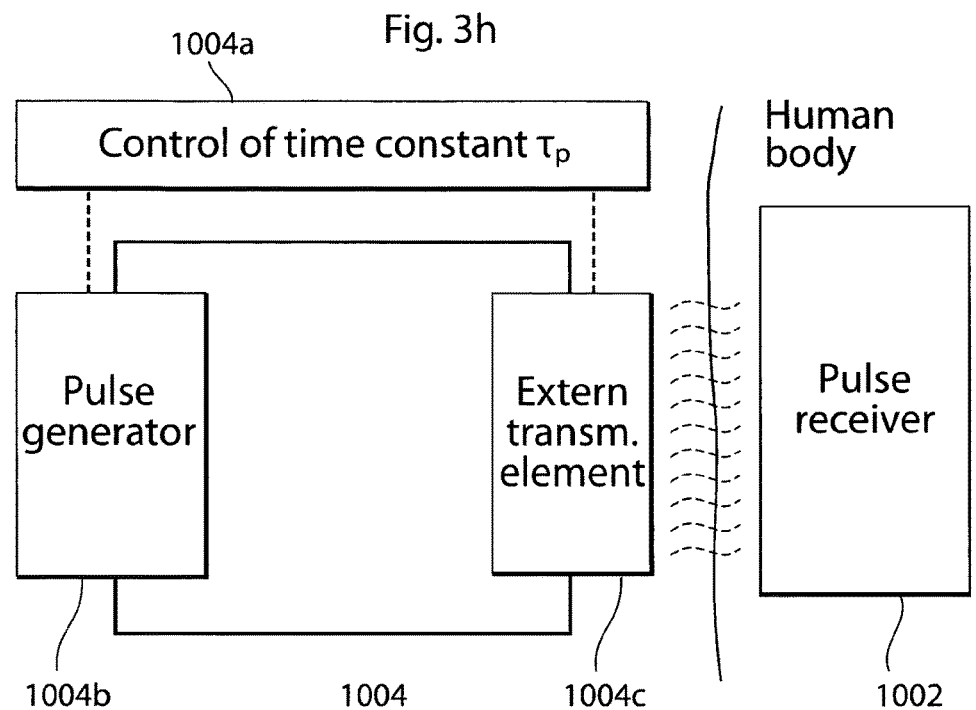

FIG. 3h shows an eight embodiment of an arrangement for transmitting energy wirelessly to an implant. The arrangement comprises an internal energy receiver 1002 and an external energy source 1004. Further, the external energy source 1004 comprises a time constant control unit 1004a, a pulse generator 1004b, and an external transmitting element 1004c.

Figure 3I:
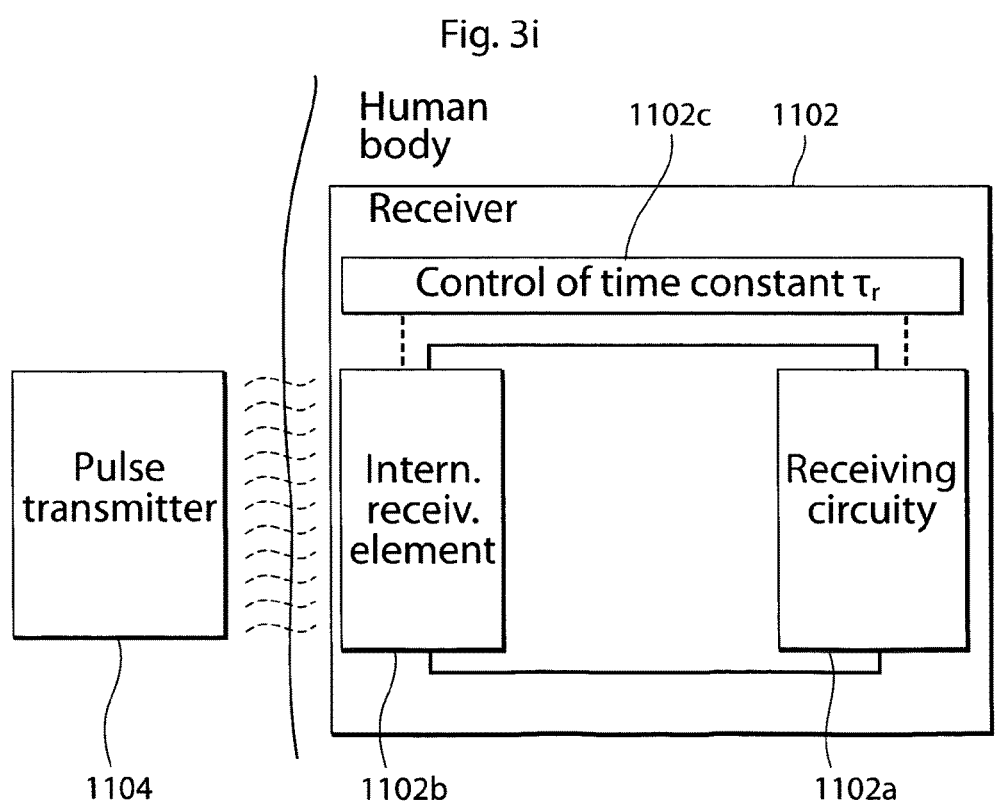

FIG. 3i shows a ninth embodiment of an arrangement for transmitting energy wirelessly to an implant. The arrangement comprises an internal energy receiver 1102 and an external energy source 1104. Further, the internal energy receiver 1102 comprises a receiving circuitry 1102a, an internal receiving element 1102b, and a time constant control unit 1102c.

Figure 4A:
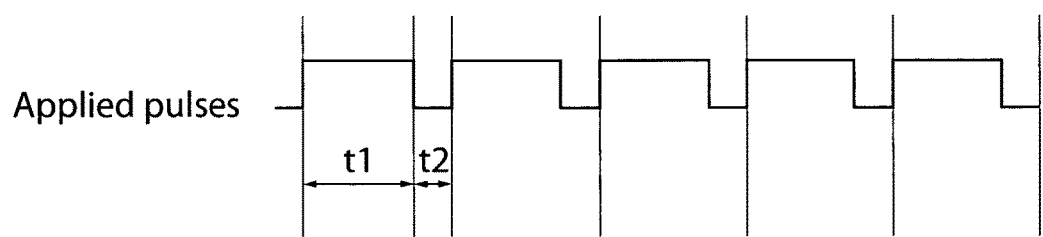
FIG. 4a is a diagram showing an example of pulses to be modified.

FIG. 4a shows an example of transmitted pulses, according to a first embodiment of the present invention. The pulses have a constant frequency and amplitude. However, the relation between the times t1 and t2 varies.

Figure 4B:
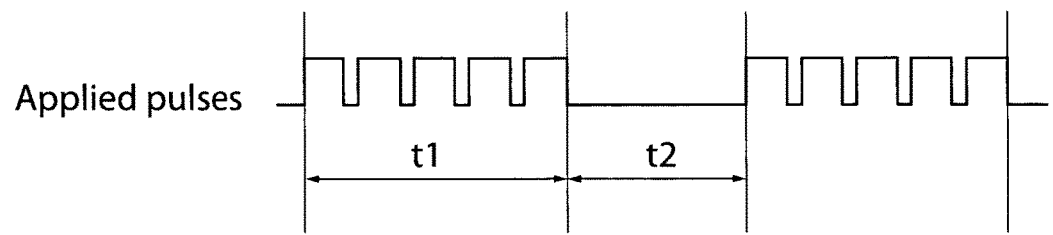
FIG. 4b is a diagram showing an example of a pulse train to be modified.
Figure 5A:
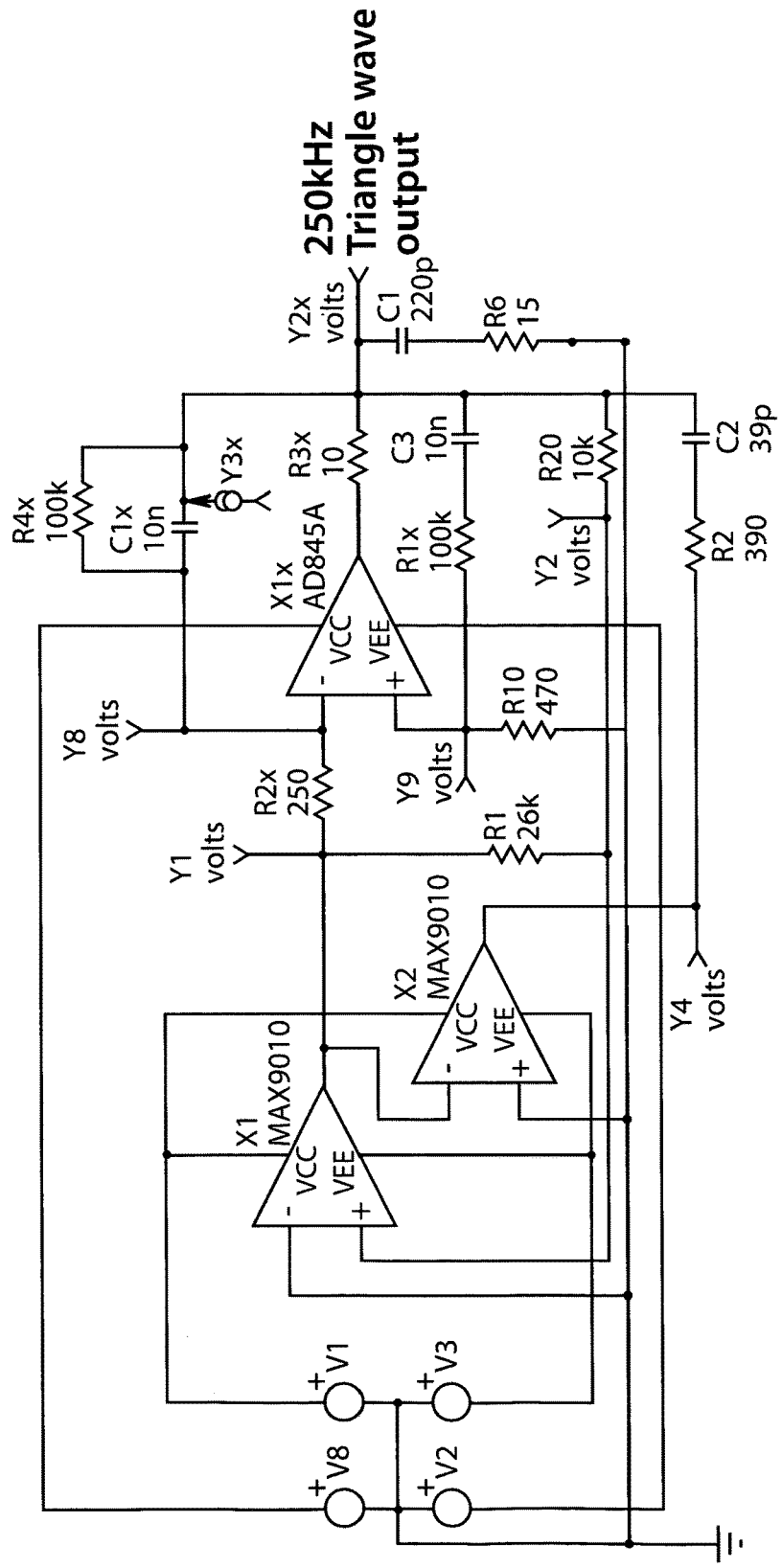
FIG. 5a is a circuit diagram showing the triangle wave generator.
Figure 5B:
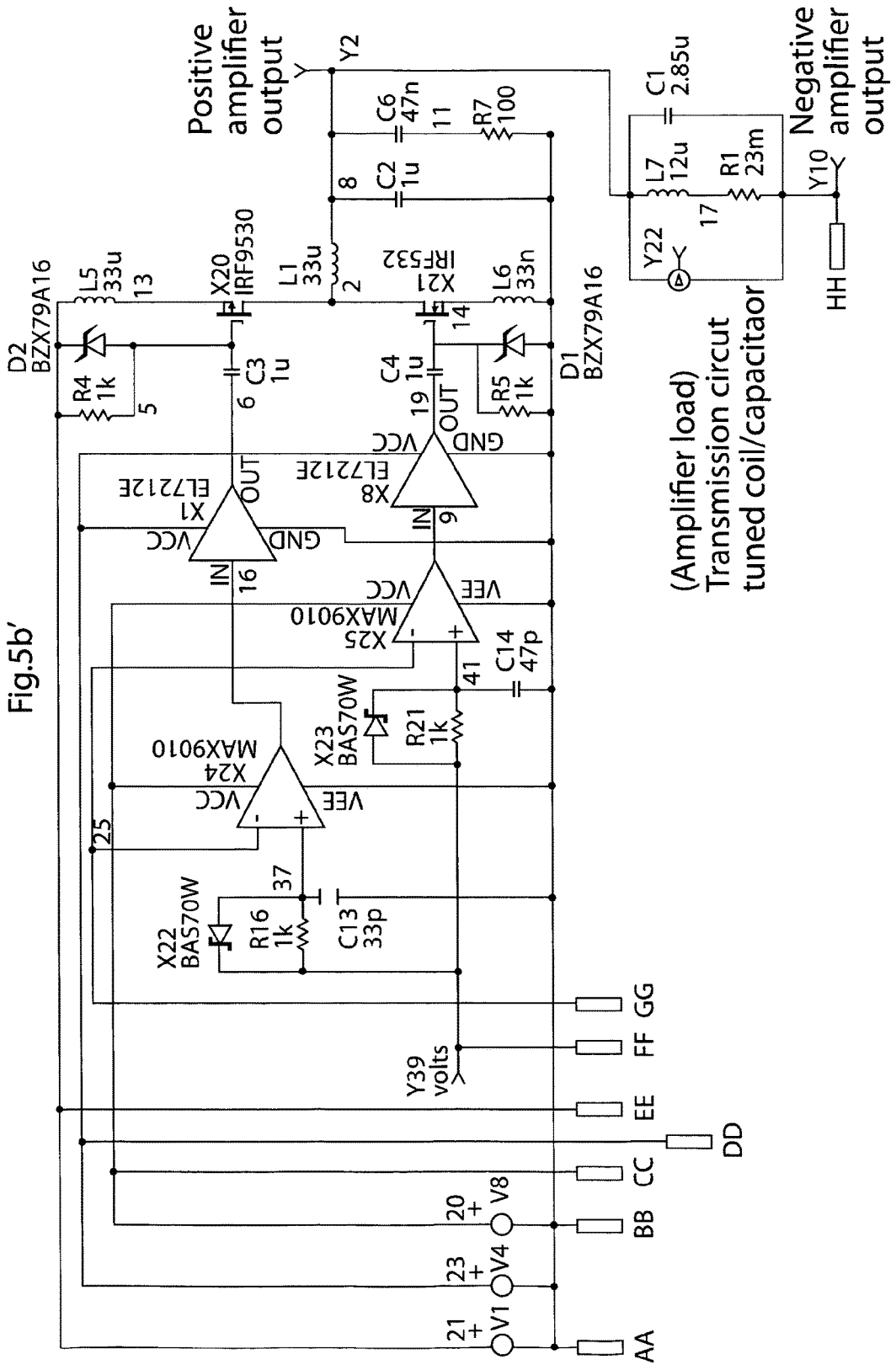
FIGS. 5b' and 5b" is a circuit diagram showing one embodiment of a PWMT amplifier.

FIG. 4b shows another example of transmitted pulses, according to a second embodiment of the present invention. During the time t1 a train of pulses is transmitted, and during the time t2 no pulses are transmitted. The pulses have a constant frequency and amplitude. However, the relation between the times t1 and t2 varies. FIGS. 5a and 5b show a solution with a circuit employing a continuous square wave pulse signal with a constant frequency where the duty cycle of each pulse is varied. In this type of solution the width of the output pulses from the PWMT amplifier is linearly regulated by the input signal voltage. The analog output from the PWMT amplifier is depending on the amplification factor of the circuit.

This type of amplifier can output any frequency within its frequency range from DC to the bandwidth of the output filter of the amplifier, the energy output to the load is a replica of the input voltage and not fixed to any particular frequency. However, in this example the PWMT amplifier is used at 25 kHz, the same frequency as used in the previous example. The input signal to the amplifier is a 25 kHz sine wave and the output supplies a parallel resonance circuit tuned to 25 kHz. The coil in the parallel resonant circuit is the transmitting coil.

The output power from the amplifier to the transmitting coil can be regulated linearly by adjusting the amplitude of the input sine wave signal which is different from the later discussed solution where the power regulation occurred by switching the power very quickly on and off.

FIG. 5a shows the triangle wave generator circuit which output is connected as an input in FIG. 5b of the PWMT amplifier. In FIGS. 5a and 5b the symbols Y1, Y2, Y3 and so on symbolize test points within the circuit. References to the test points are found on the graphs in the figures. The components in the circuit diagrams and their respective values are values that work in this particular implementation which of course is only one of an infinite number of possible design solutions.

FIGS. 5b' and 5b'' shows a circuit diagram containing most of the PWMT amplifier, in the lower left corner there is the LF input which is the input for the 25 kHz sine wave that should be amplified. The LF-input there is the triangle wave input emanating from the Triangle schematic. To the right in the middle in the Core schematic there is a transmission coil, L7, connected to the differential outputs, positive and negative output, of the PWMT-amplifier. The transmission coil L7 is in series with the series loss resistance R1 of the wire in the coil and in parallel with C1 that is the tuning capacitor to tune the transmitting coil to the sending frequency, which in this particular case is 25 kHz.

The amplification factor of the PWMT amplifier is about 70.

The PWMT amplifier circuit starts out in the triangle schematic. This schematic contains the triangle wave generator of the PWMT amplifier. The triangle wave generator is the heart of the circuit and the final precision of the amplifier is greatly influenced by the quality of the triangle wave.

V2 and V8 in the Triangle schematic are the power supplies for the operational amplifier with a +/−15V supply voltage. The V1 and V2 power supplies generate supply voltages for the X1 and X2 comparators that are configured so that the outputs from the comparators are centered on ground potential. FIG. 5c shows the output voltage from the X1 comparator, Y1, together with the feedback signal Y2 to the same comparator.

The X1 comparator compares the Y2 input signal with ground. If it is higher than ground the output is at high level and if lower it is at low level. There is a small amount of positive feed back from the comparator output to the positive input as can be seen in the Y2 trace in the diagram. When the output switches from high to low the Y2 trace level is pulled to a higher level by the output feedback than it had right at the moment when the output started to change. The feed back works in the same way when switching from high to low, the only difference being that the input is pulled down to a lower level instead of being pulled high. The feedback creates a hysteresis in the comparator circuit that together with the slowly increasing and decreasing output of the X1x amplifier form the core of an oscillating circuit, oscillating at 250 kHz.

The output of X1, Y1, is connected to the input of X1x via the current determining resistor R2x. The operational amplifier always tries to keep its inputs at the same level and when a positive current is put into R2x by the comparator X1 the output of the operational amplifier X1x has to supply the exact same amount of current through the capacitor C1x in order to keep the voltage differential between its inputs at zero.

When the comparator input to X1x is at a high level the current flowing into R2x is also flowing through C1x.

FIG. 5d shows the current through C1x, iy3x, and the output voltage from the X1x operational amplifier y2x. As long as the current flowing through C1x is perfectly constant the output of the amplifier X1x is increasing or decreasing in a perfectly linear fashion.

The linearity of the current flowing through C1x can be studied in FIG. 5e. It shows a magnified view of the positive part of the current iy3x through the capacitor C1x. The current is at approximately 5.49 mA and it is changing extremely little as the output voltage, y2x, changes over time. The vertical resolution in the diagram is 50 uA per division and the current is not changing more than maximum 5 uA apart from during the initial piece of the trace where some ringing is seen that is due to the finite bandwidth of the operational amplifier. The 5 uA change of the total current of 5.49 mA translates to a nonlinearity of less than 0.09% in the output triangle wave form.

To achieve this linearity level some further tricks has to be applied in the circuit. A small part of the output wave form y2x is feed back via C3 and R1x to the operational amplifiers positive input. This positive feed back is used to remove the amplifiers finite amplification factor from the equation and to compensate for the leakage current flowing through the DC feed back resistor R4x. By applying the correct amount of positive feedback it is possible to almost perfectly balance these factors.

FIG. 5f shows how the positive feedback signal y9 changes as the output voltage y2x from the amplifier changes over time. The y9 trace is not at a constant level as it would have been if the input was simply connected to ground, it is changing over time to compensate for the leakage current and the finite amplification factor of the operational amplifier as the output voltage y2x changes. The diagram also shows the negative input signal level y8 into the amplifier.

The ringing in the output wave form y2x and the current iy3x at the points where the output voltage changes from positive slope to negative or from negative to positive is due to the bandwidth limit of the operational amplifier. A triangle wave circuit needs an infinite bandwidth amplifier to be perfectly linear since the frequencies needed for a perfect transition from positive to negative slope are infinite.

Figure 5G:
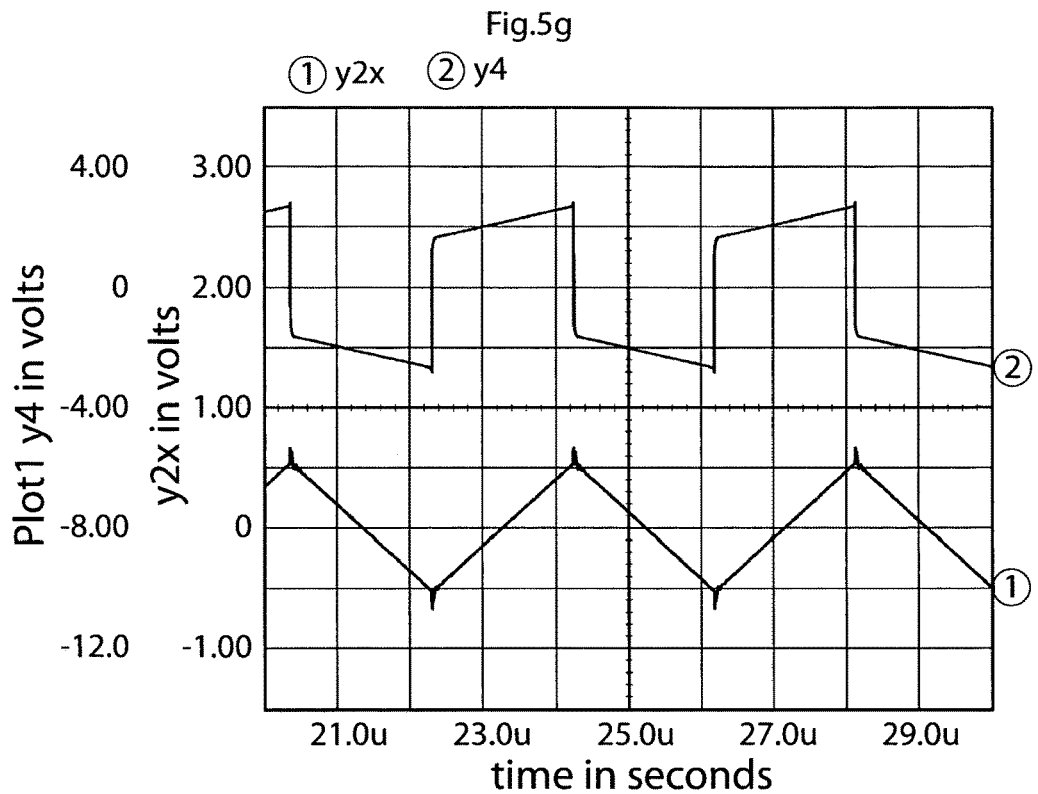

Such a circuit does of course not exist but there are a trick implemented in the circuit that improves the situation. The output of the comparator X2 changes when ever the output of X1 changes. The output from the comparator X2 is used to boost the output current and bandwidth of the operational amplifier X1x during slope switches. The output voltage of X2, y4 in FIG. 5g, is coupled to the operational amplifier output via the high pass filtering components R2 and C2. The boost provided by X2 linearizes the triangle wave and decreases the ringing in the output waveform, y2x in the diagram.

The output from the Triangle circuit, 250 kHz Triangle wave output, is feed in to the Core circuit at the bottom left as the 250 kHz Triangle wave input. The triangle wave signal is connected to the comparator X17 that compares the triangle wave input signal with the lower frequency analog input signal fed into the comparator from the LF-input.

Figure 5H:
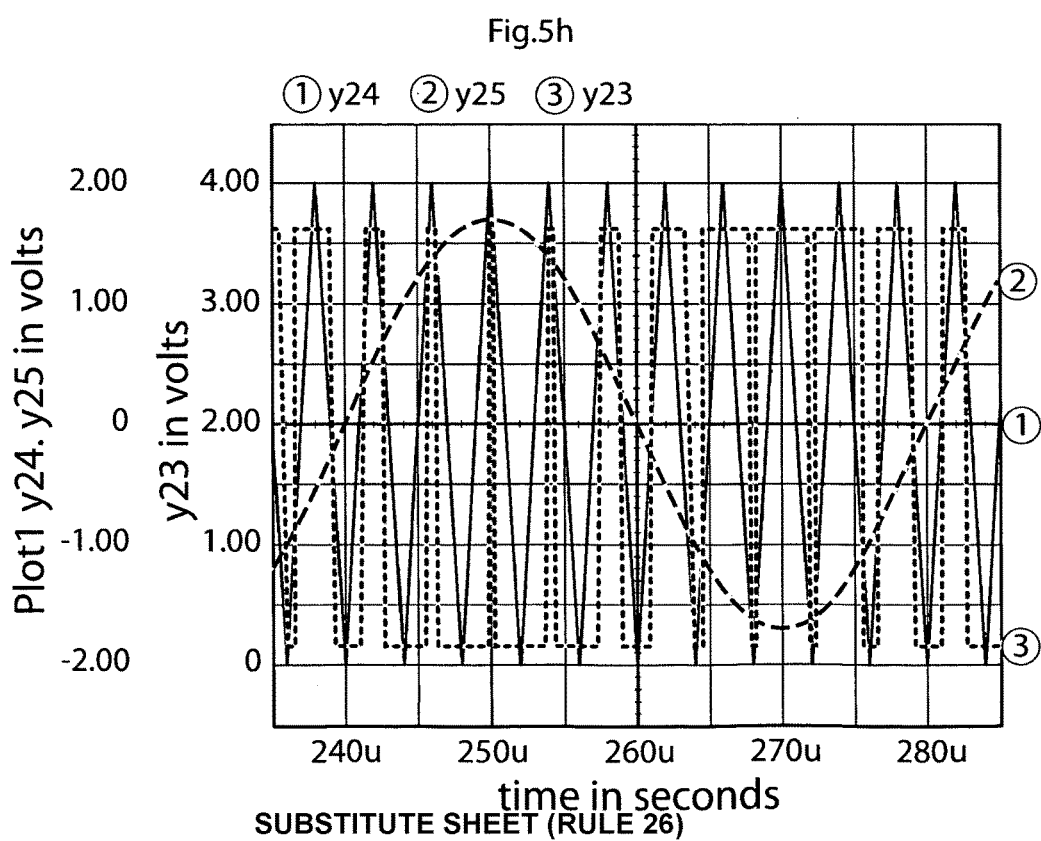

FIG. 5h shows the relation ships between the 250 kHz triangle wave input signal y24, the 25 kHz sine wave input on LF-input y25 and the y23 output voltage from the X17 comparator. The y24 and y25 voltages have the same vertical scale in the diagram. It can be seen that when the y24 triangle voltage is at a higher level than the LF-input signal y25 the output of the comparator y23 is at a high level and consequently when the triangle wave is lower than the LF signal the output is at a low level.

By studying the comparator output signal y23 it becomes clear that the signal is a PWMT signal with the base switching frequency of 250 kHz which controlled by the frequency of the triangle wave. The amount of high or low level of the digital output signal from the comparator, y23, correlates to the signal level of the LF-input signal, although it in this case actually corresponds to the inverted LF-input level. This extremely simple circuit actually does all the translation from a linear input signal to a high precision PWMT signal just by comparing the LF-signal level with a very linear triangle wave.

Figure 5I:
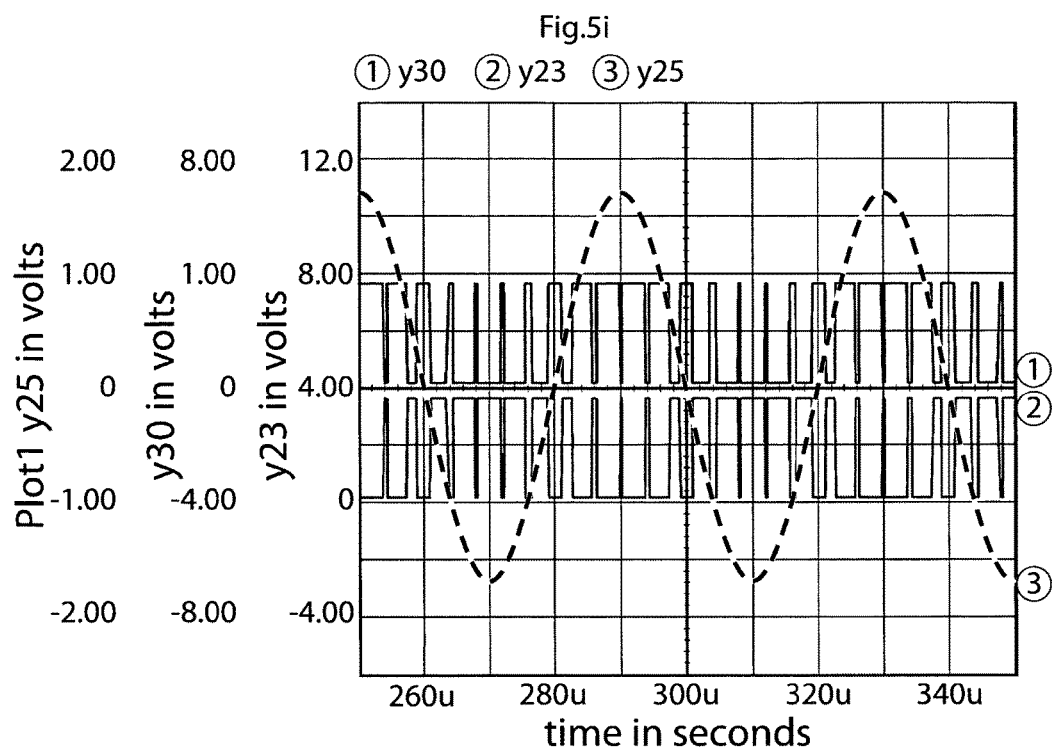

To perhaps even more clearly show the correlation between the input signal level and the PWMT output signal from the comparator X17 FIG. 5i displays both the positive and negative output PWMT wave forms from the X17 comparator together with the LF-input signal.

When the LF-input signal is at a higher level the positive output y30 from the comparator stays at a high level increasingly more as the LF-input signal reaches higher and higher levels and in the same manner the output stays increasingly more at a low level as the signal level decreases. The y23 output from the X17 comparator is the inverse of the y30 output as can be clearly seen in the diagram.

The positive and negative outputs from the X17 comparator is then fed to two buffering circuits, X2 and X11, to decrease the output impedance of the two signals before they are input to the pulse delaying circuits in the amplifier.

From here on the behavior of the circuit handling the positive part of the PWMT signal in the upper part of the schematic is exactly the same as the lower circuit handling the negative part of the PWMT signal. For simplicity only the lower part of the circuit handling the negative PWMT signal is discussed.

Figure 5J:
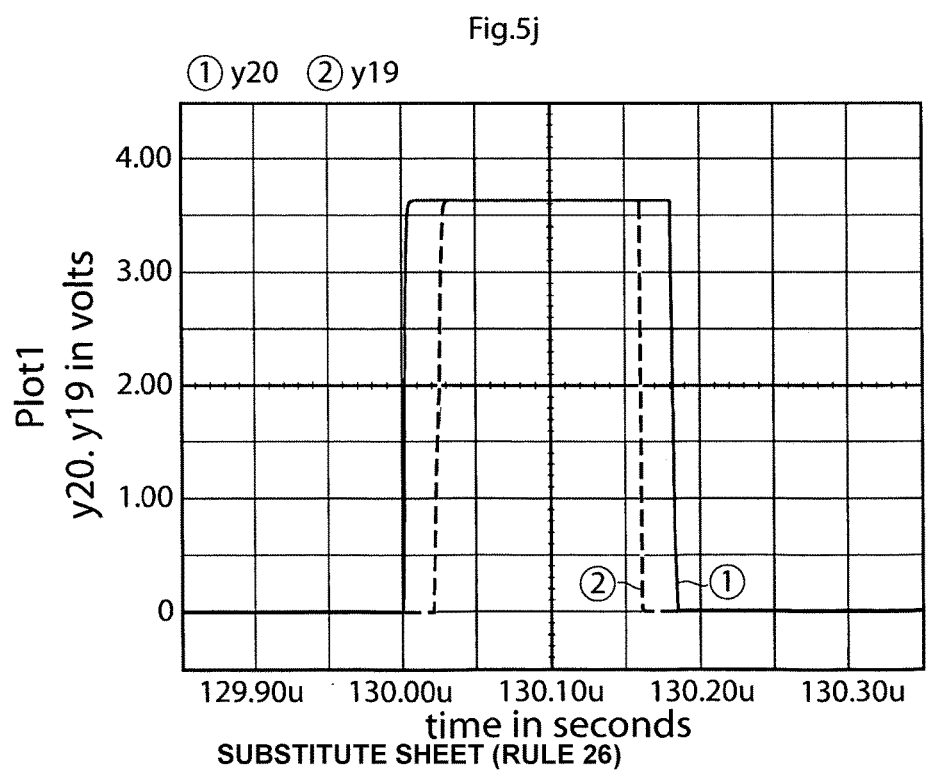

FIG. 5j shows the output from the timing circuit made up of the two comparators X15 and X16 together with the discrete components surrounding them in the schematics. The purpose of the timing circuit is to delay the turn on signal to one of the MosFets compared to the turn off signal to the other. Normally MosFets exhibit a slightly longer turn off delay time compared to the turn on delay. Due to this behavior there is a risk in a switching application such as this that if the turn on and off signals arrive at the same time to both the upper and the lower MosFets in the output stage there will be a current spike going through them during the transition period when one turns on just slightly before the other turns off. This is of course not desirable since it among other non beneficial effects radically decreases the efficiency of the circuit.

The timing circuit generates a turn on delay for both the upper and lower MosFets. For the lower MosFets the capacitor C12, resistor R31 and diode X12 for an asymmetrical delay that only delays the turn on flank in the signal and not the turn off flank. At turn off the capacitor C12 is rapidly charged by the low output impedance of the driving comparator X2 through the diode X12 to the comparator X16 threshold level and the output is switched momentarily as the input switches. At turn on the diode blocks the voltage and the C12 capacitor is charged at a slower pace through the resistor R31 creating a delay of the output transition compared to the input transition.

FIG. 5j shows the relationship between the two voltages coming out of the timing circuit. The y19 trace shows the signal to the upper MosFet and the y20 trace the signal to the lower MosFet. The horizontal resolution in the diagram is 50 ns per division. To understand the diagram it is important to know that the y20 trace has an inverted function compared to the y19 trace. When y20 is high the lower MosFet is turned off and when it is low it is turned on. This is due to the inverting function of the MosFet drivers X13 and X14 and the fact that the upper MosFet is a P channel device that also, once more, inverts the signal causing the y19 trace to be correct and the y20 trace to be inverted if one consider it to be normal that when the signal level is high the MosFet is on.

In the diagram it is then clear that the y20 signal is turning the lower MosFet off about 25 ns before the y19 signal is turning the upper MosFet on and in the same manner the upper MosFet is tuned off by the y19 signal about 25 ns before the lower MosFet is turned on by the y20 signal.

Figure 5K:
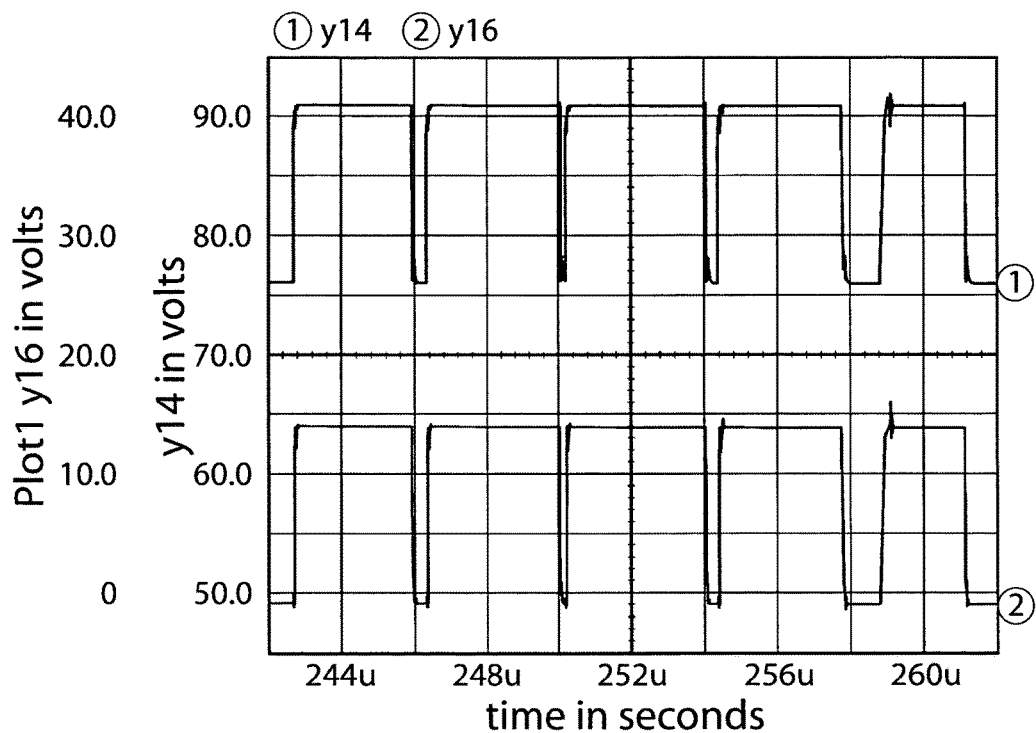

FIG. 5k shows the input voltages to the upper and lower MosFets respectively. The upper MosFets driving voltage is the y14 trace and the lower MosFets driving voltage is the y16 trace.

Both output signals from the MosFet drivers X13 and X14 are AC coupled before they are connected to the MosFets. This is beneficial for both the lower and the upper MosFets. The AC coupling of the signal to the lower MosFet changes the signal levels so that the output swing from the driver, which is changing between 0 and 15 volts at the output, swings between −0.7 and 14.3 volts at the gate of the MosFet. The negative swing is beneficial because it gives a somewhat greater margin to unwanted turn on of the MosFet during output voltage transition from low to high level. The MosFet typically starts to conduct when the gate source voltage is more than 1.5V. If the gate source voltage at off state is lowered from 0V to −0.7V this increases the safety margin for unwanted turn on from 1.5V to 2.2V which is an improvement of about 45%.

One of the benefits of the AC coupling of the upper MosFet is the same as for the lower one, creating a higher safety margin for unwanted turn on of the MosFet during high to low output voltage transitions. The other advantage of the AC coupling is that there is no need for a high voltage driver to the upper MosFet since the AC coupling automatically places the gate voltage range from 0.7 V above supply voltage to 14.3 V below supply voltage. This is demonstrated by the y14 trace in FIG. 5k that change from 90.7 V at high level down to 75.7 V at low level with a supply voltage of 90 V creating a gate to source voltage for the upper MosFet that changes between 0.7 V at high level and down to −14.3 V at low level.

Figure 5L:
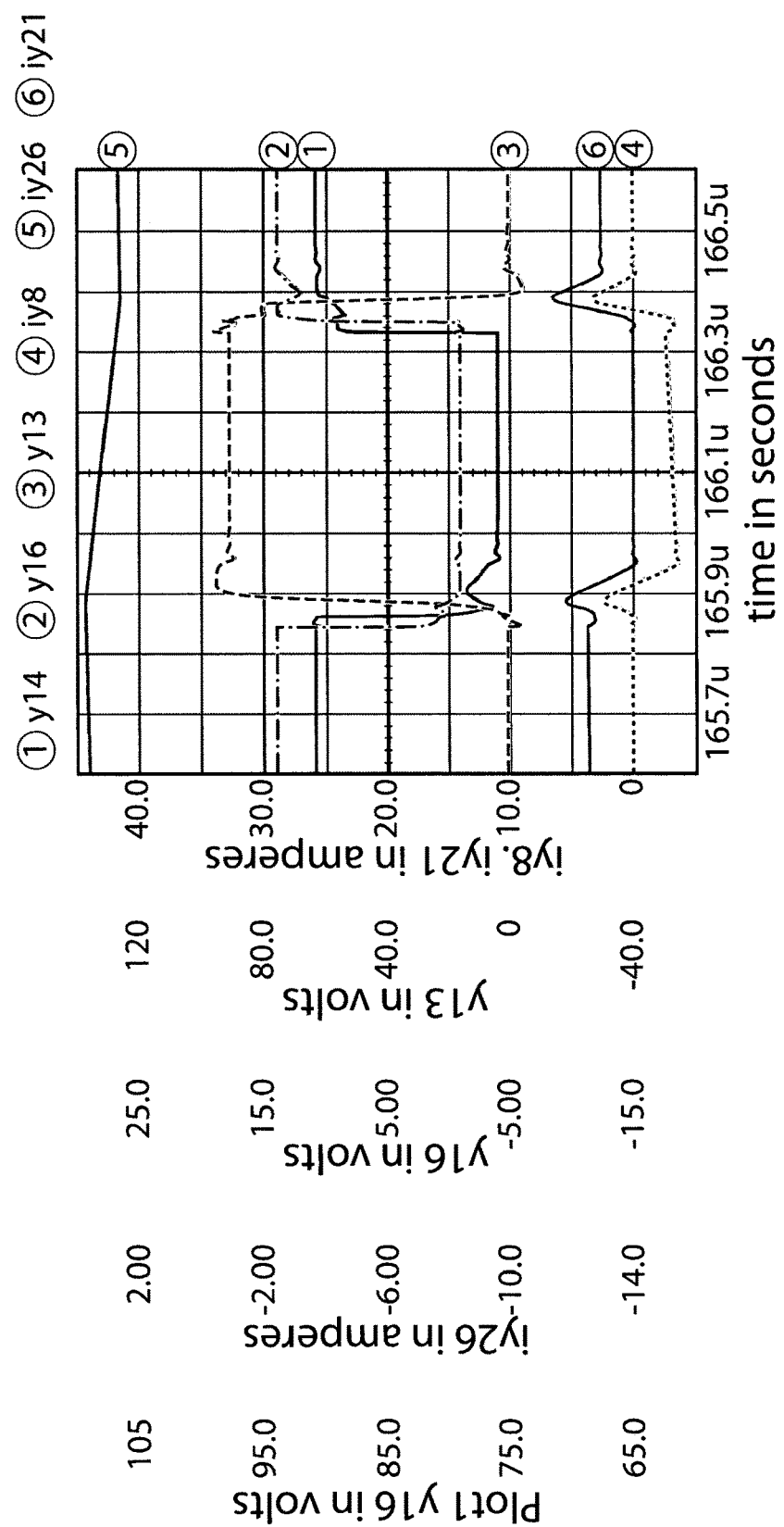

FIG. 5l shows the relationship between the output voltage y13 from the MosFets and the gate drive voltages y14 and y16. The importance of the above discussed safety margin for unwanted turn on of the MosFets is clearly shown by the hump in the y16 trace at the beginning of the low voltage part for the trace in the diagram coinciding with the low to high transition for the output voltage y13. What is happening is that the gate drain stray capacitor in the lower MosFet pulls the gate voltage to a higher level when the drain voltage rapidly increases forcing the MosFet gate driver X13 to deliver current to the gate to keep it at a low voltage level. Due to the fact that the output impedance of the driver is not ideally zero ohms but a few ohms make the gate voltage increase during this period to a level about 1 V above ground. Without the additional 0.7 V safety margin this could have caused the lower MosFet to turn on and conduct current at a time when this would have been highly undesirable. The same behavior can be studied in the y14 trace when the output voltage y13 changes from high to low where the drain gate stray capacitance pulls down the level of y14 to about one volt below the supply voltage.

The diagram also displays the currents through the MosFets, iy8 and iy21, and the output current iy26 going through the output filtering coil L2. The PWMT square wave output y13 from the MosFets is filtered by the output filter formed by L2 and C7. The filter removes the high switching frequency and leaves the amplified low frequency signal that resembles the LF-input signal to the amplifier amplified to a level about 70 times the LF-input level.

The positive amplifier output is an inverted version of the Negative amplifier output, if the positive output is at +10 V the negative is at −10 V. The load, the transmitting coil L7 and parallel resonance circuit formed together with C1, is connected between the positive and negative amplifier outputs. When there is no input signal to the amplifier both the outputs stays at half the supply voltage level creating an output level of 0 V. If the input signal is positive the positive voltage is above half supply voltage and the negative below creating a positive output voltage from the amplifier and if the input voltage is negative the positive output is below half supply voltage and the negative above creating a negative output voltage from the amplifier.

The significant advantage of the PWMT approach of the first implementation circuit is that the power losses in the PWMT amplifier compared to a standard linear design is radically decreased. At the same time the circuit exhibits the same behavior as a linear design, it has a constant amplification factor and it amplifies an input signal from DC to about 25 kHz by this factor. The output bandwidth of the amplifier is limited by the switching frequency and the upper cut off frequency of the output filter. The cut of frequency of the output filter has to be low enough to avoid having significant amounts of the switching frequency on the amplifier output. To increase the bandwidth of the amplifier it is therefore necessary to increase the switching frequency. The upper limit of the switching frequency is set by the stray capacitances in the MosFets and their turn on and off delays. Large power MosFets have longer delays and higher stray capacitances making higher switching at frequencies increasingly difficult. The in this design chosen frequency of 250 kHz could be increased slightly but at the price of increased switching losses and thereby degraded efficiency.

Figure 6A:
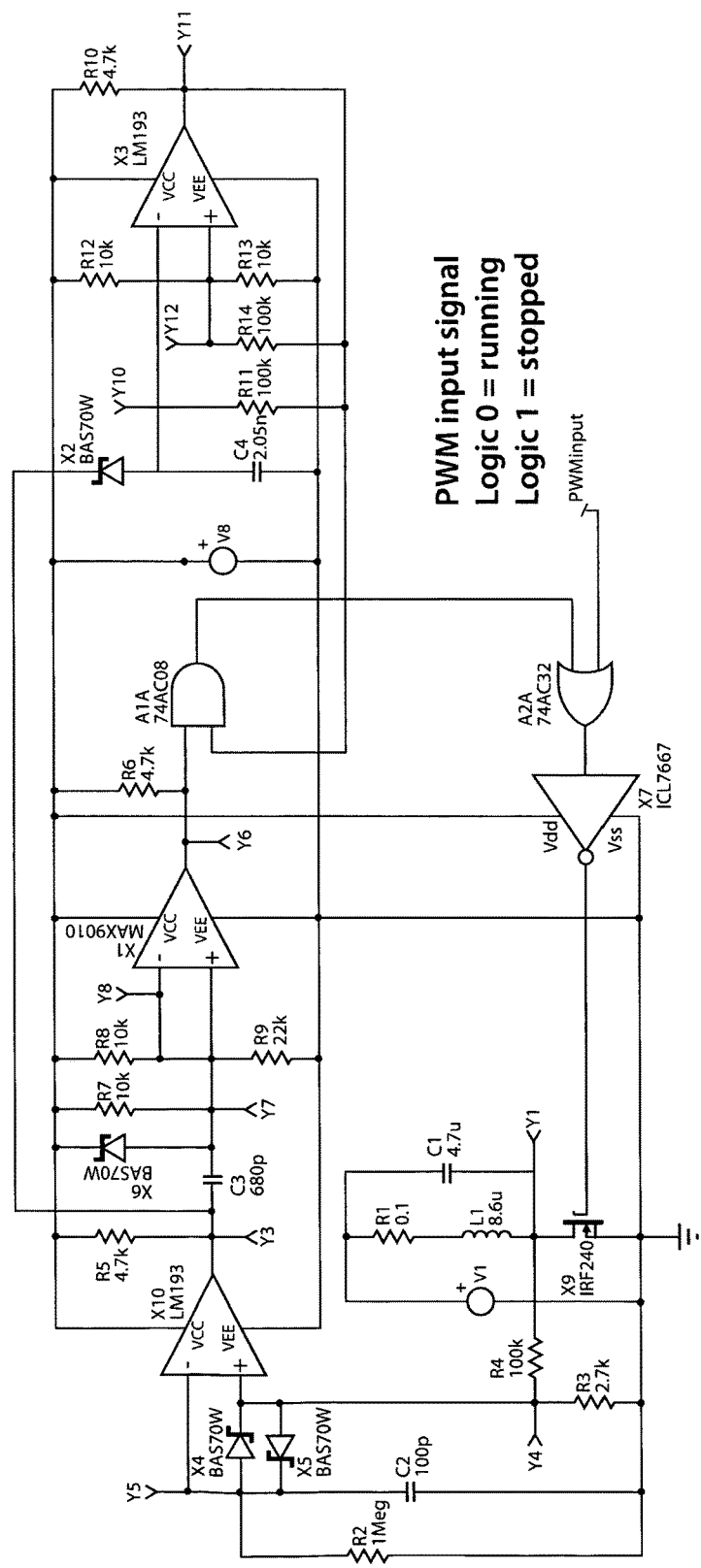
FIG. 6a is a circuit diagram showing another embodiment of a PWMT amplifier.

FIG. 6a shows another embodiment of a PWMT system. The energy transfer control technique in this case uses a modified PWMT approach that switches a continuous pulse train off during several pulse periods and then on again for several pulse periods. The advantage of this technique is that it is easily controlled by a standard microprocessor and it does not unnecessarily burden the microprocessor with a large workload for the regulation task. The switching of the system can be made rather slow, in the millisecond range. This is of course a large advantage since it is possible to have the processor do other things in the system and it is also possible to use a less powerful and therefore cheaper microprocessor.

In FIG. 6a the symbols Y1, Y3, Y4 and so on symbolize test points within the circuit. References to the test points are found on the graphs in the diagrams following later in the text. The components in the diagram and their respective values are values that work in this particular implementation which of course is only one of an infinite number of possible design solutions.

In FIG. 6a L1 is the transmitting coil. R1 is the series loss resistance in the wire in the coil and C1 is the tuning capacitor to tune the transmitting coil to the sending frequency, which in this particular case is 25 kHz.

The PWMT input signal is a logic input signal from a microprocessor or some other suitable control logic. The PWMT input signal switches power to the transmitting coil on and off many times per second. Whenever the input is at a logic low level power is transmitted and when it is at logic high level the transmission is switched off.

The V1 and V4 components in the circuit are power supplies. The voltage of V1 is 100V and it powers the power amplifier that energizes the transmitting coil. The voltage of V4 is 5V and it powers the analog and logic circuits in the schematic. The symbols Y1, Y3, Y4 and so on symbolize test points within the circuit. References to the test points are found on the graphs in the diagrams following later in the text. The components in the diagram and their respective values are values that work in this particular implementation which of course is only one of an infinite number of possible design solutions.

Figure 6B:
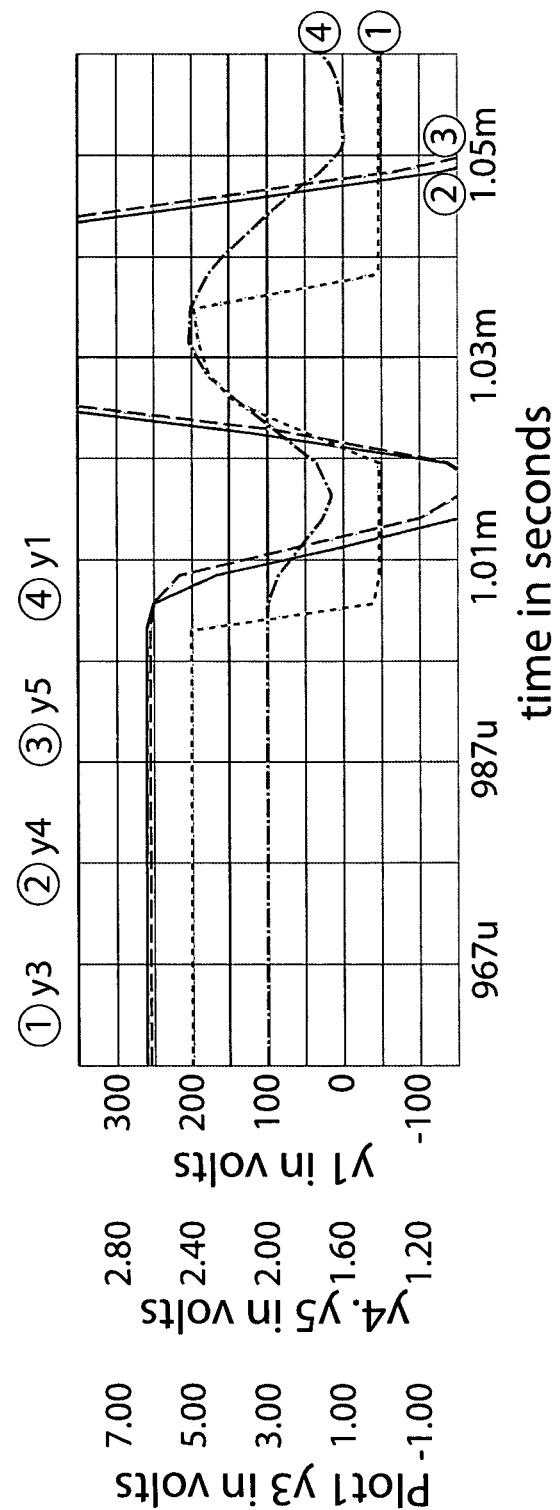

FIG. 6b shows different voltages in the circuit surrounding the comparator X10 at startup when the transmitting voltage Y1 is tuned on. The turn on point is in the middle of the diagram where the voltage Y1 starts to decrease from 100V to about 20V.

The resistors R4 and R3 form a voltage divider that divides the voltage, Y1, over the transmitting coil L1. This voltage, Y4, is fed into the positive input of the X10 comparator and is presented in the FIG. 6b by graph 3. The Schottky diodes X4 and X5 in combination with the capacitor C2 and resistor R2 are used to make the voltage Y5 lag behind the Y4 voltage. When the Y4 voltage increases the Y5 voltage will be one diode voltage below Y4 and the current through the diode X5 will charge the capacitor C2. When the voltage Y4 starts to decrease the Y5 voltage will remain higher than the Y4 voltage because of the charge stored in C2. In this way the Y5 voltage will always be higher than Y4 if the Y4 voltage is dropping and it will be lower then Y4 if the Y4 voltage is rising. By feeding these voltages to the X10 comparator positive and negative inputs respectively the output voltage from the comparator, Y3, will be an indication on whether the voltage Y1 over the transmitting coil is rising or falling. If the Y1 voltage is raising the Y3 voltage is at a logic high level and if the Y1 voltage is falling the Y3 voltage is at a logic low level. This is shown in FIG. 6c.

FIG. 6c shows the voltages around the comparator X1 when the output voltage from X10, Y3, is changing due to a changing voltage at Y1 as seen in the diagram to the right of the center point of the diagram.

Figure 6D:
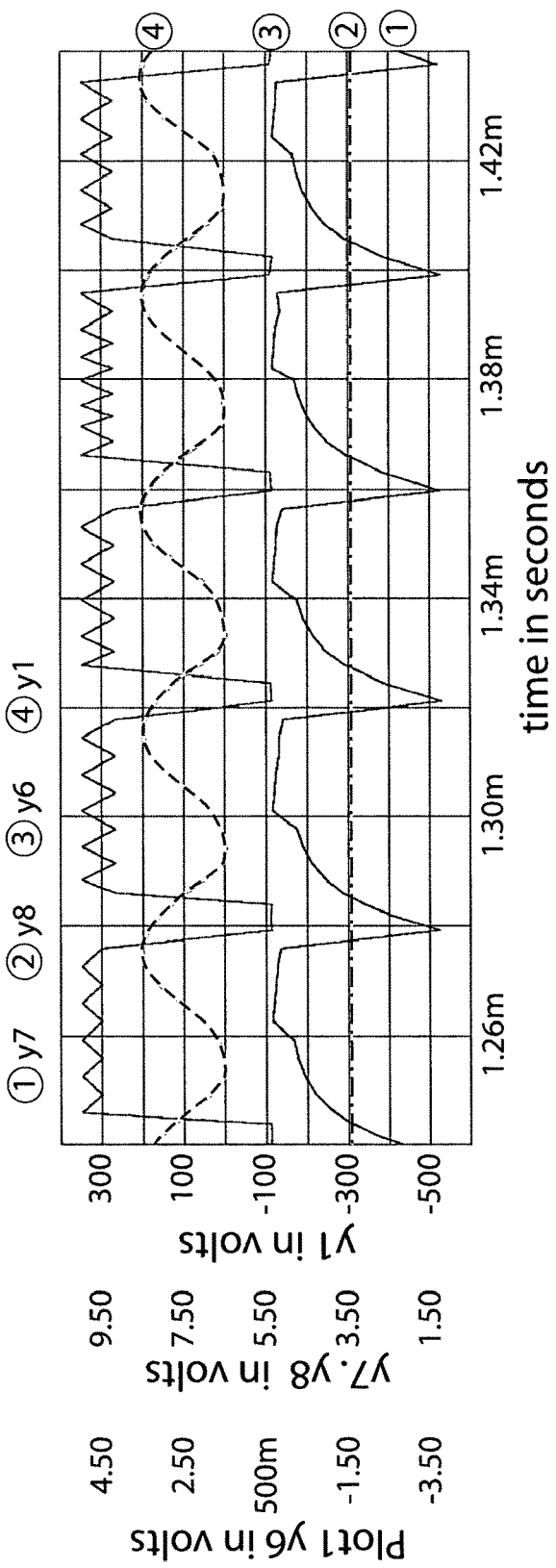

FIG. 6d shows four graphs, and is described below. The X10 circuit is used to generate a single pulse output with constant length upon changes of the Y3 voltage from logic high to logic low level, meaning that each time Y1 changes from positive going to negative a negative pulse voltage, Y6, is generated. The negative input of X10, Y8, is held at a constant level of about 3.5V by the resistor divider R8 and R9. This constant voltage is compared to the Y7 voltage. The Y7 voltage is pulled low by the high to low level transition of the Y3 voltage and it is returning to a high level in a pace determined by the charging of capacitor C3 through resistor R7. The diode X6 is merely in the circuit to prevent voltages higher than the supply voltage at Y7 when the Y3 voltage changes from a low to high level. The capacitor C3 is in this case discharged through the diode X6.

Figure 6E:
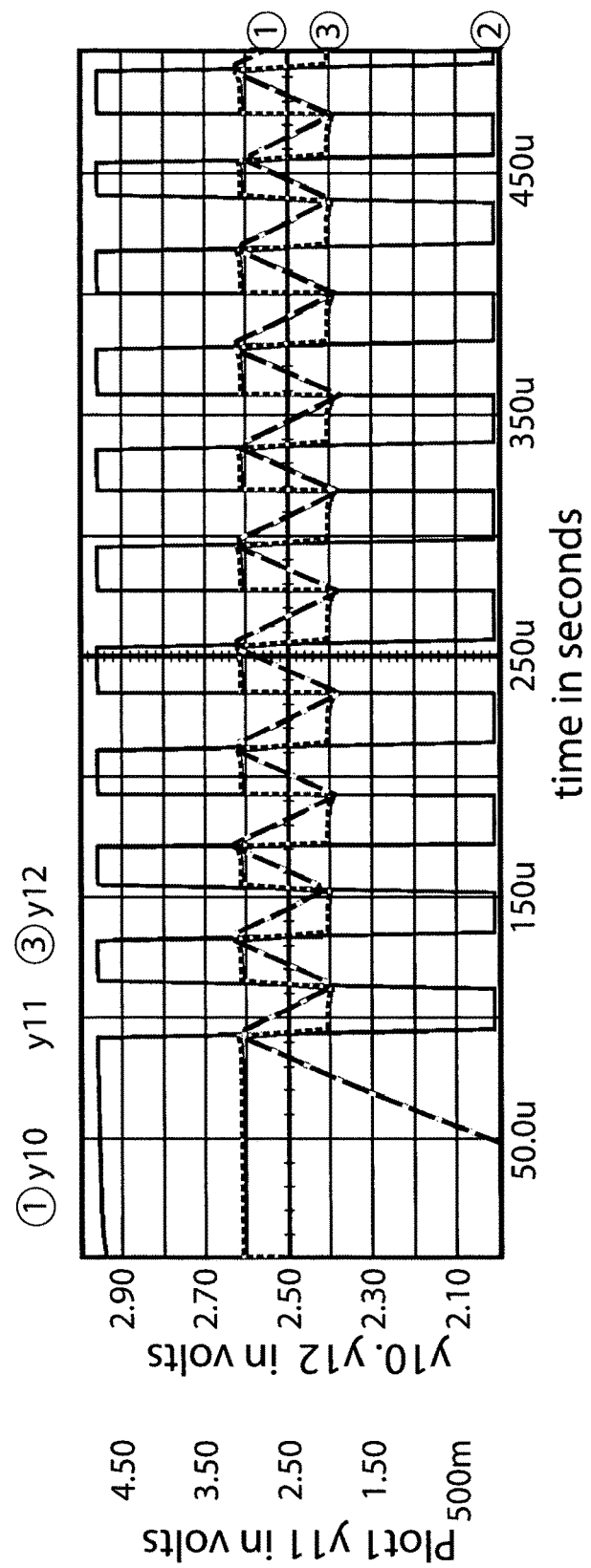

The voltages in the circuit around X3 are shown in FIG. 6e. The voltages are shown from an initial power up of the circuit and for duration of 500 microseconds. At T=0 the voltage Y10 starts to increase when the capacitor C4 is charged through resistor R11. When the Y10 voltage reaches the same level as the Y12 voltage the output voltage of X3, Y11, changes from a high to a low logic level. This change in Y11, make the Y12 voltage level drop and the Y10 voltage starts to decrease because of the discharging of capacitor C4 through resistor R11. Again, when the Y10 voltage reaches the same level as the Y12 voltage the Y11 voltage changes from a low logic level to a high logic level. The output voltage, Y3, from the X3 circuit is a continuous pulse train with a frequency of 25 kHz.

Figure 6F:
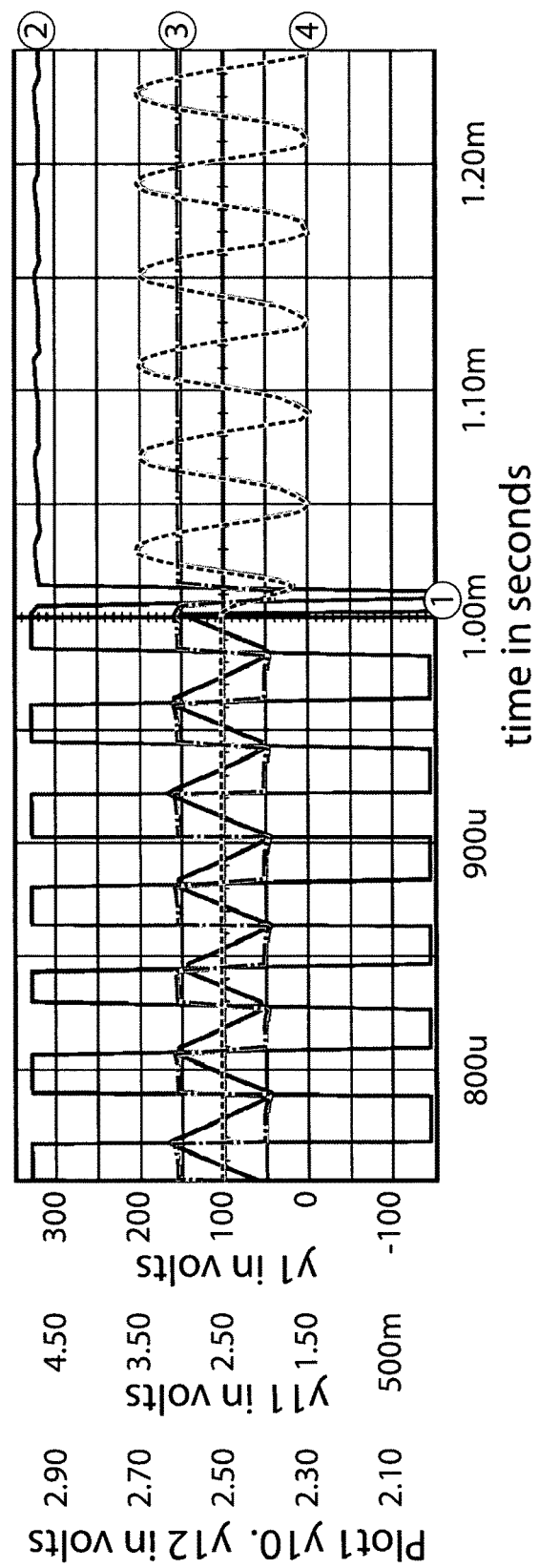

FIG. 6f shows the voltages in the X3 circuit when the Y1 voltage deviates from zero. In the left part of the diagram the voltages Y10, Y11 and Y12 are the same as in FIG. 6f after the initial startup phase. At once, when the Y1 voltage starts to change, the Y10 voltage is pulled low trough the diode X2 by the changing Y3 voltage generated by X3. This makes the continuous pulse train output, Y11, from X3 stop. As long as Y3 becomes low at times due to the changing Y1 voltage the Y10 voltage is never returned to a level as high as the Y12 voltage and thus the output voltage Y11 will always stay at a logic high level as long as the Y1 voltage is changing.

In the circuit the power transistor X9 is either turned completely on by the drive voltage from X7 or turned completely off. The input signal to X7 is either changing or constant depending on the logic level of the PWMT input signal. If the PWMT input signal is at logic high level the output of A2A is always high making the output of X7 always low causing the power transistor X9 to be turned off. In this mode there is no drive power to the transmitting coil and no energy is transmitted to the receiving coil. If the PWMT input signal is at a logic low level the output of A2A is free to change according to the changes of the signal coming from A1A. The output signal from A1A can change when the Y6 voltage is at a logic high level, which it is at startup before the Y1 signal starts to change in level.

Initially, when the circuit is started, there is no voltage change in Y1 and therefore the Y6 voltage is constantly at a high logic level. To make the Y1 voltage change a startup signal is required. This startup signal is fetched from the continuous pulse train Y11. When the Y11 signal has started the Y1 signal the Y11 signal is stopped and help at a high logic level by the presence of the Y3 signal and the Y6 signal starts to generate the output pulses from A1A ultimately driving the power transistor X9. The Y6 voltage pulses is in this case driving the L1 transmitting coil at a pace determined by the tuning frequency of the transmitting coil L1 and the capacitor C1. This startup behavior is show in FIG. 6f.

Figure 7A:
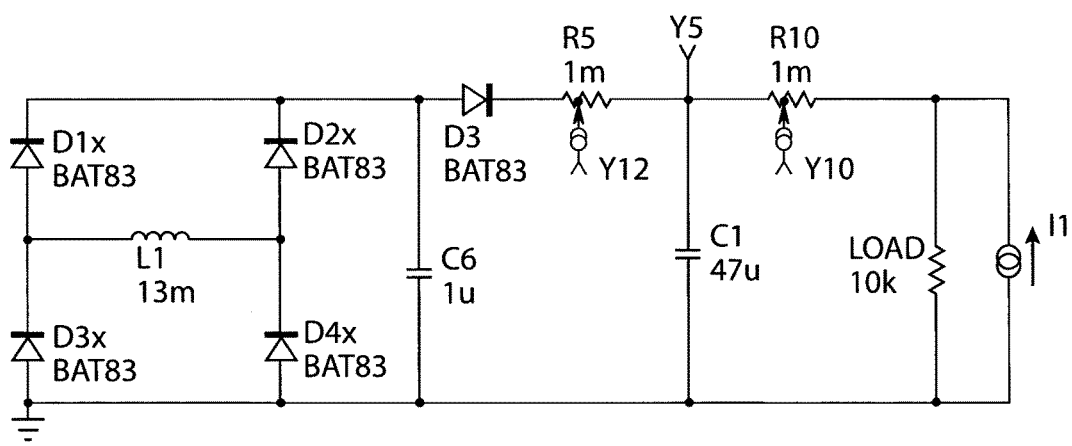
FIG. 7a is a circuit diagram showing an embodiment of a receiving end circuit in a TET-system.

FIG. 7a shows a diagram of an electronic circuit in the receiving end of the TET transmission system. The energy pickup coil, L1, receives power transmitted from the sending coil, also termed L1 in the PWMT amplifier diagram. The circuit and the diagram are included to illustrate the effect of the regulation of the transmitted power from the PWMT amplifier.

The receiving coil L1 together with the diodes D1x to D4x charges the capacitor C6 that creates a first smoothing filter for the received AC energy signal. The diode D3 prevents capacitor C1 from discharging into C6 when power is not supplied from the receiving coil L1. The resistors R5 and R10 are only used for current measurement purposes and have no other effect in the circuit due to their low resistance of 1 mohm. The capacitor C1 is the main energy storage of the circuit. It supplies power to the load resistor LOAD and the varying current source load 11.

Figure 7B:
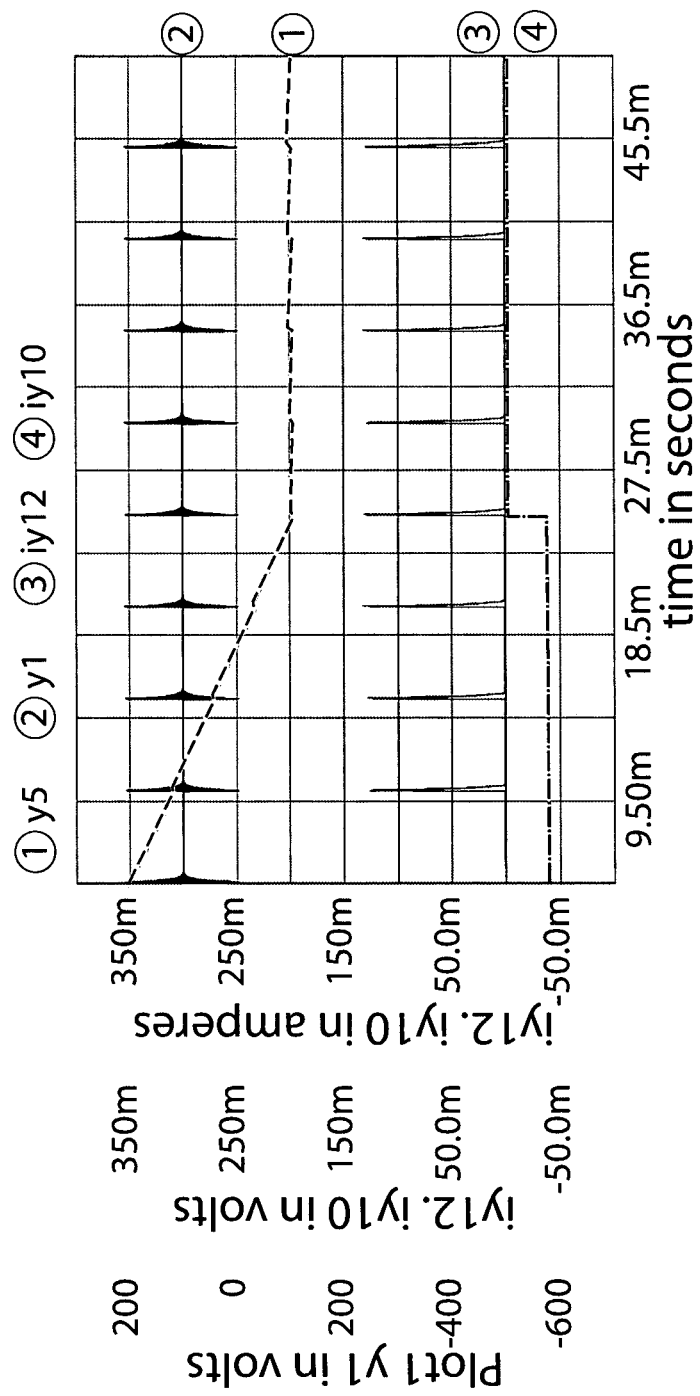

FIG. 7b shows four graphs. The total load current drawn from C1 by resistor LOAD and current source 11 varies over time beginning at 40 mA and changing to 4 mA after 25 mS as shown in the diagram by graph 4, IY10. Y5 in the diagram shows the voltage over C1, the current supplied to C1 is shown by iy12 and finally the voltage over the receiving coil L1 is displayed by the graph y1.

The voltage over C1, Y5, drops as long as the load current is 40 mA. When the load current decreases to 4 mA the voltage becomes stable, indicating that the average current supplied by L1, iy12, to C1 is 4 mA. The pulses picked up by the receiving coil are very short with about 2% duty cycle meaning that the power received from the PWMT amplifier is only supplied during 2% of the total PWMT period of 5 ms. The 2% duty cycle apparently provides enough power for a 4 mA load but is not enough for the 40 mA load since the voltage over C1 is at a constant level when 4 mA is drawn from it by the load. FIG. 7c shows a detailed view of the voltage over the receiving coil L1 and the PWMT amplifiers modulation signal, PWMT input signal in the PWMT amplifier diagram, in this case with 2% duty cycle.

FIG. 7d shows an even greater detail of the voltage over the receiving coil L1 and the PWMT amplifiers modulation signal. In the diagram it can be observed that the voltage over the L1 receiving coil exhibits a long slowly decreasing ringing after the PWMT amplifier has been turned off. This behavior is due to the energy stored in the resonance circuit on the transmitting side of the system formed by the transmitting coil L1 and the capacitor C1 in the PWMT amplifier diagram. When the PWMT amplifier is turned off the transmitting resonance circuit still transmits using the energy stored in the parallel resonance circuit itself. Even if the PWMT amplifiers PWMT input signal has a 2% duty cycle the resulting transmitted signal seems to equal about 4% duty cycle due to this stored energy.

Figure 7E:
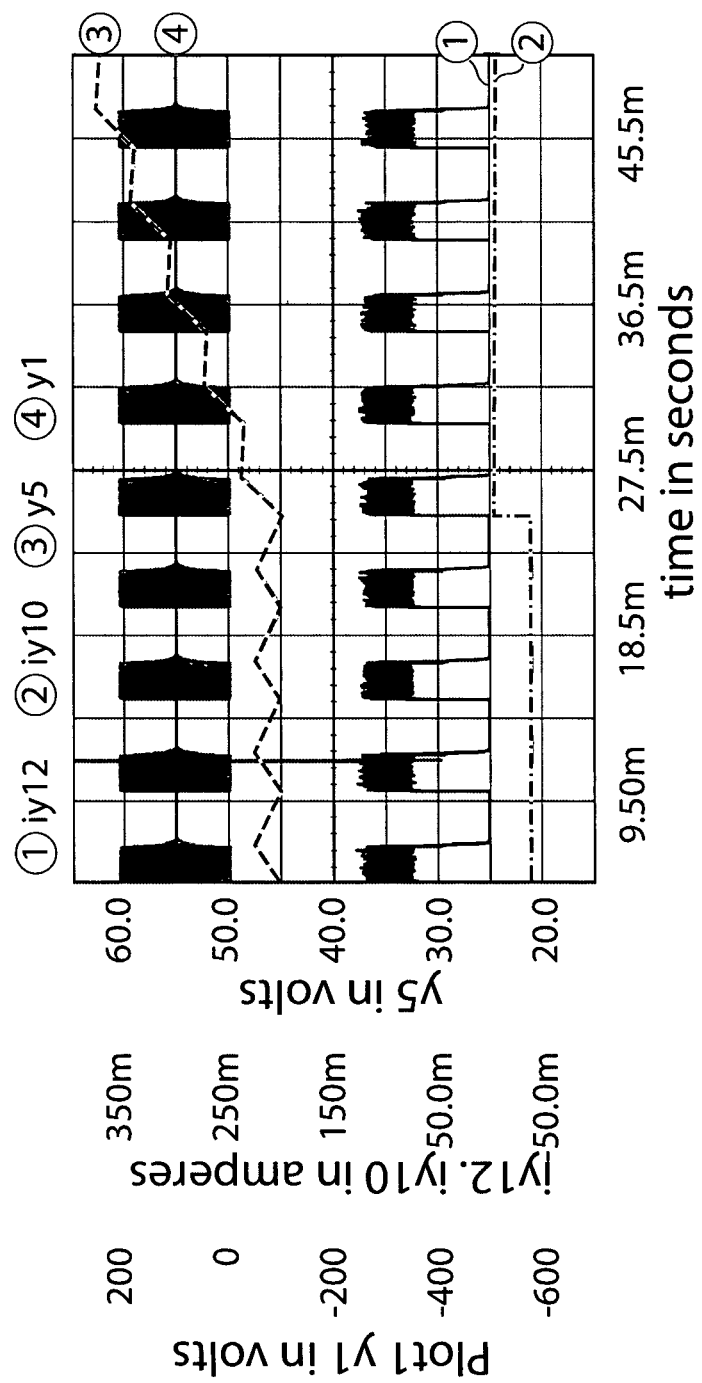

In order to supply enough power and current during the 40 mA consumption period for the voltage over C1 to stay constant the PWMT duty cycle has to be increased to 40%. FIG. 7e shows the voltages and currents that are present in the circuit with a 40% duty cycle. The voltage over C1, Y5, is now constant during the initial period up to 25 ms and then starts to increase when the load current is decreased to 4 mA.

Figure 7F:
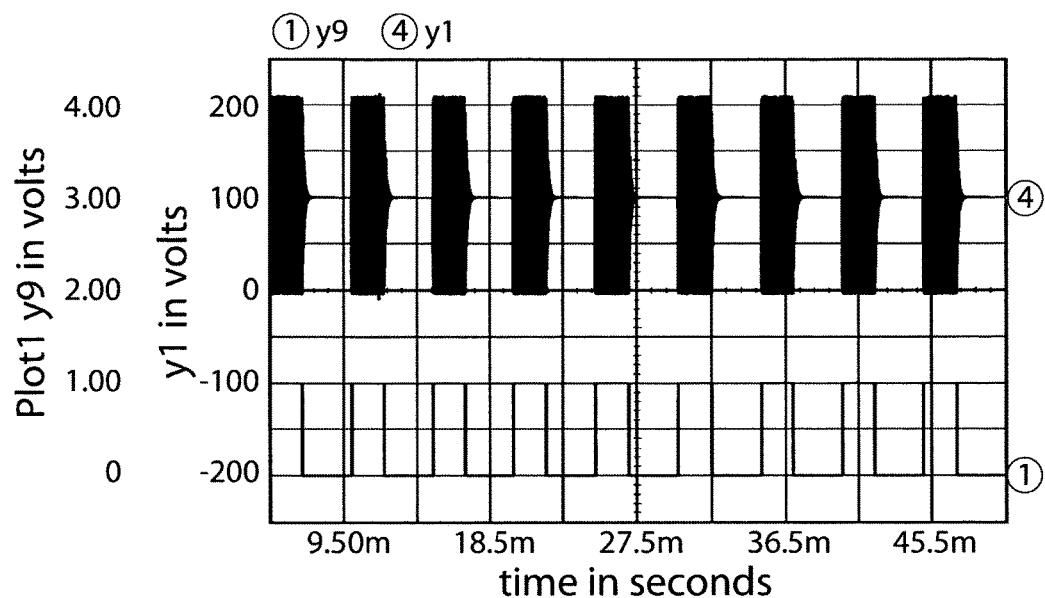

FIG. 7f shows a detailed view of the voltage over the receiving coil L1 and the PWMT amplifiers modulation signal, PWMT input signal, with the 40% duty cycle.

Figure 7G:
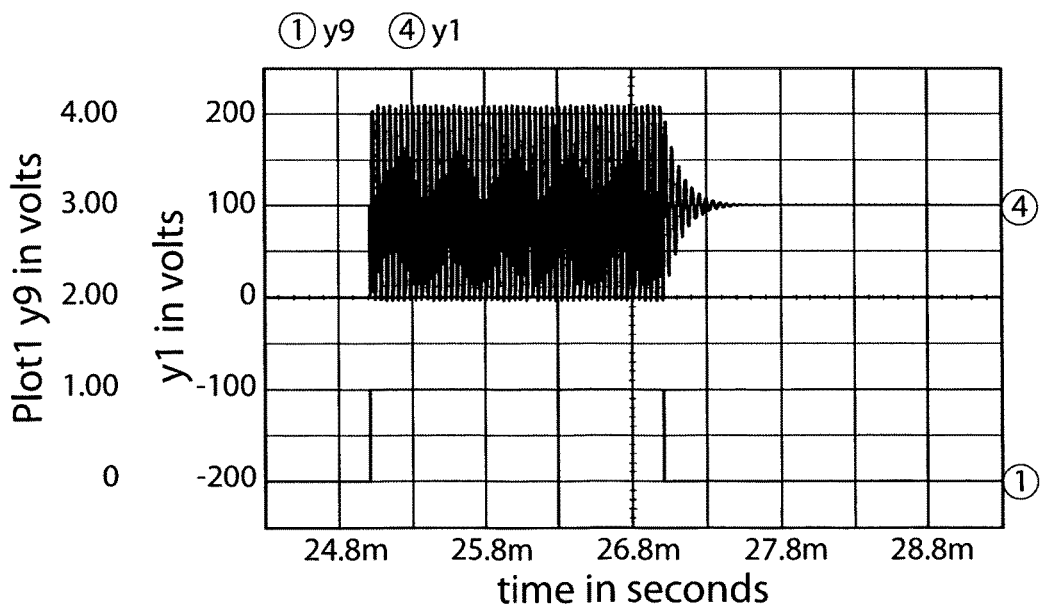

In the particularly detailed FIG. 7g it can be observed that the ringing from the energy stored in the transmitting parallel resonance circuit now contributes much less to the total signal over L1 with a 40% duty cycle compared to the 2% duty cycle case.

Figure 7H:
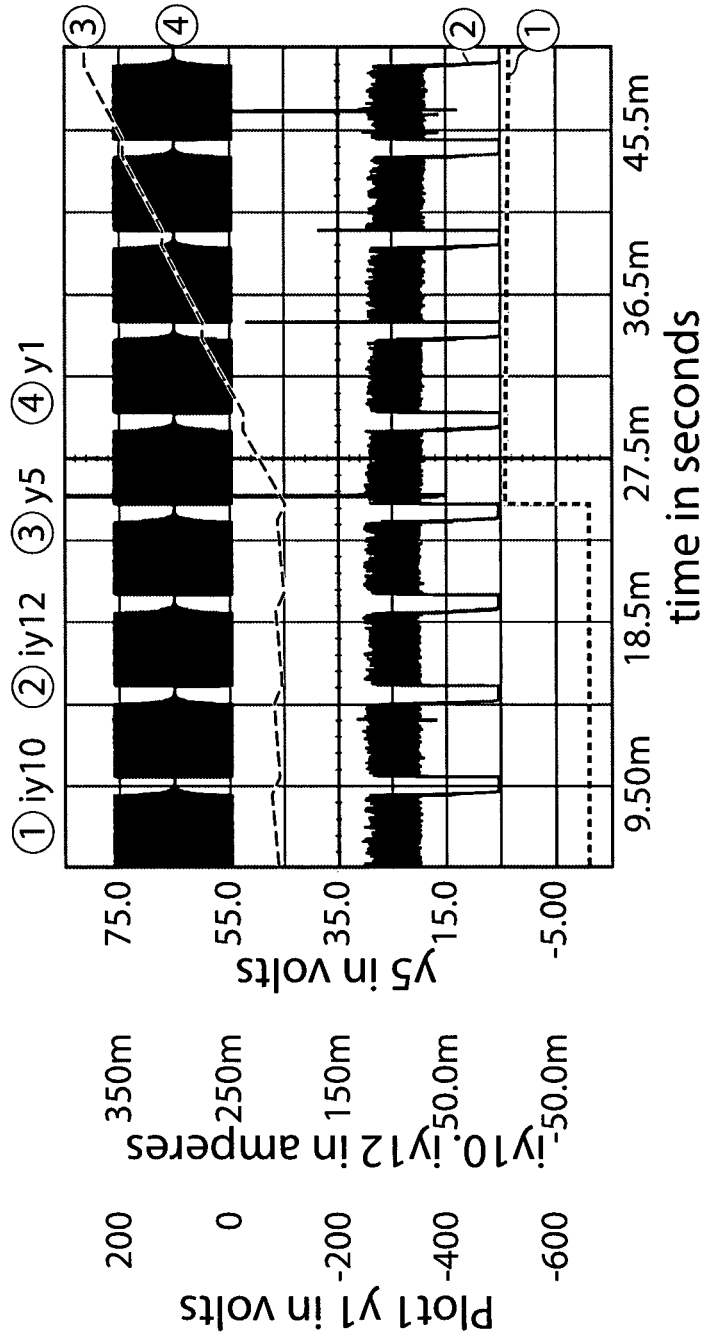

According to FIG. 7h, by increasing the PWMT duty cycle to 80% it is possible to supply even more power to the receiving coil and circuit. The power consumption now has to be increased to 80 mA to be able to balance the current supplied by L1. During the first 25 ms the voltage over C1, Y5, stays at the same level and it rapidly starts to increase when the current load is decreased to 4 mA.

Figure 7I:
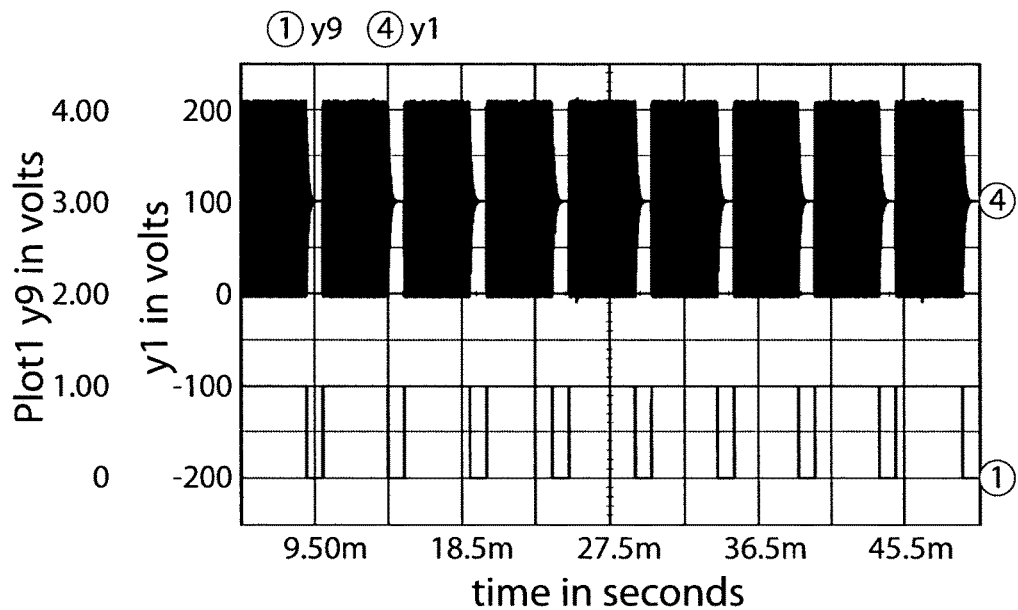
Figure 7J:
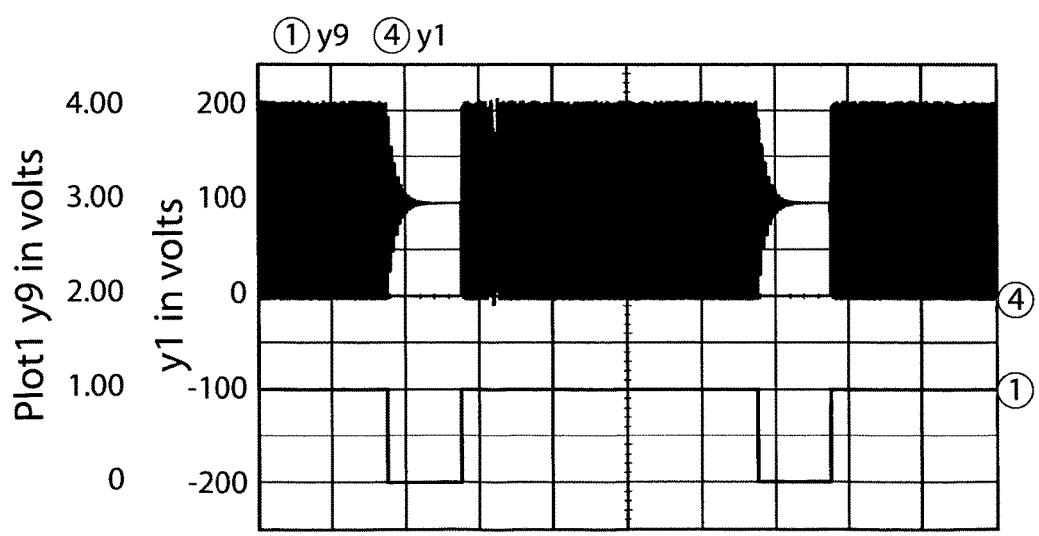
Figure 8A:
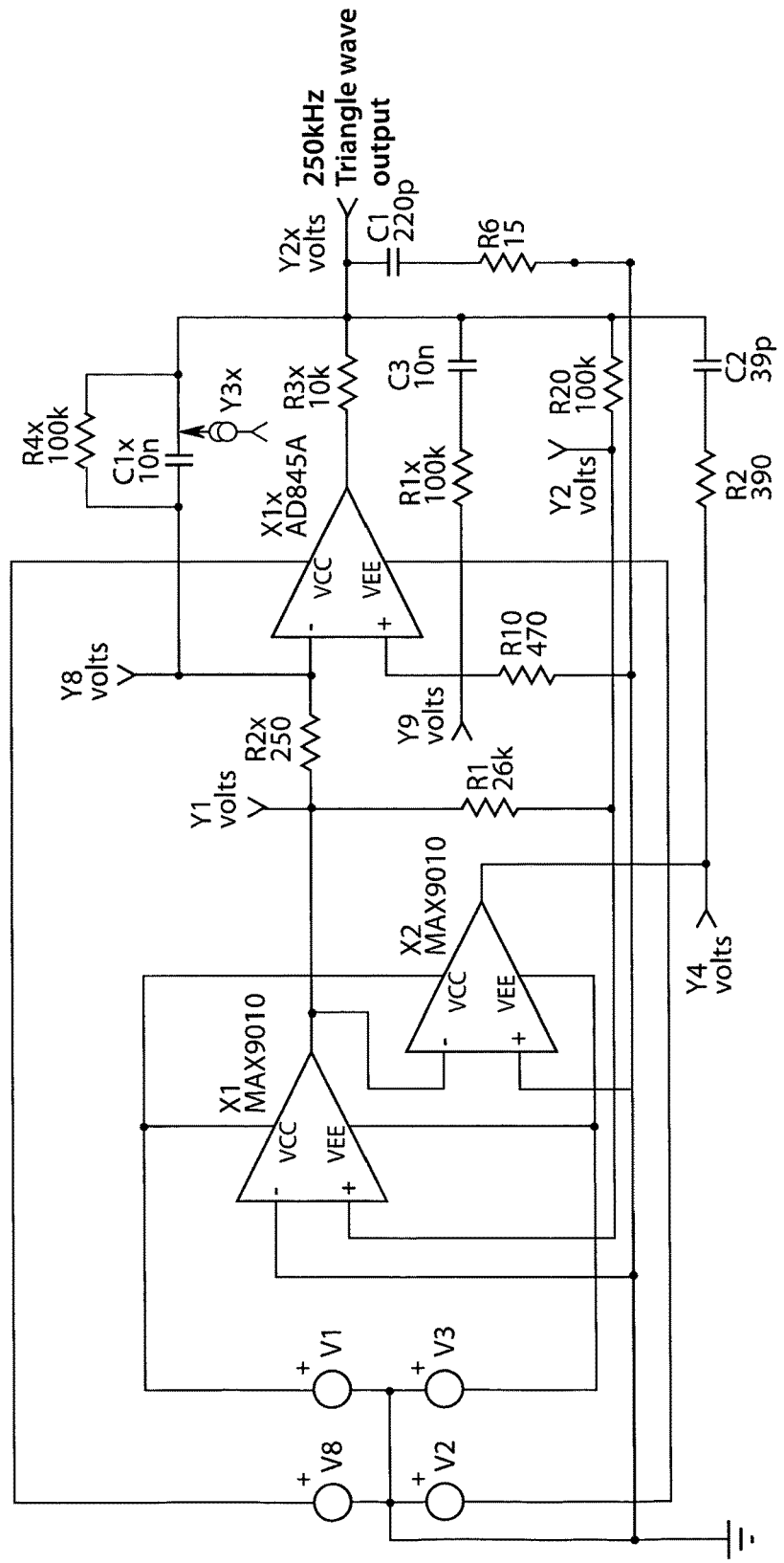
FIG. 8a is a circuit diagram showing further another embodiment of a PWMT amplifier, where the energy is transferred by ultrasonic waves.

The FIGS. 7i-7j shows the detailed views of the voltage over the receiving coil L1 and the PWMT amplifiers modulation signal with the 80% duty cycle. FIG. 8a shows a solution with a circuit employing a continuous square wave pulse signal with a constant base frequency where the duty cycle of each pulse is varied. The output voltage from the PWMT amplifier is linearly regulated by the input voltage. The mean digital output voltage from the PWMT amplifier is the same as the analog input voltage multiplied with the amplification factor of the circuit.

This type of amplifier can output any frequency within its frequency range from DC to about one third of the constant base frequency, the output to the load is a digital replica of the input voltage and not fixed to any particular frequency. However, in this example the PWMT amplifier is used with an input signal frequency of 25 kHz. The input signal to the amplifier is a 25 kHz sine wave and the output supplies the Piezo crystal and tuning circuit tuned to 25 kHz with a digital replica of the analog input signal. The crystal, X4 in the core schematic below, is the transmitting element.

The output power from the amplifier to the transmitting crystal can be regulated by adjusting the amplitude of the input sine wave signal.

FIG. 8a shows the triangle wave generator circuit which output is connected as an input in FIGS. 8b' and 8b" of the PWMT amplifier. In FIGS. 8a and 8b' and 8b" the symbols Y1, Y2, Y3 and so on symbolize test points within the circuit. References to the test points are found on the graphs in the diagrams following later in the text. The components in the circuit diagrams and their respective values are values that work in this particular implementation which of course is only one of an infinite number of possible design solutions.

FIG. 8a shows a circuit diagram containing most of the PWMT amplifier, in the lower left corner there is the LF input which is the input for the 25 kHz sine wave that should be amplified into a digital output signal. The LF-input there is the triangle wave input emanating from the Triangle schematic. To the right in the middle in the Core schematic there is the transmitting crystal, X4, connected to the differential digital outputs, positive and negative output, of the PWMT-amplifier. The transmitting crystal X4 is in series with its associated tuning circuit components tuned to the sending frequency, which in this particular case is 25 kHz. FIGS. 8c-8d displays the relationship between the input and the output signal of the PWM amplifier, in FIG. 8c Y25 is the input signal and Y2 is the positive digital output signal from the amplifier and in FIG. 8d Y13 is the negative digital output from the amplifier.

Figure 9A:
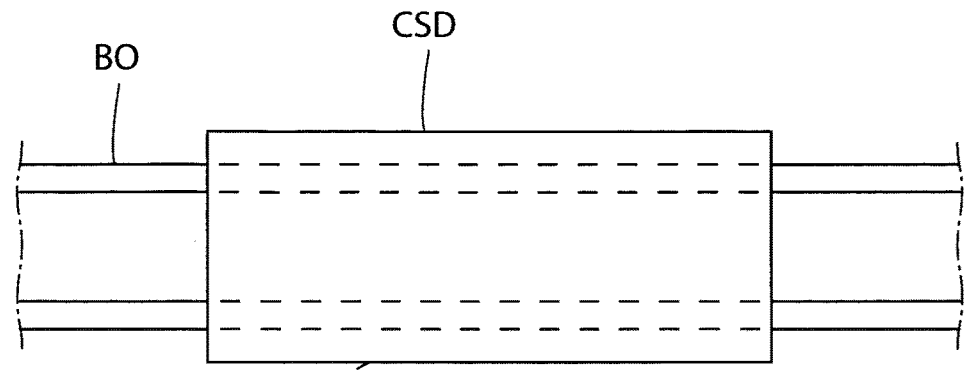
FIGS. 9a-9e schematically illustrate different states of operation of a general embodiment of an apparatus used with the present invention.
Figure 9A:
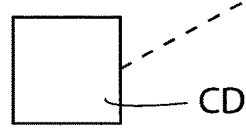
Figure 9B:
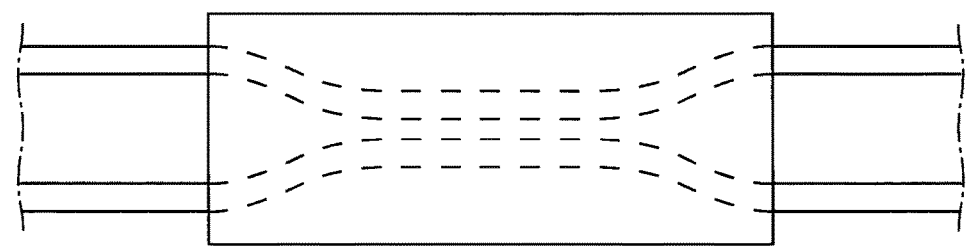
Figure 9C:
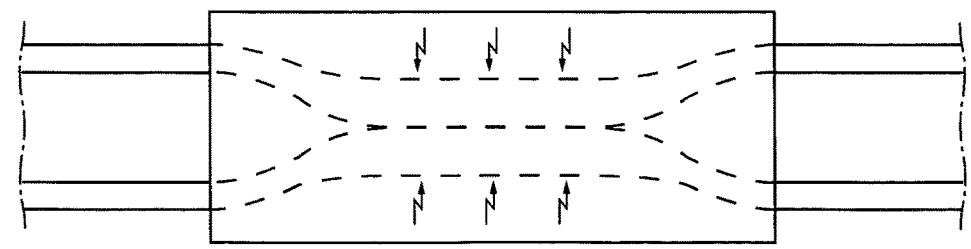

FIGS. 9a-9c schematically illustrate different states of operation of a generally designed apparatus used with the present invention, when the apparatus is applied on a wall portion of a bodily organ designated BO. The apparatus includes a constriction device and a stimulation device, which are designated CSD, and a control device designated CD for controlling the constriction and stimulation devices CSD. FIG. 9a shows the apparatus in an inactivation state, in which the constriction device does not constrict the organ BO and the stimulation device does not stimulate the organ BO. FIG. 9b shows the apparatus in a constriction state, in which the control device CD controls the constriction device to gently constrict the wall portion of the organ BO to a constricted state, in which the blood circulation in the constricted wall portion is substantially unrestricted and the flow in the lumen of the wall portion is restricted. FIG. 9c shows the apparatus in a stimulation state, in which the control device CD controls the stimulation device to stimulate different areas of the constricted wall portion, so that almost the entire wall portion of the organ BO contracts (thickens) and closes the lumen.

Figure 9D:
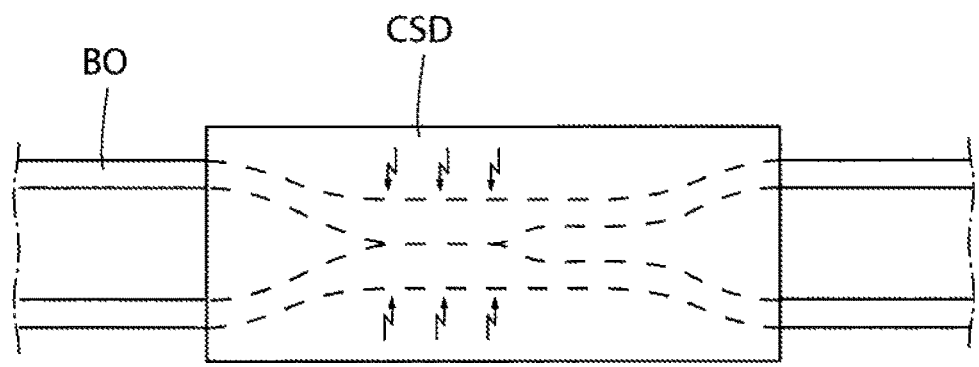
Figure 9E:
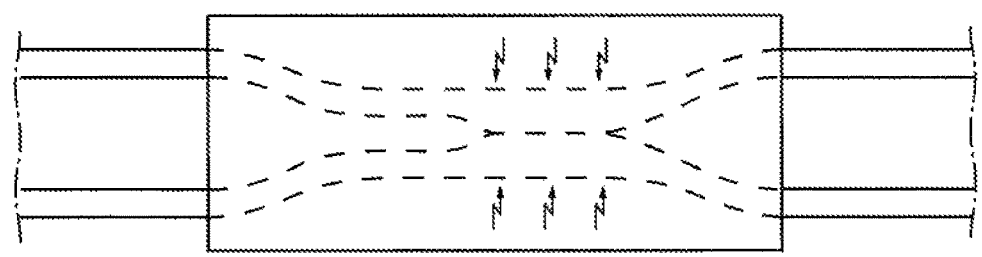

FIGS. 9d and 9e show how the stimulation of the constricted wall portion can be cyclically varied between a first stimulation mode, in which the left area of the wall portion (see FIG. 9d) is stimulated, while the right area of the wall portion is not stimulated, and a second stimulation mode, in which the right area of the wall portion (see FIG. 9e) is stimulated, while the left area of the wall portion is not stimulated, in order to maintain over time satisfactory blood circulation in the constricted wall portion.

It should be noted that the stimulation modes shown in FIGS. 9d and 9e only constitute a principle example of how the constricted wall portion of the organ BO may be stimulated. Thus, more than two different areas of the constricted wall portion may be simultaneously stimulated in cycles or successively stimulated. Also, groups of different areas of the constricted wall portion may be successively stimulated.

FIGS. 9f-9h illustrate different states of operation of a modification of the general embodiment shown in FIGS. 9a-9e, wherein the constriction and stimulation devices CSD include several separate constriction/stimulation elements, here three elements CSDE1, CSDE2 and CSDE3. FIG. 9f shows how the element CSDE1 in a first state of operation is activated to both constrict and stimulate the organ BO, so that the lumen of the organ BO is closed, whereas the other two elements CSDE2 and CSDE3 are inactivated. FIG. 9g shows how the element CSDE2 in a second following state of operation is activated, so that the lumen of the organ BO is closed, whereas the other two elements CSDE1 and CSDE3 are inactivated. FIG. 9h shows how the element CSDE3 in a following third state of operation is activated, so that the lumen of the organ BO is closed, whereas the other two elements CSDE1 and CSDE2 are inactivated. By shifting between the first, second and third states of operation, either randomly or in accordance with a predetermined sequence, different portions of the organ can by temporarily constricted and stimulated while maintaining the lumen of the organ closed, whereby the risk of injuring the organ is minimized. It is also possible to activate the elements CSDE1-CSDE3 successively along the lumen of the organ to move fluids and/or other bodily matter in the lumen.

FIGS. 9i-9k illustrate an alternative mode of operation of the modification of the general embodiment. Thus, FIG. 9i shows how the element CSDE1 in a first state of operation is activated to both constrict and stimulate the organ BO, so that the lumen of the organ BO is closed, whereas the other two elements CSDE2 and CSDE3 are activated to constrict but not stimulate the organ BO, so that the lumen of the organ BO is not completely closed where the elements CSDE2 and CSDE3 engage the organ BO. FIG. 9j shows how the element CSDE2 in a second following state of operation is activated to both constrict and stimulate the organ BO, so that the lumen of the organ BO is closed, whereas the other two elements CSDE1 and CSDE3 are activated to constrict but not stimulate the organ BO, so that the lumen of the organ BO is not completely closed where the elements CSDE1 and CSDE3 engage the organ BO. FIG. 9k shows how the element CSDE3 in a following third state of operation is activated to both constrict and stimulate the organ BO, so that the lumen of the organ BO is closed, whereas the other two elements CSDE1 and CSDE2 are activated to constrict but not stimulate the organ BO, so that the lumen of the organ BO is not completely closed where the elements CSDE1 and CSDE2 engage the organ BO. By shifting between the first, second and third states of operation, either randomly or in accordance with a predetermined sequence, different portions of the organ can by temporarily stimulated while maintaining the lumen of the organ closed, whereby the risk of injuring the organ is reduced. It is also possible to activate the stimulation of the elements CSDE1-CSDE3 successively along the lumen of the organ BO to move fluids and/or other bodily matter in the lumen.

Figure 10:
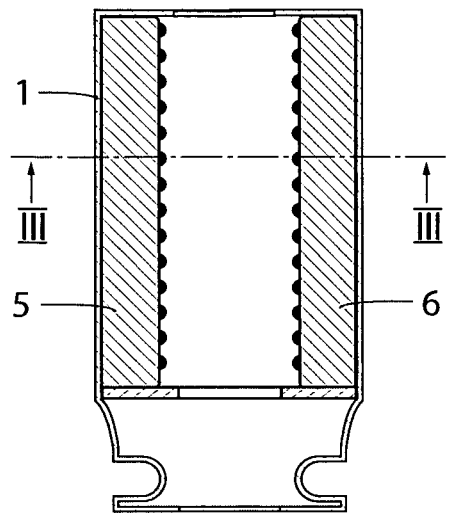
FIG. 10 is a longitudinal cross-section of a preferred embodiment of the apparatus including a constriction device and an electric stimulation device.
Figure 11:
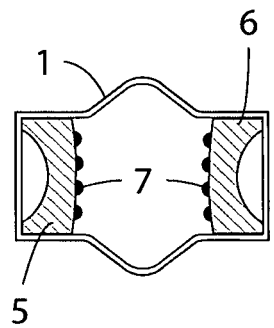
FIG. 11 is a cross-section along line III-III in FIG. 10.
Figure 12:
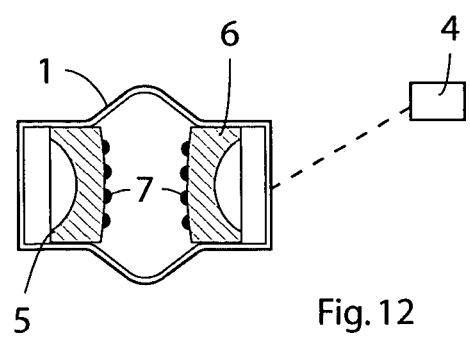
FIG. 12 is the same cross-section shown in FIG. 11, but with the apparatus in a different state of operation.

FIGS. 10-12 show basic components of an embodiment of the apparatus according to the invention for controlling a flow of fluid and/or other bodily matter in a lumen formed by a tissue wall of a patient's organ. The apparatus comprises a tubular housing 1 with open ends, a constriction device 2 arranged in the housing 1, a stimulation device 3 integrated in the constriction device 2, and a control device 4 (indicated in FIG. 12) for controlling the constriction and stimulation devices 2 and 3. The constriction device 2 has two elongate clamping elements 5, 6, which are radially movable in the tubular housing 1 towards and away from each other between retracted positions, see FIG. 11, and clamping positions, see FIG. 12. The stimulation device 3 includes a multiplicity of electrical elements 7 positioned on the clamping elements 5, 6, so that the electrical elements 7 on one of the clamping elements 5, 6 face the electrical elements 7 on the other clamping element. Thus, in this embodiment the constriction and stimulation devices form a constriction/stimulation unit, in which the constriction and stimulation devices are integrated in a single piece.

The constriction and stimulation devices may also be separate from each other. In this case, a structure may be provided for holding the electrical elements 7 in a fixed orientation relative to one another. Alternatively, the electrical elements 7 may include electrodes that are separately attached to the wall portion of the patient's organ.

The schematic FIG. 3 shows a circuit diagram of one of the proposed designs of the invented apparatus for controlling transmission of wireless energy, or energy balance control system. The schematic shows the energy balance measuring circuit that has an output signal centered on 2.5V and that is proportional to the energy imbalance. A signal level at 2.5V means that energy balance exists, if the level drops below 2.5V energy is drawn from the power source in the implant and if the level rises above 2.5V energy is charged into the power source. The output signal from the circuit is typically feed to an A/D converter and converted into a digital format. The digital information can then be sent to the external transmitter allowing it to adjust the level of the transmitted power. Another possibility is to have a completely analog system that uses comparators comparing the energy balance level with certain maximum and minimum thresholds sending information to an external transmitter if the balance drifts out of the max/min window.

Figure 13:
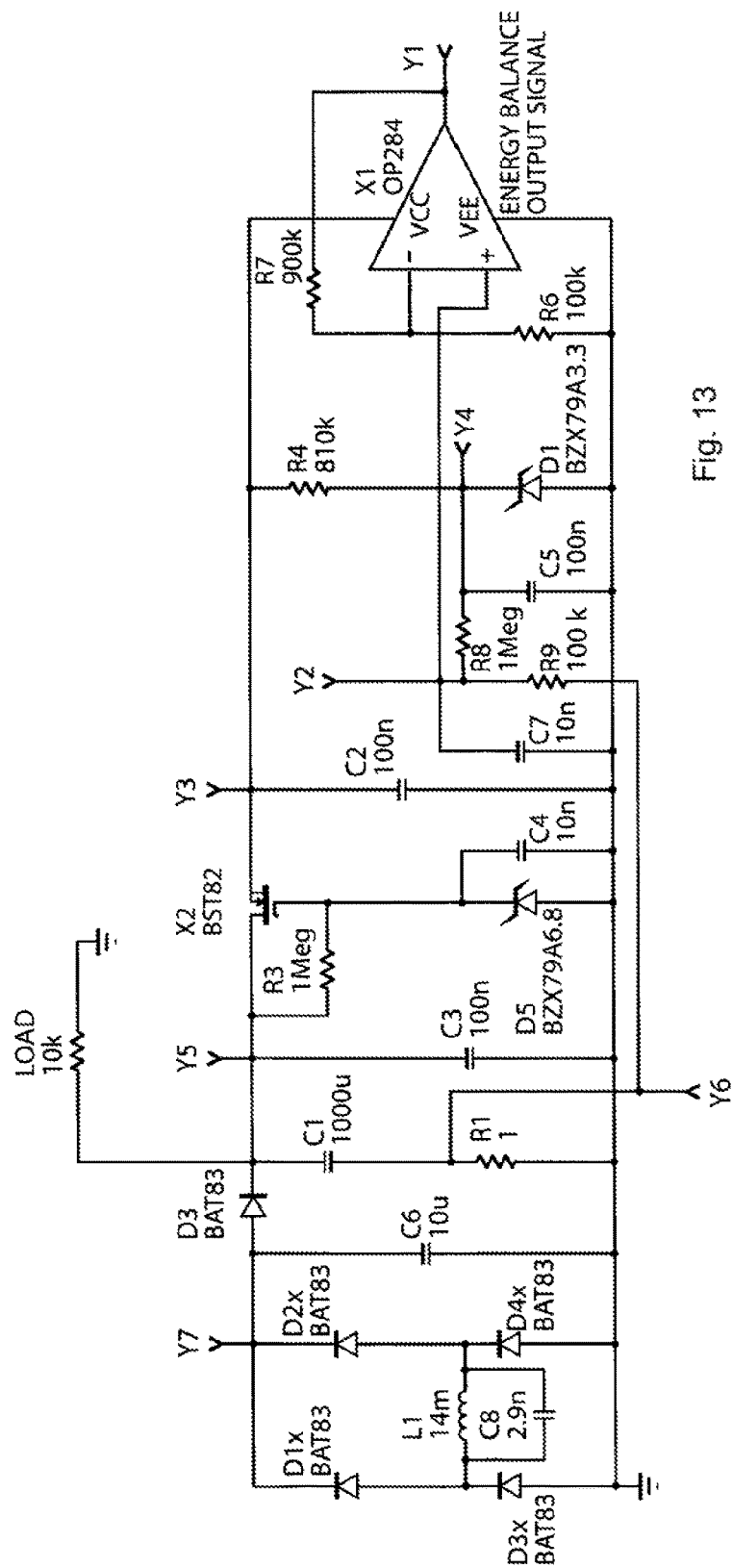
FIG. 13 is a schematic circuit diagram illustrating a proposed design of an apparatus for controlling transmission of wireless energy, according to a possible implementation example.

The schematic FIG. 13 shows a circuit implementation for a system that transfers power to the implant from outside of the body using inductive energy transfer with feedback control. An inductive energy transfer system typically uses an external transmitting coil and an internal receiving coil. The receiving coil, L1, is included in the schematic FIG. 13; the transmitting parts of the system are excluded.

The implementation of the general concept of energy balance and the way the information is transmitted to the external energy transmitter can of course be implemented in numerous different ways. The schematic FIG. 13 and the above described method of evaluating and transmitting the information should only be regarded as examples of how to implement the control system.

Circuit Details

In the schematic FIG. 13 the symbols Y1, Y2, Y3 and so on symbolize test points within the circuit. References to the test points are found on the graphs in the diagrams following later in the text. The components in the diagram and their respective values are values that work in this particular implementation which of course is only one of an infinite number of possible design solutions.

Energy to power the circuit is received by the energy receiving coil L1. Energy to the implant is transmitted in this particular case at a frequency of 25 kHz. The energy balance output signal is present at test point Y1.

Figure 14:
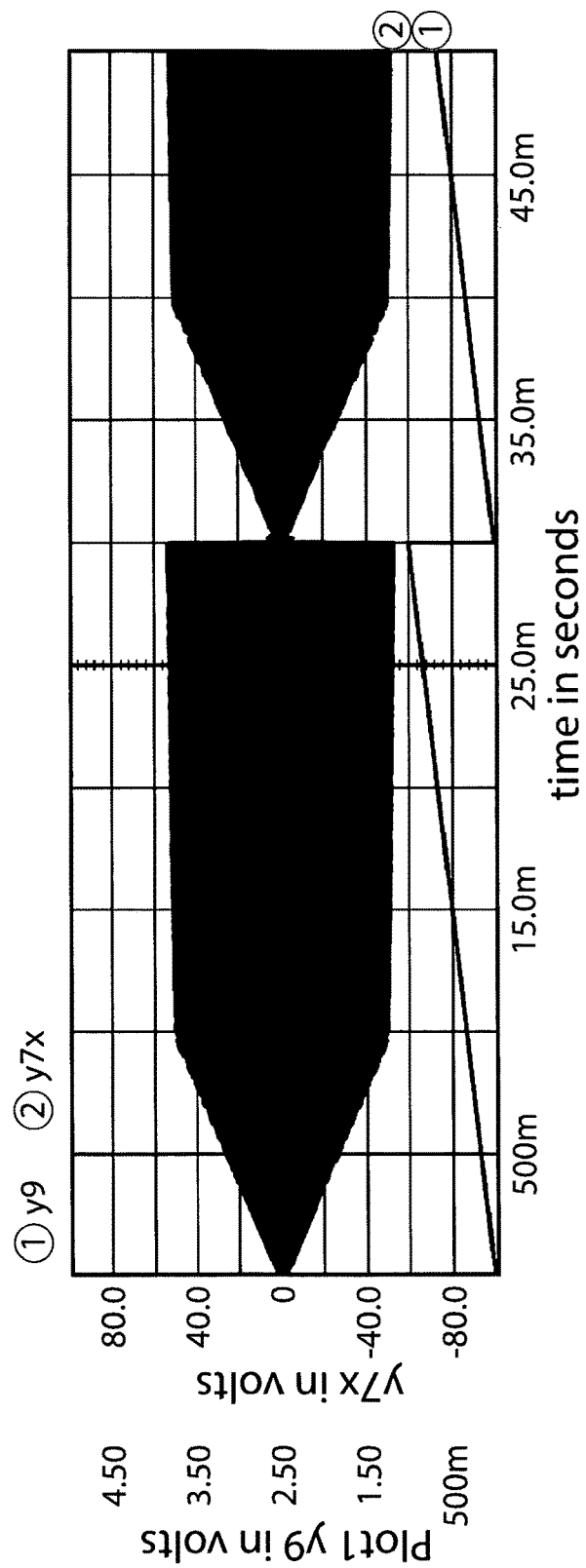

The diagram in FIG. 14 shows the voltage, Y7$x$, over the receiving coil L1 and the input power, Y9, received by the coil from the external transmitter. The power graph, Y9, is normalized and varies between 0-1 where 1 signifies maximum power and 0 no power; hence Y9 does not show the absolute value of the received power level. The power test point Y9 is not present in the schematic, it is an amplitude modulation signal on the transmitter signal power. In the diagram it can be seen that the Y7$x$ voltage over the receiving coil L1 increases as the power from the external transmitter increases. When the Y7$x$ voltage reaches the level where actual charging of the power source, C1, in the implant commences the Y7$x$ level increases at a much slower rate as the input power is increased because of the load that the power source impart on the receiving coil.

Figure 15:
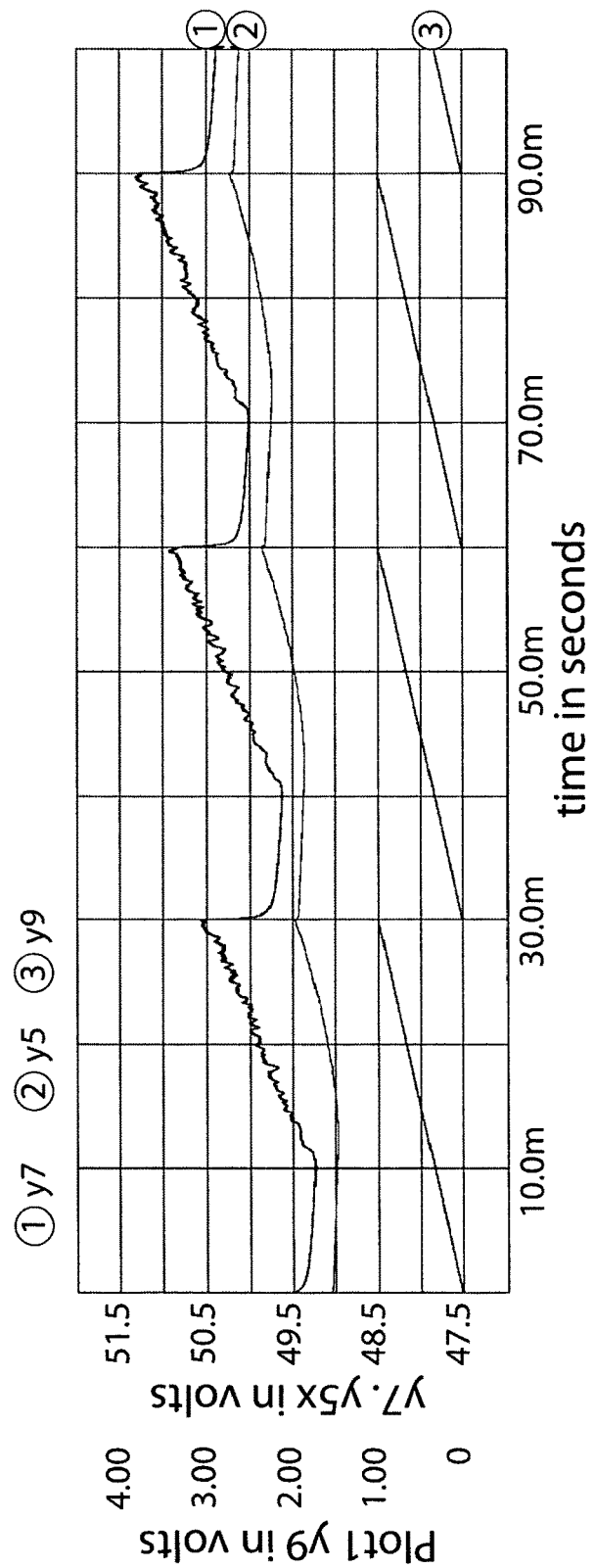

The receiving coil L1 is connected to a rectifying bridge with four Schottky diodes, D1$x$-D4$x$. The output voltage from the bridge, Y7, is shown in the diagram of FIG. 15. The capacitor C6 absorbs the high frequency charging currents from the bridge and together with the Schottky diode D3 prevents the 25 kHz energy transmission frequency from entering into the rest of the circuit. This is beneficial since the energy balance of the system is measured as the voltage across R1, which with out the C6-D3 combination would contain high level of 25 kHz alternating charge current. The power source in the implant is the capacitor C1. The capacitor C3 is a high frequency decoupling capacitor. The resistor named LOAD is the fictive load of the power source in the implant. The voltage over the power source, Y5, is also shown in the diagram of FIG. 15 together with the power graph Y9.

Figure 16:
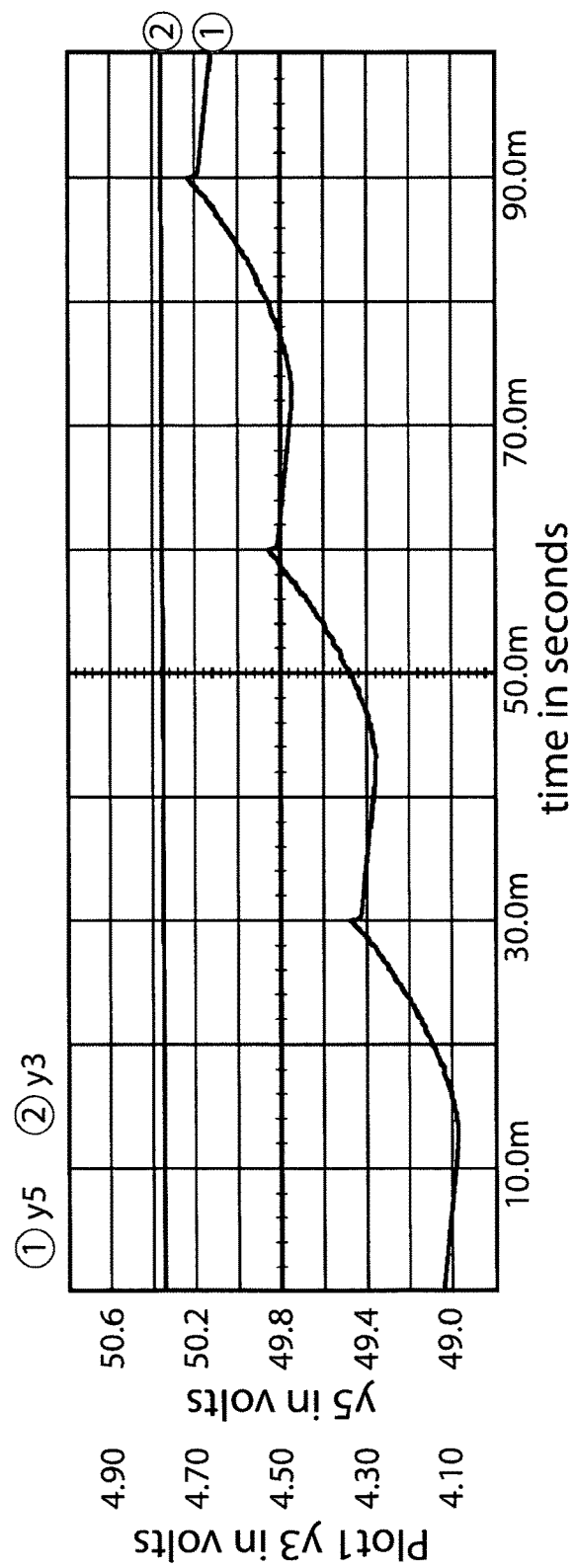

The voltage Y3 in the diagram of FIG. 16 is a stabilized voltage at about 4.8V used to power the operational amplifier X1. The Y3 voltage is stabilized by a fairly standard linear voltage regulator consisting of the MosFet X2, zener-diode D5, capacitor C4 and resistor R3. The capacitor C2 is a high frequency decoupling capacitor. In the diagram of FIG. 16 the input voltage to the regulator is seen as Y5 and the output voltage is Y3.

Figure 17:
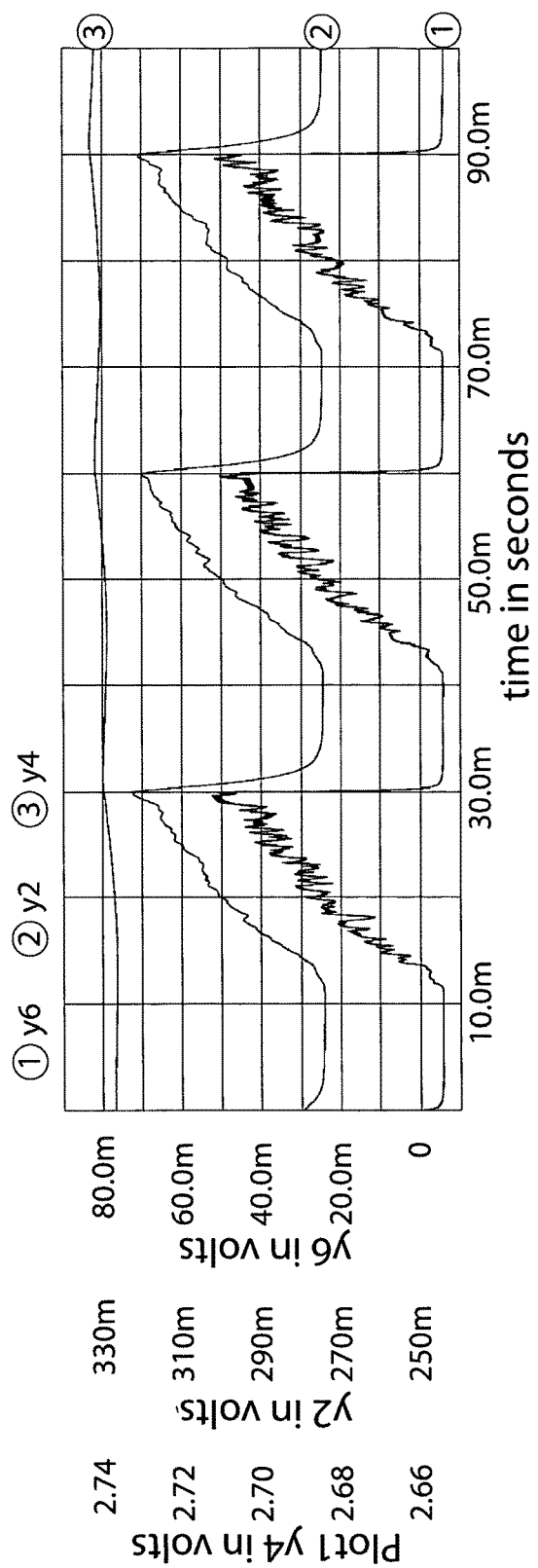

The X1 operational amplifier is used to amplify the energy balance signal together with R6 and R7 that set the gain of the amplifier circuit to 10 times. The input signals to the circuit are shown in the diagram of FIG. 17. Y4 is fixed at a more or less constant level of approximately 2.74V by the zener diode D1. The voltage Y4 is shunted and high frequency filtered by the capacitor C5. A part of the DC voltage at Y4 is coupled into the Y2 voltage by the resistor R8 in order to center the Y1 output voltage at 2.5V when energy is balanced. The voltage Y2 is basically the same voltage as the voltage, Y6, over R1, only slightly high frequency filtered by R9 and C7 and shifted in DC level by the current going through R8. To compare Y6 and Y2 look in the diagram of FIG. 17.

Figure 18:
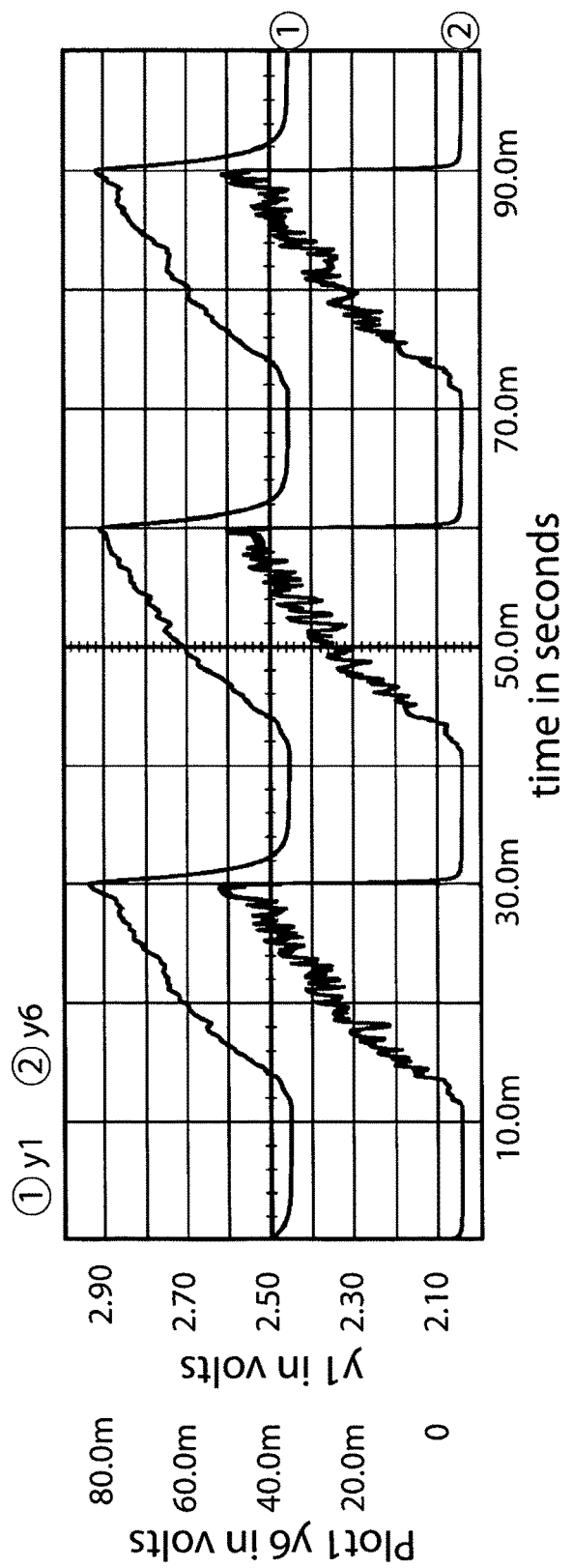

The energy balance output signal of the circuit, Y1 in the diagram of FIG. 18, also closely corresponds to the Y6 voltage. The Y1 voltage is an amplified, 10 times, and DC shifted to center around 2.5V instead of 0V version of the Y6 voltage. The higher signal level at Y1 and the DC center point around 2.5V is much easier to interface to for the circuits connected to the energy balance output signal.

The diagram of FIG. 19 shows the relationship between the energy balance signal Y1 and the actual voltage over the power source of the implant. The energy balance signal is the derivative of the voltage level over the power source, Y5. When the energy balance signal, Y1, is negative relative to 2.5V the voltage level, Y5, drops off and when the energy balance signal is positive relative to 2.5V the Y5 voltage increases. The more negative or positive relative to 2.5V the energy balance signal Y1 is the more rapidly the Y5 voltage over the power source increases or decreases.

The diagram of FIG. 20, of another circuit condition, perhaps even more clearly shows how the energy balance signal corresponds to the derivative of the Y5 voltage over the power source. The traces shows a situation where the energy put into the power source is held at a constant level and the load is varied between 5 mA and 30 mA in four discrete steps. During the first 25 ms the load is 30 mA, the following 25 ms it is 5 mA then followed by the same 30 mA and 5 mA sequence. When the Y5 voltage over the power source decreases at a constant level due to the 30 mA load the derivative level is at a constant level below 2.5V and when the Y5 voltage increases the derivative voltage is positive at a constant level.

The two diagrams of FIG. 21 show the relation ship between the energy balance signal Y1 and the energy imbalance in the circuit in a complex situation where both the load is varied and the amount of power put into the implant is varied. The two traces in the first diagram of FIG. 21 shows the charging current into the power source and the load current. The charging current is represented by the IY12 trace and the load current is the IY10 trace. The second diagram of FIG. 21 shows the Y1 voltage generated by the altering currents shown in the first diagram. When the amount of stored energy in the power source is changed due to the energy imbalance the derivative signal Y1 rapidly responds to the imbalance as shown in the diagram.

In a system where the energy balance signal is used as a feedback signal to an external power transmitter, enabling it to regulate the transmitted power according to the energy imbalance, it is possible to maintain an optimal energy balance and to keep the efficiency at maximum. The diagram of FIG. 22 shows the charging current into the power source and the load current, the charging current are represented by the IY12 trace and the load current is the IY10 trace, as well as the voltage level over the power source, Y5, and the energy balance signal Y1 in such a system. It can clearly be seen that this system rapidly responds to any load current changes by increasing the charging current. Only a small spike in the energy balance signal can be seen right at the edges where the load is rapidly changed due to the finite bandwidth of the feedback loop. Apart from those small spikes the energy is kept in perfect balance.

By the described examples above it is clear that the modified PWMT approach that switches a continuous pulse train off during several pulse periods and then on again for several pulse periods is capable of adjusting the amount of power supplied to a receiving circuit over a quite broad range of loads. With a duty cycle variation between 2% and 80% it is possible to obtain energy balance with loads varying from 4 mA to 80 mA. In this particular case the PWMT duty cycle closely corresponds to the load in the system, a 80 mA load needs 80% duty cycle for energy balance and a 40 mA load needs 40%. The only divergence from this almost perfectly linear transfer function is the 2% duty cycle that balances the 4 mA load. The reason for this irregularity is that the 2% duty cycle actually produces a 4% duty cycle voltage over the receiving coil due to the previously discussed energy storage in the transmitting parallel resonance circuit.

As mentioned in connection with FIG. 1, suitable sensors may be used for measuring certain characteristics of the medical device and/or detecting the current condition of the patient, somehow reflecting the required amount of energy needed for proper operation of the medical device. Thus, electrical and/or physical parameters of the medical device and/or physical parameters of the patient may be determined, and the energy can then be transmitted with a transmission rate which is determined based on the parameters. Further, the transmission of wireless energy may be controlled such that the total amount of transmitted energy is based on said parameters.

It should be understood that all the different embodiments described herein may be used both as methods and with an apparatus adapted to achieve the above.

It should also be noted that FIGS. 1-22 illustrate some possible but non-limiting implementation options regarding how the various shown functional components and elements can be arranged and connected to each other. However, the skilled person will readily appreciate that many variations and modifications can be made within the scope of the present invention.

The invention claimed is:

1. A method of transmitting wireless energy from an external energy transmitting device placed externally to a human body to an internal energy receiver placed internally in the human body, the method comprising,
supplying by a first electric circuit, electrical pulses having leading and trailing edges to the external transmitting device, according to at least one of the following:
varying the lengths of first time intervals between successive leading and trailing edges of the electrical pulses and/or the lengths of second time intervals between successive trailing and leading edges of the electrical pulses, and
varying the first and second time intervals to have lengths in the range of, that are in the magnitude of order of or are shorter than, a time constant of the first electric circuit, and a relationship or proportion between the lengths of the first and second time intervals, whereby, by the varying a varying power is transmitted, the method further comprising:
transmitting by the external energy transmitting device, the wireless energy generated from the electrical pulses to the internal energy receiver placed internally in the human body.

2. The method of claim 1, further comprising:
varying the first and second time intervals to have lengths in the range of, that are in the magnitude of order of or are relatively longer than the time constant of the first electric circuit, according to at least one of the following; for first time intervals having lengths that are long compared to the first time constant and second time intervals having adapted lengths shorter than the lengths of the first time intervals, adapted lengths that are in the range of, particularly are in the magnitude of order of or are shorter than, the first time constant, for second time intervals having lengths that are long compared to the first time constant and first time intervals having adapted lengths shorter than the lengths of the first time intervals, adapted lengths that are in the range of, particularly are in the magnitude of order of or are shorter than, the first time constant, or for first and second time intervals both having adapted lengths, that are in the range of, particularly are in the magnitude of order of or are shorter than, the first time constant, and
varying the lengths of the first and/or second time intervals in the range from lengths relatively long compared to the time constant in the magnitude of order of the first time constant to shorter lengths, to transmit a varying power.

3. The method according to claim 1, further comprising:
receiving by the first electric circuit, feedback information transmitted from the internal energy receiver, the wireless feedback information being related to the level of the power of the transmitted wireless energy as received by the receiver, and
varying by the first electric circuit, the first and second time intervals to vary the transmitted power in response to said feedback information.

4. The method according to claim 1, further comprising:
regulating by an external control unit, the amount of energy emitted from the external energy source transmitting device, wherein this step is repeated intermittently at intervals during ongoing energy transfer, in the preferred embodiment many times per second, and/or executed on a more or less continuous basis during the energy transfer.

5. The method according to claim 1, wherein when supplying the electrical pulses, the electrical pulses remain unchanged, except for varying the first and/or second time intervals.

6. The method according to claim 1, further comprising:
keeping by the first electrical circuit, at least one of; the frequency of the electrical pulses substantial constant when the first and/or second time intervals are varied and the amplitude of the electrical pulses substantial constant when the first and/or second time intervals are varied.

7. The method according to claim 1, further comprising:
supplying a train of two or more electrical pulses in a row, wherein when supplying the train of pulses, said train has a first electrical pulse at the start of the pulse train and has a second electrical pulse at the end of the pulse train, and
supplying two or more pulse trains in a row, wherein the lengths of the second time intervals between successive trailing edge of the second electrical pulse in a first pulse train and leading edge of the first electrical pulse of a second pulse train are varied.

8. The method according to claim 1, further comprising at least one of the following:
a) regulating an output power from an amplifier by repetitive switching the power on and off; and
b) supplying a train of two or more electrical pulses in a row, wherein when supplying the train of pulses, said train has a first electrical pulse at the start of the pulse train and has a second electrical pulse at the end of the pulse train, and supplying two or more pulse trains in a row, wherein the lengths of the second time intervals between successive trailing edge of the second electrical pulse in a first pulse train and leading edge of the first electrical pulse of a second pulse train are varied, wherein the method further comprising:
switching a continuous pulse train off during one or more pulse periods and then on again for one or more pulse periods thereby being capable of adjusting the amount of power supplied to a receiving circuit.

9. The method according to claim 1, further comprising:
receiving resulting pulses from the transmitted wireless energy having a varied power by a receiver placed internally in the human body.

10. The method according to claim 9, further comprising:
supplying the energy received by the internal energy receiver to a medical device with at least one of; at least one constant voltage, wherein the constant voltage is created by a constant voltage circuitry, and at least one constant current, wherein the constant current is created by a constant current circuitry.

11. The method according to claim 10, further comprising:
supplying the energy with at least one of; at least two different voltages, including the at least one constant voltage, and at least two different currents including said at least one constant current.

12. The method according to claim 9, further comprising:
receiving by a second electric circuit having a second time constant, the transmitted wireless energy as received pulses, and
varying by a second time constant control device of the second electric circuit, the second time constant to make the received wireless energy varied.

13. The method according to claim 1, further comprising:
transmitting the wireless energy inductively from a primary coil in the external energy transmitting device to a secondary coil in the internal energy receiver.

14. The method according to claim 13, further comprising:
reducing the energy transmission over the primary coil, when the lengths of the first time intervals are reduced, and
increasing the resulting energy transmission over the primary coil, when the lengths of the second time intervals are reduced.

15. The method according to claim 1, further comprising:
reducing the energy transmission over external energy transmitting device, when the lengths of the first time intervals are reduced, and
increasing the resulting energy transmission over external energy transmitting device, when the lengths of the second time intervals are reduced.

16. The method according to claim 1, for controlling transmission of wireless energy supplied to an electrically operable medical device when implanted in a patient, comprising:
receiving by an internal energy receiver located inside the patient, said wireless energy from said external energy source located outside the patient, wherein the internal energy receiver being connected to the medical device for directly or indirectly supplying received energy thereto, the method further comprising:
determining an energy balance between the energy received by the internal energy receiver and the energy used for the medical device, and
controlling the transmission of wireless energy from the external energy transmitting device, based on the determined energy balance, having varying power depending on the lengths of the first and/or second time intervals.

17. The method according to claim 16, further comprising:
detecting a change in said energy balance,
controlling the transmission of wireless energy based on said detected energy balance change, and
controlling a difference between energy received by said internal energy receiver and energy used for the medical device, and the transmission of wireless energy, based on said detected energy difference, the method further comprising:
decreasing the amount of transmitted wireless energy if at least one of, the detected energy balance change implies that the energy balance is increasing, or vice versa, wherein the decrease/increase of energy transmission corresponds to a detected change rate, and the detected energy difference implies that the received energy is greater than the used energy, or vice versa, wherein the decrease/increase of energy transmission corresponds to the magnitude of said detected energy difference.

18. The method according to claim 16, further comprising at least one of;
detecting the change in the amount of consumed and/or stored energy by determining over time the derivative of a measured electrical parameter related to said amount of consumed and/or stored energy, the derivative at a first given moment corresponding to the rate of the change at the first given moment, wherein the rate of change includes the direction and speed of the change, the method further comprising:
determining said derivative based on a detected rate of change of an electrical parameter, and
determining the energy balance based on a detected difference between the total amount of energy received by the internal energy receiver and the total amount of consumed and/or stored energy, said detected difference being related to the integral over time of at least one measured electrical parameter related to said energy balance, thus when plot values of said electrical parameter over time as a graph in a parameter-time diagram, said integral depends from the size of the area beneath the plotted graph, wherein said integral of the electrical parameter relates to the energy balance as an accumulated difference between the total amount of energy received by said internal energy receiver and the total amount of consumed and/or stored energy.

19. The method according to claim 1, further comprising:
determining electrical and/or physical parameters of the medical device and/or physical parameters of the patient, to calculate a required energy for the medical device to operate, and
storing the energy in at least one energy storage device of the medical device with a storing rate which is determined based on at least one of said parameters.

20. The method according to claim 19, further comprising:
storing the energy received by the internal energy receiver in a first energy storage device of the energy storage devices, such that the first energy storage device being charged at a higher energy rate than a second energy storage device, enabling a faster charging, and
supplying the energy from the first energy storage device to the second energy storage device at a later stage, wherein the first energy storage device is being able to charge more often, having a larger life-time in terms of charging events.

21. The method according to claim 1, further comprising:
controlling by an implantable construction device in a medical device, a flow of fluid and/or other bodily matter in a lumen formed by a tissue wall of a patient's organ for gently constricting at least one portion of the tissue wall to influence the flow in the lumen.

22. The method according to claim 1, further comprising:
supplying by the first electric circuit, a continuums square wave pulse signal with a constant frequency, and
regulating the width of the output pulses from a PWMT amplifier in a linear manner.

23. The method according to claim 1, wherein in the step of supplying by the first electric circuit the electrical pulses, said relationship or proportion between the lengths of the first and second time intervals varies according to a sinusoidal.

24. The method according to claim 1, further comprising:
stabilizing by a capacitor, the energy received by the internal energy receiver, before the energy is supplied directly or indirectly to the medical device.

25. The method according to claim 1, further comprising:
regulating the amount of transferred energy by using at least one PWMT in the energy source, and
modulating at least one of; a voltage, a current, an amplitude, a wave frequency, and a pulse characteristic, when modulating the width of the energy pulses to vary at least one of said first and second time intervals.

* * * * *